(12) United States Patent
Awasthi

(10) Patent No.: US 8,623,832 B2
(45) Date of Patent: Jan. 7, 2014

(54) PEPTIDE COMPOSITIONS THAT BIND TLR-4

(75) Inventor: Shanjana Awasthi, Edmond, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 0 days.

(21) Appl. No.: 13/289,820

(22) Filed: Nov. 4, 2011

(65) Prior Publication Data

US 2012/0115797 A1    May 10, 2012

(51) Int. Cl.
| C07K 14/705 | (2006.01) |
| C07K 14/435 | (2006.01) |
| A61K 38/04  | (2006.01) |
| A61K 38/16  | (2006.01) |

(52) U.S. Cl.
USPC ....... 514/21.3; 514/21.4; 514/21.5; 514/21.6; 514/21.7; 514/21.8; 530/300; 530/324; 530/326; 536/23.5

(58) Field of Classification Search
None
See application file for complete search history.

(56) References Cited

PUBLICATIONS

Lazar et al Mol. Cell. Biol., 1988, vol. 8, pp. 1247-1252.*
Wells, 1990, Biochemistry, vol. 29, pp. 8509-8517.*
Bork, 2000, Genome Research, 2000, vol. 10, pp. 398-400.*
Doerks et al., 1998, Trends in Genetics, vol. 14, pp. 248-250.*
Tokuriki and Tawflik, Current Opinion in Structural Biology, 2009, vol. 19, pp. 596-604.*
Skolnick et al., Trends in Biotech, 2000, vol. 18, No. 1, apges 34-39.*
Awasthi et al, The Journal of Pharmacology and Experimental Therapeutics, 2011, vol. 336, No. 3, pp. 672-681.*

* cited by examiner

*Primary Examiner* — Bridget E Bunner
*Assistant Examiner* — Fozia Hamud
(74) *Attorney, Agent, or Firm* — Dunlap Codding, P.C.

(57) ABSTRACT

Compositions that include isolated peptides that inhibit TLR-4 signaling pathways and inflammation are disclosed. Methods of producing and using the compositions to inhibit TLR-4 signaling and/or inflammation are also disclosed herein.

8 Claims, 28 Drawing Sheets
(15 of 28 Drawing Sheet(s) Filed in Color)

Figure 3
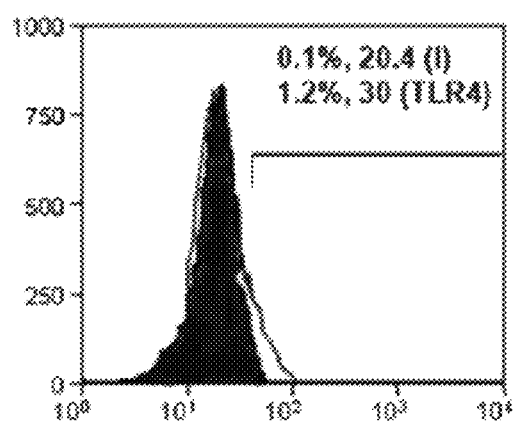
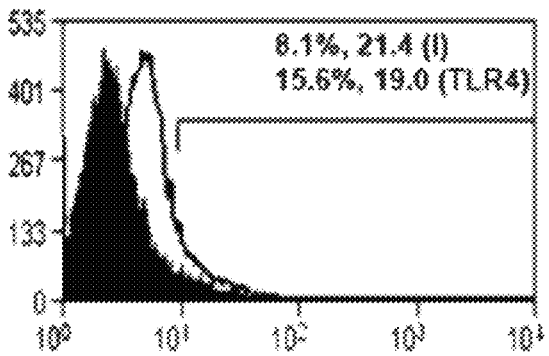
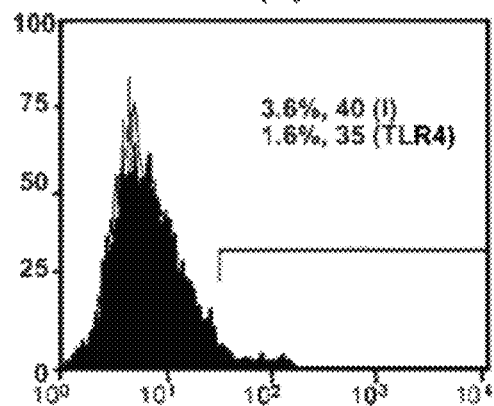
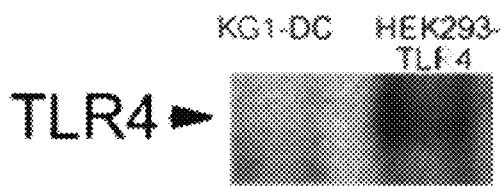

Figure 4 (A) 1h (B) 4h
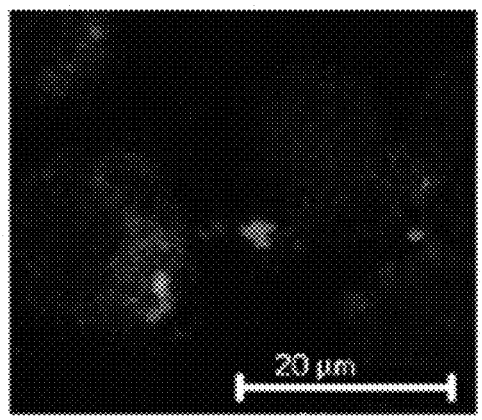
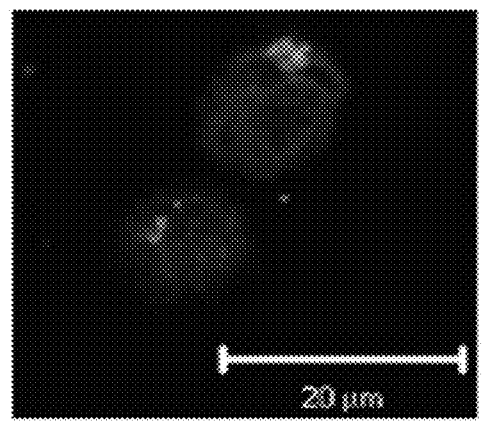
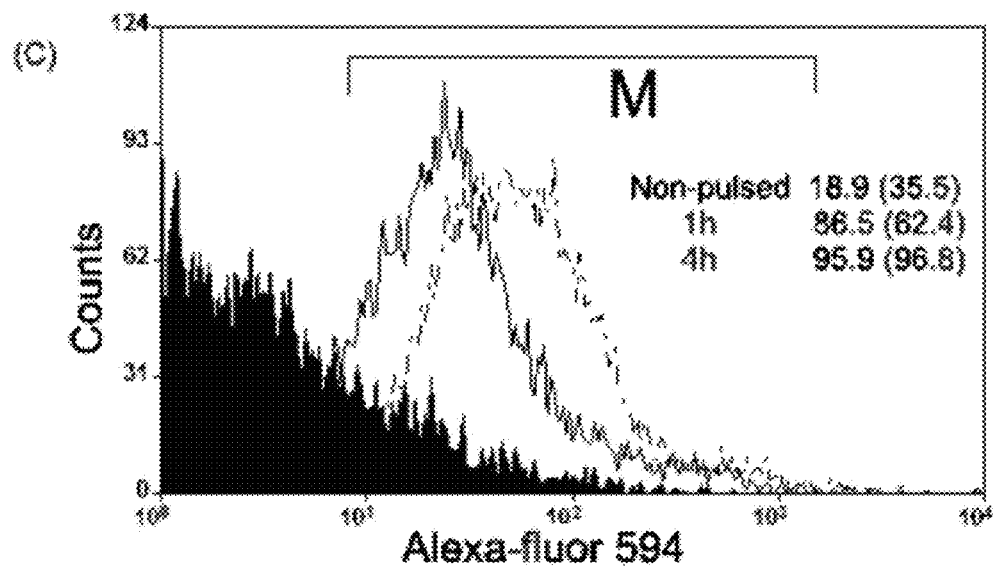

Figure 5
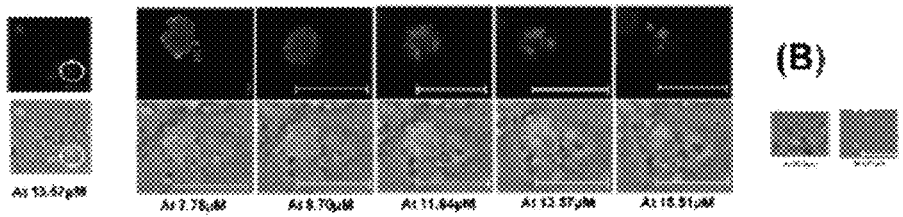
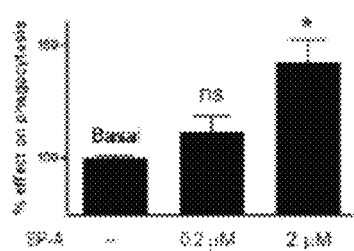
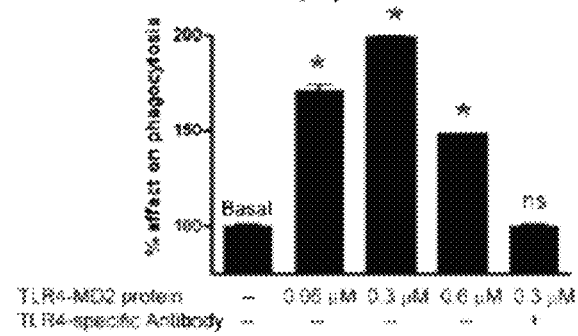
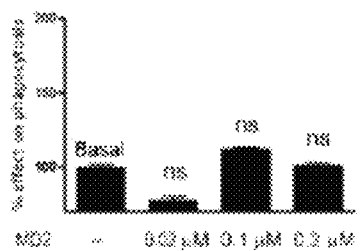
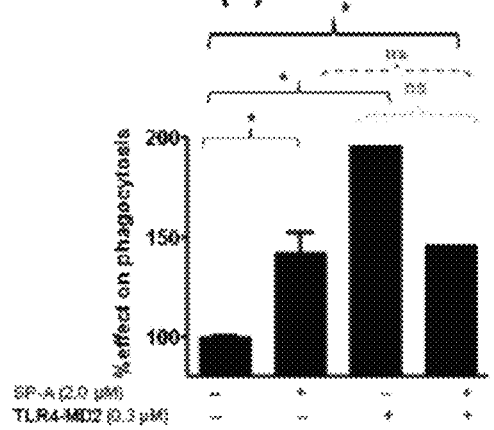

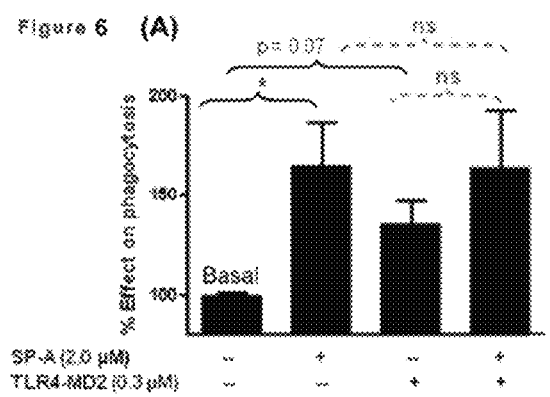
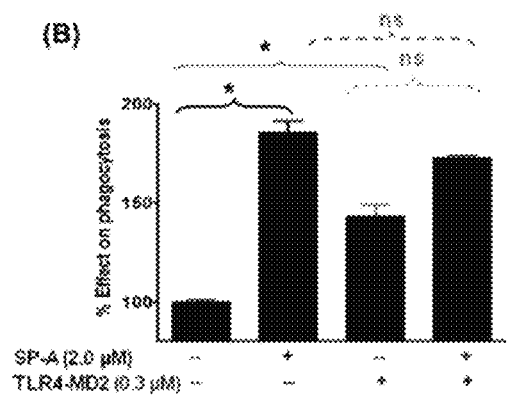
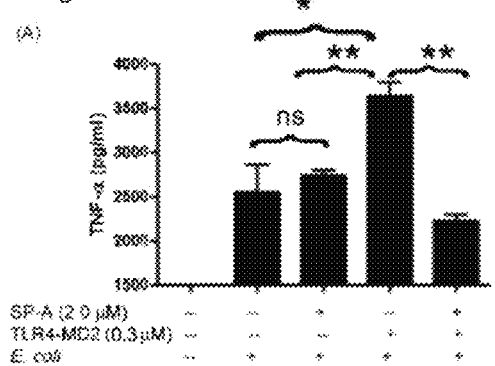
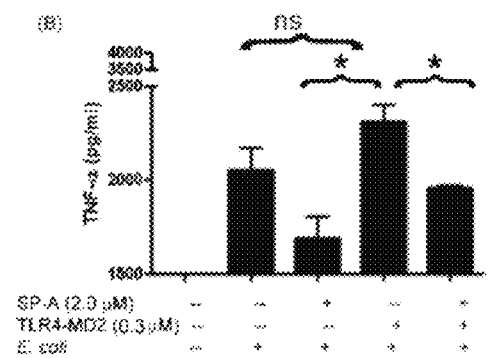

SEQ ID NO:
- 258 SPA1: EMYTDGQWNDRNCLYSRLTI
- 259 SPA2: PAGRGKEQCVEMYTDGQWND
- 4 SPA3: VNYTNWYRGEPAGRGKEQCV
- 3 SPA4: GDFRYSDGTPVNYTNWYRGE
- 5 SPA5: YVGLTEGPSPGDFRYSDGTP
- 260 SPA6: SFVKKYNTYAYVGLTEGPSP
- 261 SPA7: SLQGSIMTVGEKVFSSNGQS

Figure 9
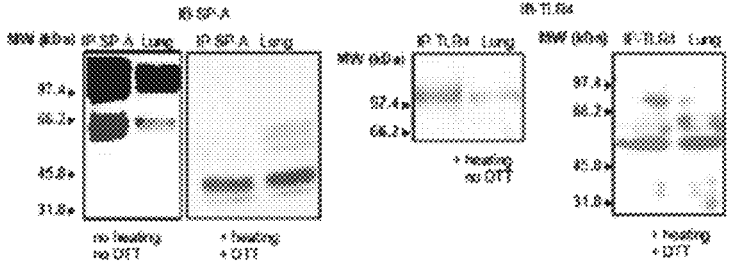
(A) Immunoblotting of immunoprecipitated SP-A and TLR4 proteins from baboon lung
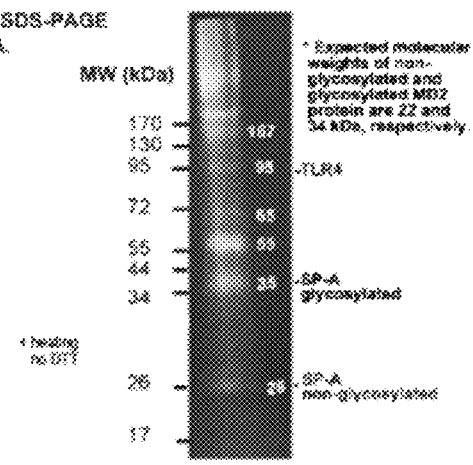
(B) SYPRO-ruby stained SDS-PAGE gel pattern of IP-SP-A
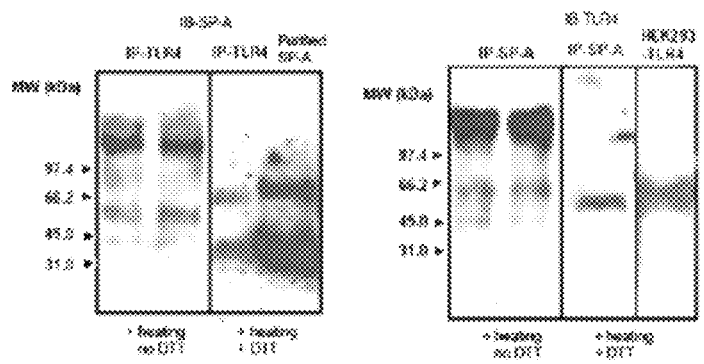
(C) Cross-immunoblotting of IP-SP-A and IP-TLR4
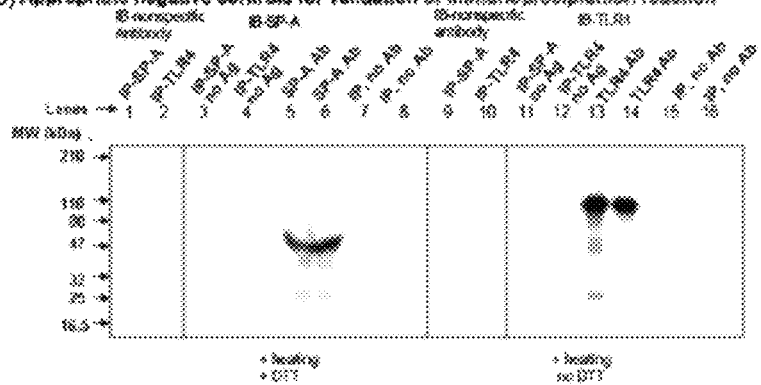
(D) Appropriate negative controls for validation of immunoprecipitation reaction

Figure 11

(Right panel)

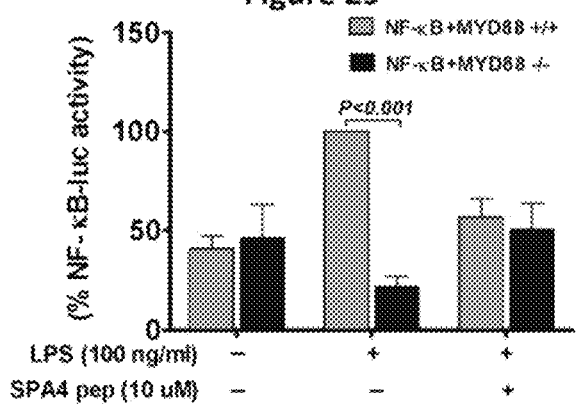
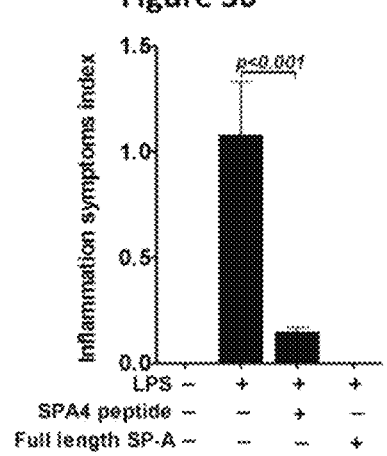
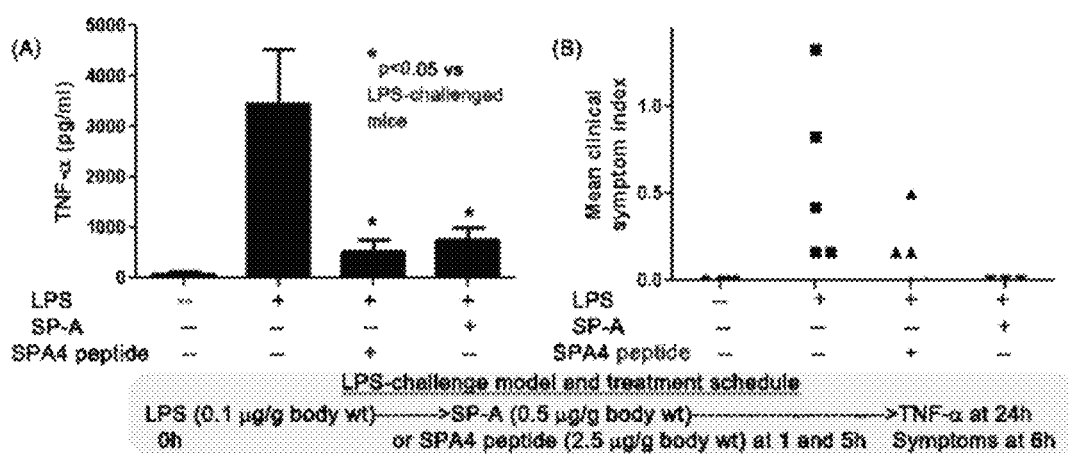

PEPTIDE COMPOSITIONS THAT BIND TLR-4

CROSS REFERENCE TO RELATED APPLICATIONS

The present application claims benefit under 35 U.S.C. 119(e) of provisional patent applications U.S. Ser. No. 61/410,077, filed Nov. 4, 2010; and U.S. Ser. No. 61/469,202, filed Mar. 30, 2011. The entire contents of the above-referenced patent applications are hereby expressly incorporated herein by reference.

STATEMENT REGARDING FEDERALLY SPONSORED RESEARCH OR DEVELOPMENT

Not Applicable.

BACKGROUND OF THE INVENTION

1. Field of the Inventive Concept(s)

The presently disclosed and claimed inventive concept(s) relates generally to peptide compositions, and in particular, but not by way of limitation, to Surfactant-A-protein peptide compositions and derivatives thereof, and methods of producing and using same.

2. Description of the Background Art

The pathogen-pattern recognition receptors (PPRRs) are important components of innate immunity that sense the pathogenic stimuli and regulate host immune responses (Pastva et al., 2007; Wright, 1997). Surfactant protein-A (SP-A) and Toll-like receptor-4 (TLR4) have been identified as important PPRRs (Barton, 2007; Brinker et al., 2003; Hoebe et al., 2006; Kawai and Akira, 2007; Kuroki et al., 2007; Miyake, 2007). TLR4 is expressed as a transmembrane receptor and is known as a "Signalling-PPRR" (Kawai and Akira, 2007). On the other hand, SP-A is synthesized by type II lung epithelial cells and secreted in the alveoli as a component of surfactant. SP-A is known as a "Secretory-PPRR" (Pastva et al., 2007). It has been demonstrated by the inventor and others that SP-A constitutes the majority of surfactant proteins (SPs) (Johansson and Curstedt, 1997) and plays a critical role in the clearance of pathogens and downregulation of the inflammatory response (see also, Awasthi, 2010). On the other hand, TLR4 recognizes pathogen or pathogen-derived ligands and endogenous stress proteins, and induces inflammatory and adaptive immune responses. In a number of diseases, including but not limited to lung inflammatory conditions, an exaggerated activation of TLR4 has been found associated with NF-κB and pro-inflammatory cytokine response (Guillot et al., 2004; He et al., 2009; Lv et al., 2009; Maes et al., 2006; Villar et al., 2010).

Published reports suggest that the bronchioalveolar lavage pools (extracellular pools) of SP-A are significantly reduced in lungs of infected patients and animal models (Alcorn et al., 2005; Awasthi et al., 1999; Awasthi et al., 2001; Awasthi et al., 2004; Chang et al., 2006; Kajikawa et al., 2005). In contrast, TLR4 expression is increased (Awasthi et al., 2008; Chang et al., 2006; Gagro et al., 2004; Kajikawa et al., 2005). The reduction in the amounts of SP-A, and simultaneous increase in TLR4 expression corroborates well with the clinical condition of patients having fulminant infection and inflammation, respectively. In these clinical scenarios, the introduction of SP-A should facilitate clearance of pathogens and attenuate inflammation. However, currently-available clinical surfactants (used for improving lung function and maturity in pre-term infants) do not contain SP-A or SP-D because it is difficult to mix large hydrophilic SP-A proteins with lipids. As with any large protein, rapid clearance of large proteins, degradation and a non-specific immune response have also hampered the development of clinical surfactant having SP-A.

Inflammatory Bowel Disease (IBD) causes chronic inflammation in the intestine and accounts for a huge economic cost associated with multiple clinic visits and hospitalizations. Therapeutic efficacy with currently recommended drugs has been limited because of toxic effects, nonspecific downregulation of overall immunity and increased risk of infection. Contemporary understanding suggests that activation of Toll-like receptor-4 (TLR4) and TLR4-nuclear factor (NF)-kappa B signaling in the gut causes an overproduction of inflammatory cytokines and trafficking of leukocytes, thus leading to uncontrolled intestinal inflammation. Moreover, persistent inflammation can lead to carcinogenesis. Thus, new therapies targeting TLR4 may be of clinical utility in these conditions.

Interestingly, recently published reports suggested that SP-A directly binds to TLR4 (Guillot et al., 2002; Yamada et al., 2006). However, the in vivo evidence of such an interaction has been lacking, and its functional relevance has not been fully elucidated.

Therefore, there is a need in the art for an understanding of the functional relationship of TLR4 and SP-A, as well as compositions that interact in and/or inhibit said interaction and thereby block TLR4 signaling. It is to said compositions, as well as methods of producing and using same, that the presently disclosed and claimed inventive concept(s) is directed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 illustrates basal TLR4 expression by (A) primary adult baboon lung DCs, (B) KG-1-derived DCs and (C) fetal baboon lung DC-precursor cells under steady-state conditions. Cell-surface expression of TLR4 was detected by flow cytometry after staining the cells with TLR4-specific antibody. The percent number and MFI values of cells stained with TLR4-specific antibody (TLR4) are compared with isotype control antibody-stained cells (I) in selected region (⌐). (D): Western blot showing undetectable expression of TLR4 in 5 µg cell lysate protein of KG-1-derived DCs (KG1-DC). An equal amount of cell lysate protein of HEK293 cells stably transfected with TLR4 (HEK-TLR4) served as positive control.

FIG. 4 depicts the localization of exogenously-added recombinant TLR4-MD2 protein by confocal microscopy and flow-cytometry. Confocal microscopic images of KG-1-derived DCs pulsed with Alexa-fluor 594-conjugated recombinant TLR4-MD2 protein for (A) 1 hour and (B) 4 hours. Vybrant DiO (green) dye stains the cytoplasm, and Hoechst 33342 (blue) dye stains the nucleus of the cell. The images were acquired using 63× objective. (C) Flow-cytometric charts of KG-1-derived DCs pulsed with Alexa-fluor 495-conjugated recombinant TLR4-MD2 protein after 1 hour (dark line) and 4 hours (dotted line). The histogram chart of non-pulsed cells (negative control) is shown under the black area. Cells were gated in M region. Percent number of cells (and MFI values) positive for fluorescence are shown within the chart. Results are representative of two experiments.

FIG. 5 graphically depicts the effect of purified native SP-A, recombinant TLR4-MD2 protein and MD2 protein on phagocytic function of KG-1-derived DCs. (A): Confocal microscopic images of KG-1-derived DCs incubated with pHrodo-labeled *E. coli* bioparticles for 3 hours. Phagocytosed bioparticles fluoresce red. Cells without phagocytosed particles and extracellular bacteria do not fluoresce. Enlarged images of a cell (shown as circle) are also shown in the figure, at different z-stack slices. (B): The extracellular bacteria that are either settled at the bottom or lie towards the top do not emit any fluorescence. These images confirm that fluorescence is of phagocytosed bioparticles. Next, KG-1-derived DCs were incubated with (C): purified baboon lung SP-A (0.2 and 2 µM); (D): recombinant TLR4-MD2 protein (0.06-0.6 µM) and functional-grade anti-human TLR4 antibody (HTA 125 clone, Imgenex, CA; control reaction); (E): recombinant MD2 protein (0.02-0.2 µM); and (F): purified baboon lung SP-A (2 µM) and TLR4-MD2 protein (0.6 µM), for an hour prior to addition of pHrodo-labeled *E. coli* bioparticles. The phagocytic uptake of *E. coli* bioparticles was measured spectrofluorometrically at 550 nm excitation and 600 nm emission wavelengths. Results are mean (SEM) of three different experiments. *$p<0.05$ or ns: not significant as compared to basal phagocytosis.

FIG. 6 graphically depicts the effect of simultaneous addition of purified SP-A and recombinant TLR4-MD2 protein on phagocytic function of primary (A) adult baboon lung DCs and (B) fetal baboon lung DC-precursor cells. The DCs were incubated with respective proteins for an hour prior to addition of pHrodo-labeled *E. coli* bioparticles. The phagocytic uptake of *E. coli* bioparticles was measured spectrofluorometrically. *$p<0.05$, ns: not significant or otherwise indicated. Results are mean (SEM) of three different experiments performed at different times.

FIG. 7 graphically depicts the effect of purified native SP-A and recombinant TLR4-MD2 proteins on TNF-α secretion by DCs against *E. coli*. (A) Primary adult baboon lung DCs or (B) fetal baboon lung DC-precursor cells were incubated with effector molecules for an hour prior to addition of pHrodo-labeled *E. coli* bioparticles. After 3 hours incubation at 37° C. in 5% $CO_2$ incubator, the cell-free supernatants were collected and subjected to ELISA for measurement of TNF-α. The results are representative of two experiments performed separately in triplicate. *$p<0.05$, **$p<0.001$, ns: not significant.

FIG. 9 illustrates (A) Immunoblotting of immunoprecipitates (IP-SP-A and IP-TLR4) with anti-human SP-A (IB-SP-A) and TLR4 (IB-TLR4) antibodies, respectively, to confirm the immunoprecipitation of specific proteins from baboon lung. IP-SP-A, IP-TLR4 and adult baboon lung homogenate protein (40 µg) were run on 8% SDS-PAGE gel under nonreducing (no heating, no DTT) or partially reducing (+heating, no DTT) or reducing (+heating, +DTT) condition. (B) SYPRO-ruby-stained SDS-PAGE gel of IP-SP-A run under partially reducing (+heating, no DTT) condition. Estimated molecular weights of major protein bands are shown within the gel-image. Expected locations of SP-A, TLR4 and MD2 proteins are also marked. (C) Cross-immunoblotting of IP-SP-A and IP-TLR4 with anti-human-TLR4 (IB-TLR4) and SP-A (IB-SP-A) antibodies, respectively. Purified SP-A protein and lysate protein of HEK293 cells stably-transfected with TLR4 (HEK293-TLR4) served as positive control. (D) Negative controls for immunoprecipitation reaction: lanes 1, 2, 9, 10: IP-SP-A and IP-TLR4 immunoblotted with nonspecific primary antibody; lanes 3, 4, 11, 12: IP-SP-A and IP-TLR4 without any antigen or lung tissue homogenate; lanes 5, 6: 1.5 and 1 µl SP-A antibody, respectively; lanes 13, 14: 1.5 and 1 µl TLR4 antibody, respectively; lanes 7, 8, 15, 16: IP reactions in absence of immunoprecipitating antibodies in the columns. The numbers indicate molecular weight (kDa) of standard marker proteins.

FIG. 11 depicts a comparison of SP-A, TLR4 and MD2 amino acid sequences of different animal species. Alignment of amino acid sequences of (A) TLR4, (B) MD2 and (C) SP-A proteins in rat, mouse, baboon, macaca and human. The X-ray crystal structures of human TLR4, human MD2 and rat SP-A available in PDB format were used for bioinformatics simulations (FIGS. 11 and 12). The amino acid residues of SP-A, TLR4 and MD2 included in the bioinformatics simulations are shown (←start, →end). Homology between the proteins of different species is shown as *. FIG. 11A: mouse TLR4, SEQ ID NO:247; rat TLR4, SEQ ID NO:248; baboon TLR4, SEQ ID NO:249; and human TLR4, SEQ ID NO:250. FIG. 11B: macaca MD2, SEQ ID NO:251; human MD2, SEQ ID NO:252; mouse MD2, SEQ ID NO:253; and rat MD2, SEQ ID NO:254. FIG. 11C: rat SP-A, SEQ ID NO:255; mouse SP-A, SEQ ID NO:256; baboon SP-A, SEQ ID NO:257; and human SP-A, SEQ ID NO:1.

FIGS. 19(B) and (C) indicate the purity of synthetic SPA4 peptide (Genscript, CA).

FIG. 29 illustrates that SPA4 peptide inhibits LPS-induced NF-κB activity upstream of MYD88 in dendritic cells. The JAWS II dendritic cells were transfected with either NF-κB-luciferase reporter plasmid DNA alone (NF-κB+MYD88+/+) or co-transfected with MYD88 dominant negative and NF-κB-luciferase reporter plasmid DNAs (NF-κB+MYD88−/−). Transfected cells were then challenged with LPS (100 ng/ml) for 4 hours and treated with SPA4 peptide for an hour. The luciferase activity was measured in cell lysates harvested after 5 hours of total incubation period. The mean luminescence values were normalized with µg total cell lysate protein. Percent change {mean (SEM)} in NF-κB activity relative to LPS treated cells is shown within the bar chart.

FIG. 30 illustrates that SPA4 peptide inhibits endotoxic-shock like symptoms. Mice were challenged with LPS (0.1 microg/g body wt) via intraperitoneal route. Mice were then injected with SPA4 peptide (2.5 microg/g body wt) after 1 hour, 6 hours and 12 hours of LPS challenge or purified lung SP-A (0.5 microg/g body wt) at 1 hour and 6 hours of LPS challenge. The symptoms (Ruffled fur, reactivity, eye exudate, diarrhea, breathing problem) were noted at the scale of 0-3 after 7 hours of LPS challenge. Mean symptom indices (SEM) are shown here for each treatment group.

FIG. 31(A) illustrates that SPA4 peptide inhibits LPS-induced TNF-α. Mice were challenged with LPS (0.1 microg/g body wt) via intraperitoneal route. Mice were then injected with SPA4 peptide (2.5 microg/g body wt) after 1 hour, 6 hours and 12 hours of LPS challenge or purified lung SP-A (0.5 microg/g body wt) at 1 hour and 6 hours of LPS challenge. Mice were sacrificed after 26 hours of LPS challenge. Blood was collected at the time of sacrifice. TNF-alpha levels were measured in serum samples by ELISA method. Mean (SEM) TNF-alpha levels (pg/ml) are shown within each group. FIG. 31(B) illustrates that SPA4 peptide alleviates clinical symptoms in LPS-challenged mice. The time and doses of LPS-challenge and SP-A or SPA4 peptide treatment are shown in flow chart format.

DETAILED DESCRIPTION OF THE INVENTIVE CONCEPT(S)

Figure 1:
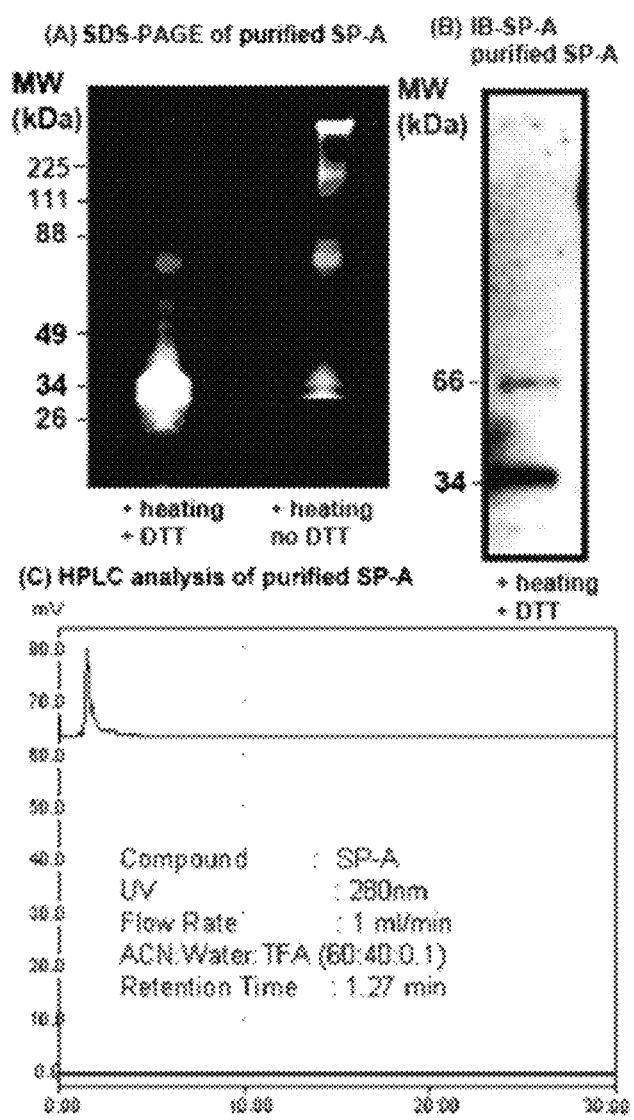
FIG. 1 illustrates the characterization of purified native baboon lung SP-A. (A): Purified baboon SP-A (5 μg in each lane) protein was run under reducing (+heating, +DTT) and partially-reducing (+heating, no DTT) conditions on SDS-PAGE gel and stained. (B): Immunoreactivity of purified SP-A by western blotting with SP-A-specific antibody (IB-SP-A). The SP-A protein was run on reducing SDS-PAGE gel prior to western blotting. (C): HPLC chromatogram of purified lung SP-A.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications and non-patent publications mentioned in the specification are indicative of the level of skill of those skilled in the art to which this presently disclosed and claimed inventive concept(s) pertains. All patents, published patent applications and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" as used herein includes human and veterinary subjects. "Mammal" for purposes of treatment refers to any animal classified as a mammal, including human, domestic and farm animals, nonhuman primates, and any other animal that has mammary tissue.

"Treatment" refers to both therapeutic treatment and prophylactic or preventative measures. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

Administering a therapeutically effective amount or prophylactically effective amount is intended to provide a therapeutic benefit in the treatment, prevention, or management of a disease and/or cancer. The specific amount that is therapeutically effective can be readily determined by the ordinary medical practitioner, and can vary depending on factors known in the art, such as the type of disease/cancer, the patient's history and age, the stage of disease/cancer, and the co-administration of other agents.

A "disorder" is any condition that would benefit from treatment with the polypeptide. This includes chronic and acute disorders or diseases including those pathological conditions which predispose the mammal to the disorder in question.

The terms "cancer" and "cancerous" refer to or describe the physiological condition in mammals that is typically characterized by unregulated cell growth. Examples of include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the inventive concept(s). The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the pharmaceutical compositions of the presently disclosed and claimed inventive concept(s). This concurrent therapy can be sequential therapy, where the patient is treated first with one drug and then the other, or the two drugs are given simultaneously.

The terms "administration" and "administering", as used herein will be understood to include all routes of administration known in the art, including but not limited to, oral, topical, transdermal, parenteral, subcutaneous, intranasal, mucosal, intramuscular, intraperitoneal, intravitreal and intravenous routes, including both local and systemic applications. In addition, the compositions of the presently disclosed and claimed inventive concept(s) (and/or the methods of administration of same) may be designed to provide delayed, controlled or sustained release using formulation techniques which are well known in the art.

The presently disclosed and claimed inventive concept(s) also includes a pharmaceutical composition comprising a therapeutically effective amount of at least one of the compositions described herein in combination with a pharmaceutically acceptable carrier. As used herein, a "pharmaceutically acceptable carrier" is a pharmaceutically acceptable solvent, suspending agent or vehicle for delivering the compositions of the presently disclosed and claimed inventive concept(s) to the human or animal. The carrier may be liquid or solid and is selected with the planned manner of administration in mind. Examples of pharmaceutically acceptable carriers that may be utilized in accordance with the presently disclosed and claimed inventive concept(s) include, but are not limited to, PEG, liposomes, ethanol, DMSO, aqueous buffers, oils, DPPC, lipids, other biologically-active molecules, vaccine-adjuvants, and combinations thereof.

The terms "liposome", "lipid nanostructure" and "vesicle" may be used interchangeably herein and will be understood to refer to an assembled structure constructed of molecules such as lipids and/or proteins, for example, not through covalent bonds but through interactions (such as but not limited to, hydrophobic interactions, electrostatic interactions and hydrogen bonds) acting between the molecules in an aqueous medium.

The terms "aqueous solution" and "aqueous medium" will be used interchangeably herein and will be understood to refer to water as well as any kind of solution which is physiologically acceptable and solvent in water.

The presently disclosed and claimed inventive concept(s) is directed to a composition comprising an isolated peptide that comprises a portion of Surfactant protein A (SEQ ID NO:1 or any of the sequences shown in FIG. 11C). In certain embodiments, the isolated peptide comprises a portion of the C-terminal carbohydrate recognition domain of SPA; in particular embodiments, the isolated peptide comprises the following motif: $NYTX_{3-9}RG$ (SEQ ID NO:2). In addition, the isolated peptide may be less than 50 amino acids in length (such as but not limited to, less than 49, less than 48, less than 47, less than 46, less than 45, less than 44, less than 43, less than 42, or less than 41 amino acids in length). In other embodiments, the isolated peptide may be less than 40 amino acids in length (such as but not limited to, less than 39, less than 38, less than 37, less than 36, less than 35, less than 34, less than 33, less than 32, or less than 31 amino acids in length). In other embodiments, the isolated peptide may be less than 30 amino acids in length (such as but not limited to, less than 29, less than 28, less than 27, or less than 26 amino acids in length). In yet other embodiments, the isolated peptide may be less than 25 amino acids in length (such as but not limited to, less than 24, less than 23, less than 22, or less than 21 amino acids in length). In still further embodiments, the isolated peptide may be less than 20 amino acids in length (such as but not limited to, less than 19, less than 18, less than 17, less than 16, less than 15, less than 14, less than 13, less than 12, less than 11, or less than 10 amino acids in length). In yet still further embodiments, the isolated peptide may be less than 10 amino acids in length (such as but not limited to, less than 9, less than 8, less than 7, less than 6, or less than 5 amino acids in length).

Said compositions of the presently disclosed and claimed inventive concept(s) are capable of binding to Toll-like receptor-4 (TLR-4) and inhibiting TLR-4 signaling pathway(s).

In one embodiment, the isolated peptide may comprise any of SEQ ID NOS:3-7, or a fragment thereof. For example but not by way of limitation, Table 1 lists SEQ ID NOS:8-246, which are exemplary fragments of SEQ ID NOS:3 and 5.

The presently disclosed and claimed inventive concept(s) is also directed to a composition that includes an isolated peptide that is a mutant or derivative of a portion of Surfactant-A-protein and which still retains the ability to bind TLR-4 and inhibit TLR-4 signaling pathway(s). In certain embodiments, the isolated peptide may comprise an amino acid sequence that is at least 80% identical to a portion of SEQ ID NO:1 or 80% identical to any of SEQ ID NOS:3-7. In other embodiments, the isolated peptide may comprise an amino acid sequence that is at least 90% identical to a portion of SEQ ID NO:1 or 90% identical to any of SEQ ID NOS:3-7. In yet other embodiments, the isolated peptide may comprise an amino acid sequence that has 1-5 amino acid changes when compared to a portion of SEQ ID NO:1 or any of SEQ ID NOS:3-7; for example, the isolated peptide may comprise an amino acid sequence that differs from any of SEQ ID NOS: 3-7 by 5 amino acids or less, by 4 amino acids or less, by 3 amino acids or less, by two amino acids or less, or by one amino acid or less.

TABLE 1

| SEQ ID NO: | Amino Acid Sequence |
|---|---|
| 8 | GDFRY |
| 9 | DFRYS |
| 10 | FRYSD |
| 11 | RYSDG |
| 12 | YSDGT |
| 13 | SDGTP |
| 14 | DGTPV |
| 15 | GTPVN |
| 16 | TPVNY |
| 17 | PVNYT |
| 18 | VNYTN |
| 19 | NYTNW |
| 20 | YTNWY |
| 21 | TNWYR |
| 22 | NWYRG |
| 23 | WYRGE |
| 24 | GDFRYS |

TABLE 1-continued

| SEQ ID NO: | Amino Acid Sequence |
|---|---|
| 25 | DFRYSD |
| 26 | FRYSDG |
| 27 | RYSDGT |
| 28 | YSDGTP |
| 29 | SDGTPV |
| 30 | DGTPVN |
| 31 | GTPVNY |
| 32 | TPVNYT |
| 33 | PVNYTN |
| 34 | VNYTNW |
| 35 | NYTNWY |
| 36 | YTNWYR |
| 37 | TNWYRG |
| 38 | NWYRGE |
| 39 | GDFRYSD |
| 40 | DFRYSDG |
| 41 | FRYSDGT |
| 42 | RYSDGTP |
| 43 | YSDGTPV |
| 44 | SDGTPVN |
| 45 | DGTPVNY |
| 46 | GTPVNYT |
| 47 | TPVNYTN |
| 48 | PVNYTNW |
| 49 | VNYTNWY |
| 50 | NYTNWYR |
| 51 | YTNWYRG |
| 52 | TNWYRGE |
| 53 | GDFRYSDG |
| 54 | DFRYSDGT |
| 55 | FRYSDGTP |
| 56 | RYSDGTPV |
| 57 | YSDGTPVN |
| 58 | SDGTPVNY |
| 59 | DGTPVNYT |
| 60 | GTPVNYTN |
| 61 | TPVNYTNW |
| 62 | PVNYTNWY |
| 63 | VNYTNWYR |

TABLE 1-continued

| SEQ ID NO: | Amino Acid Sequence |
|---|---|
| 64 | NYTNWYRG |
| 65 | YTNWYRGE |
| 66 | GDFRYSDGT |
| 67 | DFRYSDGTP |
| 68 | FRYSDGTPV |
| 69 | RYSDGTPVN |
| 70 | YSDGTPVNY |
| 71 | SDGTPVNYT |
| 72 | DGTPVNYTN |
| 73 | GTPVNYTNW |
| 74 | TPVNYTNWY |
| 75 | PVNYTNWYR |
| 76 | VNYTNWYRG |
| 77 | NYTNWYRGE |
| 78 | GDFRYSDGTP |
| 79 | DFRYSDGTPV |
| 80 | FRYSDGTPVN |
| 81 | RYSDGTPVNY |
| 82 | YSDGTPVNYT |
| 83 | SDGTPVNYTN |
| 84 | DGTPVNYTNW |
| 85 | GTPVNYTNWY |
| 86 | TPVNYTNWYR |
| 87 | PVNYTNWYRG |
| 88 | VNYTNWYRGE |
| 89 | GDFRYSDGTPV |
| 90 | DFRYSDGTPVN |
| 91 | FRYSDGTPVNY |
| 92 | RYSDGTPVNYT |
| 93 | YSDGTPVNYTN |
| 94 | SDGTPVNYTNW |
| 95 | DGTPVNYTNWY |
| 96 | GTPVNYTNWYR |
| 97 | TPVNYTNWYRG |
| 98 | PVNYTNWYRGE |
| 99 | GDFRYSDGTPVN |
| 100 | DFRYSDGTPVNY |
| 101 | FRYSDGTPVNYT |
| 102 | RYSDGTPVNYTN |
| 103 | YSDGTPVNYTNW |
| 104 | SDGTPVNYTNWY |
| 105 | DGTPVNYTNWYR |
| 106 | GTPVNYTNWYRG |
| 107 | TPVNYTNWYRGE |
| 108 | GDFRYSDGTPVNY |
| 109 | DFRYSDGTPVNYT |
| 110 | FRYSDGTPVNYTN |
| 111 | RYSDGTPVNYTNW |
| 112 | YSDGTPVNYTNWY |
| 113 | SDGTPVNYTNWYR |
| 114 | DGTPVNYTNWYRG |
| 115 | GTPVNYTNWYRGE |
| 116 | GDFRYSDGTPVNYT |
| 117 | DFRYSDGTPVNYTN |
| 118 | FRYSDGTPVNYTNW |
| 119 | RYSDGTPVNYTNWY |
| 120 | YSDGTPVNYTNWYR |
| 121 | SDGTPVNYTNWYRG |
| 122 | DGTPVNYTNWYRGE |
| 123 | GDFRYSDGTPVNYTN |
| 124 | DFRYSDGTPVNYTNW |
| 125 | FRYSDGTPVNYTNWY |
| 126 | RYSDGTPVNYTNWYR |
| 127 | YSDGTPVNYTNWYRG |
| 128 | SDGTPVNYTNWYRGE |
| 129 | GDFRYSDGTPVNYTNW |
| 130 | DFRYSDGTPVNYTNWY |
| 131 | FRYSDGTPVNYTNWYR |
| 132 | RYSDGTPVNYTNWYRG |
| 133 | YSDGTPVNYTNWYRGE |
| 134 | GDFRYSDGTPVNYTNWY |
| 135 | DFRYSDGTPVNYTNWYR |
| 136 | FRYSDGTPVNYTNWYRG |
| 137 | RYSDGTPVNYTNWYRGE |
| 138 | GDFRYSDGTPVNYTNWYR |
| 139 | DFRYSDGTPVNYTNWYRG |
| 140 | FRYSDGTPVNYTNWYRGE |
| 141 | GDFRYSDGTPVNYTNWYRG |

TABLE 1-continued

| SEQ ID NO: | Amino Acid Sequence |
|---|---|
| 142 | DFRYSDGTPVNYTNWYRGE |
| 143 | YVGLT |
| 144 | VGLTE |
| 145 | GLTEG |
| 146 | LTEGP |
| 147 | TEGPS |
| 148 | EGPSP |
| 149 | GPSPG |
| 150 | PSPGD |
| 151 | SPGDF |
| 152 | PGDFR |
| 153 | YVGLTE |
| 154 | VGLTEG |
| 155 | GLTEGP |
| 156 | LTEGPS |
| 157 | TEGPSP |
| 158 | EGPSPG |
| 159 | GPSPGD |
| 160 | PSPGDF |
| 161 | SPGDFR |
| 162 | PGDFRY |
| 163 | YVGLTEG |
| 164 | VGLTEGP |
| 165 | GLTEGPS |
| 166 | LTEGPSP |
| 167 | TEGPSPG |
| 168 | EGPSPGD |
| 169 | GPSPGDF |
| 170 | PSPGDFR |
| 171 | SPGDFRY |
| 172 | PGDFRYS |
| 173 | YVGLTEGP |
| 174 | VGLTEGPS |
| 175 | GLTEGPSP |
| 176 | LTEGPSPG |
| 177 | TEGPSPGD |
| 178 | EGPSPGDF |
| 179 | GPSPGDFR |
| 180 | PSPGDFRY |

TABLE 1-continued

| SEQ ID NO: | Amino Acid Sequence |
|---|---|
| 181 | SPGDFRYS |
| 182 | PGDFRYSD |
| 183 | YVGLTEGPS |
| 184 | VGLTEGPSP |
| 185 | GLTEGPSPG |
| 186 | LTEGPSPGD |
| 187 | TEGPSPGDF |
| 188 | EGPSPGDFR |
| 189 | GPSPGDFRY |
| 190 | PSPGDFRYS |
| 191 | SPGDFRYSD |
| 192 | PGDFRYSDG |
| 193 | YVGLTEGPSPG |
| 194 | VGLTEGPSPGD |
| 195 | GLTEGPSPGDF |
| 196 | LTEGPSPGDFR |
| 197 | TEGPSPGDFRY |
| 198 | EGPSPGDFRYS |
| 199 | GPSPGDFRYSD |
| 200 | PSPGDFRYSDG |
| 201 | SPGDFRYSDGT |
| 202 | PGDFRYSDGTP |
| 203 | YVGLTEGPSPGD |
| 204 | VGLTEGPSPGDF |
| 205 | GLTEGPSPGDFR |
| 206 | LTEGPSPGDFRY |
| 207 | TEGPSPGDFRYS |
| 208 | EGPSPGDFRYSD |
| 209 | GPSPGDFRYSDG |
| 210 | PSPGDFRYSDGT |
| 211 | SPGDFRYSDGTP |
| 212 | YVGLTEGPSPGDF |
| 213 | VGLTEGPSPGDFR |
| 214 | GLTEGPSPGDFRY |
| 215 | LTEGPSPGDFRYS |
| 216 | TEGPSPGDFRYSD |
| 217 | EGPSPGDFRYSDG |
| 218 | GPSPGDFRYSDGT |
| 219 | PSPGDFRYSDGTP |

TABLE 1-continued

| SEQ ID NO: | Amino Acid Sequence |
|---|---|
| 220 | YVGLTEGPSPGDFR |
| 221 | VGLTEGPSPGDFRY |
| 222 | GLTEGPSPGDFRYS |
| 223 | LTEGPSPGDFRYSD |
| 224 | TEGPSPGDFRYSDG |
| 225 | EGPSPGDFRYSDGT |
| 226 | GPSPGDFRYSDGTP |
| 227 | YVGLTEGPSPGDFRY |
| 228 | VGLTEGPSPGDFRYS |
| 229 | GLTEGPSPGDFRYSD |
| 230 | LTEGPSPGDFRYSDG |
| 231 | TEGPSPGDFRYSDGT |
| 232 | EGPSPGDFRYSDGTP |
| 233 | YVGLTEGPSPGDFRYS |
| 234 | VGLTEGPSPGDFRYSD |
| 235 | GLTEGPSPGDFRYSDG |
| 236 | LTEGPSPGDFRYSDGT |
| 237 | TEGPSPGDFRYSDGTP |
| 238 | YVGLTEGPSPGDFRYSD |
| 239 | VGLTEGPSPGDFRYSDG |
| 240 | GLTEGPSPGDFRYSDGT |
| 241 | LTEGPSPGDFRYSDGTP |
| 242 | YVGLTEGPSPGDFRYSDG |
| 243 | VGLTEGPSPGDFRYSDGT |
| 244 | GLTEGPSPGDFRYSDGTP |
| 245 | YVGLTEGPSPGDFRYSDGT |
| 246 | VGLTEGPSPGDFRYSDGTP |

In certain embodiments of the presently disclosed and claimed inventive concept(s), the composition may include multiple isolated peptides as described herein above.

The presently disclosed and claimed inventive concept(s) further includes a method of producing any of the compositions described herein above. Said method may comprise any of the steps described herein or otherwise known in the art. The compositions of the presently disclosed and claimed inventive concept(s) may be prepared according to methods known in the art, particularly in light of the disclosure and examples set forth herein. The starting materials used to synthesize the compositions of the presently disclosed and claimed inventive concept(s) are commercially available or capable of preparation using methods known in the art.

The presently disclosed and claimed inventive concept(s) also includes an isolated nucleic acid segment encoding any of the compositions described herein above. In addition, a recombinant vector comprising said nucleic acid segment, as well as a recombinant host cell comprising said recombinant vector, are also contemplated within the scope of the presently disclosed and claimed inventive concept(s). In certain embodiments, the recombinant host cell produces the peptide composition.

The presently disclosed and claimed inventive concept(s) is further directed to a pharmaceutical composition comprising any of the isolated peptide compositions described herein above or otherwise contemplated herein, in combination with a pharmaceutically acceptable carrier (or biologically-active molecule or vaccine-adjuvant). In addition, a pharmaceutical composition comprising a nucleic acid segment encoding said peptide composition in combination with a pharmaceutically acceptable carrier is also contemplated in accordance with the presently disclosed and claimed inventive concept(s).

The presently disclosed and claimed inventive concept(s) is also directed to a method of using any of the pharmaceutical compositions described herein above. Said method includes the steps of providing the pharmaceutical composition and administering an effective amount of the pharmaceutical composition to a patient in need thereof.

The presently disclosed and claimed inventive concept(s) is also directed to a method of inhibiting TLR4 signaling. Said method comprises providing any of the isolated peptide compositions described herein above or otherwise contemplated herein, and contacting a cell expressing TLR4 on a surface thereof with said composition, wherein the peptide composition binds to TLR4 on the surface of the cell and inhibits TLR4 signaling by the cell.

The presently disclosed and claimed inventive concept(s) is further directed to a method of decreasing the occurrence and/or severity of inflammation associated with a disease condition. Said method comprises administering an effective amount of a composition (or pharmaceutical composition) as described in detail herein above to a subject suffering from or predisposed to the inflammation/disease condition, thereby decreasing the occurrence and/or severity of inflammation associated with the disease condition in the subject.

Any inflammatory conditions known in the art or otherwise contemplated herein may be treated in accordance with the presently disclosed and claimed inventive concept(s). Non-limiting examples of disease conditions having inflammation associated therewith include infection-related or non-infectious inflammatory conditions in the lung (i.e., sepsis, lung infections, Respiratory Distress Syndrome, bronchopulmonary dysplasia, etc.); infection-related or non-infectious inflammatory conditions in other organs (i.e., colitis, Inflammatory Bowel Disease, diabetic nephropathy, hemorrhagic shock); inflammation-induced cancer (i.e., cancer progression in patients with colitis or Inflammatory Bowel Disease); and the like.

The presently disclosed and claimed inventive concept(s) further include a method of promoting lung development and/or function in infants born pre-term (who are unable to make enough surfactant). Said method comprises administering an effective amount of a composition (or pharmaceutical composition) as described in detail herein above to a subject to promote lung development and/or function and/or maintain immune homeostasis. The composition (or pharmaceutical composition) may be administered alone or in combination with surfactant (i.e., currently available lipid-based clinical surfactants).

EXAMPLES

Examples are provided hereinbelow. However, the present invention is to be understood to not be limited in its application to the specific experimentation, results and laboratory procedures. Rather, the Examples are simply provided as one of various embodiments and are meant to be exemplary, not exhaustive.

Example 1

Surfactant Protein-A and Toll-Like Receptor 4 Modulate Immune Functions of Lung Dendritic Precursor Cells Harvested from Preterm Baboons Preterm infants are highly susceptible to infections; this increased susceptibility to infections is associated with perturbed development and extreme immaturity of the immune system. Antigen-presenting cells have an important role in pathogen-uptake and processing as well as in regulating inflammatory and adaptive host immune responses. Among various types of antigen-presenting cells, dendritic cells (DCs) have been recognized as the most potent (Fajardo-Moser et al., 2008; T. Ohteki, 2007; Sabatte et al., 2007; van Vliet et al., 2007). In the past, several studies have confirmed an immunomodulatory role of lung DCs against a variety of antigens in adult humans and animal models (Banks et al. 1999; Fach et al., 2007; Holt et al., 1995; Lammatzsch et al., 2007; Masten et al., 2006; Webb et al., 2005) with a mature immune system; however, until recently, the phenotypes and functions of lung DCs remained poorly known in preterm babies. The inventor was the first to isolate a unique low-density lung cell population from preterm baby baboons (Awasthi et al., 2009). The results of this study showed that the cells have a density similar to adult baboon lung DCs, are lineage-negative and defective in responding to infectious stimuli. Overall these results suggest that despite having similar isolation characteristics, this unique cell-population harvested from fetal lung does not belong to conventional immature or mature DC categories (Awasthi et al., 2009). Based on these unique properties, they were identified as DC-precursor cells (Awasthi et al., 2009). Recent results from the inventor further demonstrate that the fetal DC-precursor cells express low level of DC-markers, and incubation with DC-promoting cytokines (GM-CSF, IL-4 and TNF-α) induces differentiation of these fetal cells into typical DCs (unpublished results).

The DCs are well known to coordinate innate and adaptive immunity via pathogen-pattern recognition receptors, such as Toll-like receptors (TLR), mannose receptors, scavenger receptors and collections (such as but not limited to, surfactant protein-A (SP-A)) (J. Wright, 2004). Deficiencies or functional defects of pathogen-pattern recognition receptors can negatively affect the DC functions, compromise the host defense and lead to serious consequences in early life-periods of preterm babies. The inventor's previous studies have mainly focused on SP-A, a major part of lung surfactant that lines the alveoli, and TLR4, a potent membrane-receptor that senses both pathogen-associated and damage-associated molecular patterns (PAMP and DAMPs) (Piccinini et al., 2010; and Brown et al., 2010).

The inventor's previous studies observed that the expression of SP-A and TLR4 is undetectable or negligible in lung tissues of fetuses (at 67%-75% of complete gestation term) under steady-state conditions, and increases to the levels equivalent to adult counterparts as the gestation period reaches closer to term (Awasthi et al., 1999; Awasthi et al., 2001; Awasthi et al., 2008). However, preterm birth, mechanical injury (ventilation-associated) and infection significantly influence lung-homeostasis and decrease the alveolar SP-A pools to significantly low levels (Awasthi et al., 1999; Awasthi et al., 2001). In contrast, the expression of TLR4 is increased in preterm babies with lung infections (Awasthi et al., 2008).

To this end, recent understanding in the field suggests that SP-A and TLR4 both enhance phagocytosis. The lack of SP-A in alveoli may compromise the uptake of pathogens. However, an exaggerated activation of TLR4 can lead to chronic inflammatory response or "cytokine storm" (Kramer et al., 2009; Kramer et al.-2, 2009; Sano et al., 2005; J. Blander, 2008; J. Blander, 2007). This pattern correlates well with fulminating infection (low SP-A=low phagocytic uptake) and inflammatory response (increased TLR4=increased amounts of pro-inflammatory cytokines) in preterm babies having lung infection. These results led the inventor to hypothesize that the introduction of SP-A-based clinical surfactants and TLR4-antagonists may compensate for the loss of SP-A and downregulate an exaggerated TLR4-mediated inflammatory response, respectively. It has also been learned recently that SP-A interacts with TLR4 in vitro (Yamada et al., 2006; and Ohya et al., 2006) and in lung (Awasthi et al., 2010). Thus, introduction of SP-A may have an effect on TLR4-mediated immune responses. In this Example, the immunomodulatory effects of native SP-A and recombinant TLR4-MD2 proteins were investigated on selected immune functions (phagocytosis and cytokine response) of fetal baboon lung DC-precursor cells and compared with those of adult baboon lung DCs. The results presented in this Example demonstrate that in both adult and fetal systems, pulsing of cells with SP-A and TLR4-MD2 proteins increases the phagocytic uptake of *Escherichia coli* bioparticles. When added together, no additive effect was demonstrated on phagocytic function of DCs. Co-incubation of cells with SP-A and TLR4-MD2 proteins, however, significantly inhibits the TLR4-MD2-induced release of TNF-α against *E. coli*.

Overall, the results presented in this Example support a significant role of SP-A in improving innate phagocytic function and in suppressing the TLR4-mediated deleterious inflammatory response against infectious stimuli.

Materials and Methods for Example 1:

Baboon lung tissues: The animal studies were approved by Institutional Animal Care and Use Committees, Environmental Health and Safety or Institutional Biosafety Committee of the University of Oklahoma Health Science Center, Oklahoma City, Okla. (OUHSC). Baboon (*P. anubis*) colonies were maintained at Baboon Resources, OUHSC, Oklahoma City, Okla. At the time of necropsy, whole fresh lung or a lobe of lung from fetal (delivered at 125 days of gestation (125 dGA); complete term is 185 dGA) and adult baboons (age range 10-22 years) was collected in RPMI 1640 medium containing 2 mM glutamine, 1 mM N-2-Hydroxyethylpiperazine-N'-2-ethanesulfonic acid (HEPES), 10 µg/ml gentamicin, 100 U/ml penicillin, 100 µg/ml streptomycin and 10% fetal bovine serum (low endotoxin <10EU/ml, FBS; Invitrogen, Carlsbad, Calif.). None of the animals recruited in this study showed any clinical sign of infection or lung pathology. Gross and microscopic examinations of all major viscera and the placenta revealed no signs of inflammation or infection.

Purification of baboon lung SP-A: SP-A was purified from bronchioalveolar lavage fluid of a normal healthy adult baboon by a slight modification of the procedure described previously (Yang et al., 2005). The bronchioalveolar lavage fluid was collected from an adult baboon lung by instilling endotoxin-free, sterile normal saline (endotoxin-free 0.9% NaCl, 1.9-2 L with approximately 90% recovery). The lavage fluid was centrifuged, and the supernatant was concentrated using a tangential flow filtration technique (10 kDa hollow fiber filter; GE Healthcare Bio-Sciences Corp, NJ). The surfactant lipids were removed using isobutyl alcohol (1:5 ratio lavage:isobutyl alcohol). The dilapidated protein was centrifuged at 5,000×g for 15 minutes at room temperature, dried under nitrogen gas, and subsequently completely dried in a lyophilizer (Labconco, MO). The dried lavage residue was rehydrated in extraction buffer (25 mM Tris (pH 7.5), 0.15 M NaCl, and 20 mM octyl-β-D-glucoside) overnight at 4° C. Rehydrated surfactant was extracted six times with extraction buffer by vortex mixing and centrifugation at 20,000×g for 30 minutes at 4° C. Insoluble SP-A was then suspended in solubilization buffer (5 mM HEPES (pH 7.5), 0.02% sodium azide) and dialyzed for 72 hours against four changes of the solubilization buffer. Insoluble protein was removed by centrifugation at 50,000×g for 30 minutes at 4° C., and supernatant was adjusted to 20 mM $CaCl_2$ and 1 M NaCl to re-precipitate SP-A. Precipitated SP-A was pelleted by centrifugation at 50,000×g for 30 minutes at 4° C., and washed two times in 5 mM HEPES (pH 7.5), 20 mM $CaCl_2$ and 1 M NaCl. The SP-A was suspended in 5 mM HEPES, 5 mM EDTA (pH 7.5) and dialyzed for 72 hours against four changes of the solubilization buffer to remove EDTA. The purified SP-A was dialyzed against four changes of the endotoxin-free, highly-purified water (Invitrogen, CA) for 72 hours to remove any remaining EDTA or salts ($CaCl_2$ and NaCl). Finally, purified SP-A was lyophilized completely and resuspended in endotoxin-free Dulbecco's phosphate buffered saline. The purified protein was filter-sterilized using a 0.2 μm low-protein binding, HT Tuffryn membrane filter (Pall Life Sciences, NY) and stored frozen at −80° C. The protein concentration of purified SP-A was measured by microBCA method (Pierce, Ill.).

All the purification steps were performed under aseptic conditions using endotoxin-free solutions and reagents. The endotoxin concentration was measured using the End-point chromogenic *Limulus Amebocyte* Lysate (LAL) assay (Charles River Laboratories, MA). The purity of the SP-A protein was confirmed by SDS-PAGE and Western blotting using the procedures described earlier (Awasthi et al., 1999; Awasthi et al., 2001). The isolated protein was further characterized by high performance liquid chromatography (HPLC) on a Phenomenex C-18 reverse phase column using solvents acetonitrile/water/trifluoroacetic acid (60:40:1) at 1 ml/min, with the UV detector set at 280 nm. The retention time of SP-A was determined to be 1.3 minutes (FIG. 1).

Culture of KG-1-derived DCs and isolation of primary lung DCs: KG-1 cells (Bone marrow myeloblast cells derived from a leukemia patient; ATCC, VA) were cultured in the presence of recombinant human-GM-CSF (100 ng/ml), IL-4 (100 ng/ml) and TNF-α (40 ng/ml) (all the cytokines were purchased from PeproTech, NJ) for a period of 5 days (Ackerman et al., 2003; Bharadwaj et al., 2005; Hulette et al., 2001). The phenotype and morphology of the KG-1-derived DCs were confirmed by flow cytometry and light microscopy, respectively (Awasthi and Cooper, 2006). The KG-1-derived DCs were included as model system to optimize the amounts of effector molecules (purified baboon lung SP-A and recombinant TLR4-MD2 proteins).

Isolation of Adult Baboon Lung DC or Fetal Baboon Lung DC-Precursor Population:

Freshly collected lobe of the lung or whole lung samples of adult and fetal baboons were transported on ice in RPMI 1640 medium containing 2 mM glutamine, 1 mM HEPES, 10 μg/ml gentamicin, 100 U/ml penicillin, 100 μg/ml streptomycin and 10% FBS. After a mild mechanical disruption, the single cell suspension was seeded in a tissue culture flask (Nalge-Nunc International Corp, NY) at a density of 30-50×$10^6$ leukocytes/175 $cm^2$ flask in RPMI 1640 medium containing 2 mM glutamine, 1 mM HEPES, 10 μg/ml gentamicin, 100 U/ml penicillin, 100 μg/ml streptomycin and 10% FBS. The light-density DC-populations were harvested using OptiPrep cell-separation solution (density 1.32 g/ml, Accurate Chemicals, NY) (Awasthi and Cooper, 2006; Awasthi et al., 2009). The immunophenotype and basic characteristics of the lung DC-population isolated from fetal and adult baboons have been described earlier (Awasthi et al., 2009). Here, first the immunophenotype of KG-1-derived DCs and fetal baboon lung DC-precursors or adult baboon lung DCs were compared by flow cytometry. Briefly, cells were suspended in Dulbecco's phosphate buffered saline (DPBS) containing 1% FBS and 0.09% sodium azide and incubated with fluorochrome-conjugated antibodies to HLA-DP, DQ, DR, CD11c, CD40, CD80, CD86 (typical DC-markers) as described earlier.

Expression of endogenous TLR4 by flow-cytometry and western blotting: The harvested cells were suspended in 100 μl DPBS containing 1% FBS and 0.09% sodium azide. Previously titrated phycoerythrinin (PE)-conjugated anti-human TLR4 antibody (BD Biosciences, CA), was added at the ratio of 1 μg antibody per 1×$10^6$ cells. Cells and antibody were incubated for 30 minutes on ice in the dark. The cells were washed three times with PBS containing 1% FBS and 0.09% sodium azide and fixed in freshly prepared 0.5% paraformaldehyde. The cells were run through an automated dual laser excited FACS Calibur at the Flow and Imaging Core Facility (OUHSC, Oklahoma City). The histogram and dot-plot charts were obtained and analyzed using Summit V4.3 software (Dako Colorado Inc, CO). The isotype control antibody-stained cells served as controls for background staining.

For western immunoblotting, whole cell lysates were prepared in lysis buffer (50 mM Tris-HCl, pH 7.4) containing 1% Igepal, 0.25% sodium deoxycholate, 150 mM NaCl, 1 mM EDTA, 1 mM phenyl methyl sulfonyl fluoride (PMSF), and 1 μg/ml each of leupeptin and pepstatin. After protein estimation, about 15 μg of total proteins were fractionated by Novex 4-20% Tris-glycine gradient SDS-PAGE gel (Invitrogen, CA). Separated proteins were electro-transferred onto a nitrocellulose membrane using an iBlot gel transfer device (Invitrogen, CA). The non-specific sites were blocked by incubating the membrane with 7% skim milk in Tris-buffered saline with 0.4% Tween-20 (TBST). The blocked membrane was incubated overnight at 4° C. with monoclonal antibody against TLR4 (clone HTA125; ebioscience, CA) diluted 1:1000 in TBST. The membrane was washed and incubated with horseradish peroxidase (HRP)-conjugated-anti-rabbit-IgG antibody (Sigma-Aldrich, MO) diluted 1:1000 in TBST. The immunoreactive bands were detected by SuperSignal West Femto detection reagent (Thermo Fischer Scientific, IL).

Cellular distribution of exogenously added TLR4-MD2 protein: Since KG-1-derived-DCs, adult baboon lung-DCs and fetal baboon lung DC-precursor cells expressed negligible amounts of TLR4 protein; the cells were pulsed with recombinant human TLR4-MD2 proteins (RnD Systems, MN). The cellular distribution of exogenously-added recombinant TLR4-MD2 protein was investigated by confocal microscopy and flow cytometry.

Labeling of recombinant TLR4-MD2 protein with Alexa-fluor 594 fluorescent dye. Recombinant TLR4-MD2 protein was labeled with Alexa-fluor 594 fluorescent dye using a microscale protein labeling kit (Invitrogen-Molecular Probes, CA) optimized for labeling proteins with molecular weights between 12 and 150 kDa, as per the manufacturer's directions. Briefly, 40 μg of recombinant TLR4-MD2 protein (at the concentration of 1 mg/ml in DPBS) was labeled with Alexa-Fluor 594 carboxylic acid, succinimidyl ester (Excitation/Emission wavelengths: 590/617 nm). The pH of the protein was adjusted to 8.3 using 1/10 volume of 1M sodium bicarbonate, and Alexa-Fluor 594 reactive dye stock solution (12.2 nmol/µl) was added to the protein. The protein:dye mixture was incubated for 15 minutes at room temperature. Fluorochrome-conjugated protein was then separated from unconjugated dye using a spin filter conditioned with gel resin. The spin filter loaded with reaction mixture was centrifuged at 16,000×g for 1 minute. The absorbance of the Alexa-Fluor 594 dye-conjugated TLR4-MD2 protein was read at 280 nm and 590 nm using UV/Vis NanoDrop ND-1000 spectrophotometer (NanoDrop Technologies, DE) and degree of labeling (DOL) was determined using following formula:

$$\text{Protein concentration (mg/mL)} = \frac{[A280 - 0.56(A590)] \times \text{dilution factor}}{A280 \text{ of protein at 1 mg/mL}}$$

$$\text{Protein concentration } (M) = \frac{\text{Protein concentration (mg/mL)}}{\text{Protein molecular weight } (Da)}$$

$$DOL = \frac{\text{(moles dye)}}{\text{(mole protein)}} = \frac{A590 \times \text{dilution factor}}{90,000 \times \text{protein concentration } (M)}$$

Where A280 and A590 are the protein's absorbance at 280 nm and at 590 nm, respectively, the value of 0.56 is a correction factor for the fluorophore's contribution to the A280, and 90,000 cm$^{-1}$M$^{-1}$ is the approximate molar extinction coefficient of the Alexa-Fluor 594 dye.

Cellular distribution of Alexa-fluor 594-conjugated TLR4-MD2 protein by confocal microscopy. The KG-1-derived DCs were seeded at a density of 2.5×10$^5$ cells per well in an S-well chamber slide (Nalge Nunc international, NY) in serum-free Opti-MEM medium (Invitrogen, CA). The cells were then incubated with 10 µg of Alexa fluor 594-conjugated recombinant TLR4-MD2 protein (DOL ~4.0) for 1 hour and 4 hours at 37° C. in 5% $CO_2$ atmosphere. Thirty minutes prior to the completion of incubation period, the Vybrant DiO cell labeling solution (5 nM final concentration, Invitrogen-Molecular Probes, CA) and Hoechst 33342 dye (0.3 µg/ml final concentration, Invitrogen-Molecular Probes, CA) were added to the cells for staining cell-cytoplasm and nucleus, respectively. Finally, the cells were washed twice in Opti-MEM medium, fixed using Vectashield-antifade mounting medium (Vector Laboratories, CA) and observed under Leica TCS SP2 AOBS (Acousto Optical Beam Splitter) multi-photon laser confocal microscope at the Flow and Image Cytometry laboratory (OUHSC, Oklahoma City). Images were acquired with 63× lense objective (at excitation/emission wavelengths: 405/410-550 nm for Hoechst 33342 dye, 488/500-550 nm for DiO dye, and 594/610-660 nm for Alexa-fluor 594 dye) and were analyzed using the Leica TCS software (Leica Microsystems CMS, Mannheim, Germany). Finally, the images acquired were merged and composite pictures were obtained.

Localization of Alexa-fluor 594-conjugated TLR4-MD2 protein by flow cytometry. The KG-1-derived DCs were suspended in Opti-MEM medium at the density of 2.5×10$^5$ cells per 100 µl and incubated with 10 µg Alexa-fluor 594-conjugated recombinant TLR4-MD2 protein. After 1 hour and 4 hours of incubation, cells were washed three times in fresh Opti-MEM medium, re-suspended in 500 µl of 37° C. prewarmed DPBS, and run on Influx Cell Sorter (BD Biosciences, CA) at the Flow and Image Cytometry laboratory (OUHSC, Oklahoma City). The cells were gated to remove debris and histogram charts were obtained at 624-40 nm emission wavelengths. Cell-staining with Alexa-fluor 594-conjugated TLR4-MD2 protein was analyzed using Summit V4.3 software (Dako Colorado Inc, CO).

Phagocytosis assay: In this Example, pHrodo-conjugated, heat-killed E. coli K12 (encapsulated) bioparticles (Invitrogen-Molecular Probes, CA) were employed. The pHrodo-fluorescent label offers an advantage over other conventional methods, in that it fluoresces only in acidic conditions (i.e., after the bioparticles are taken inside the intracellular lysosomes) (Invitrogen-Molecular Probes, CA). To ensure that the fluorescence relates to phagocytosed pHrodo-conjugated E. coli bioparticles only, the phagocytosis reaction mix was imaged by confocal microscopy. Briefly, the KG-1-derived DCs were seeded at a density of 2.5×10$^5$ cells/well in an 8-well chamber slide and incubated with pHrodo-conjugated E. coli K12 bioparticles (one cell-to-~300 bacterial bioparticles) for 3 hours. The Hoechst 33342 dye was added to the cells (0.3 µg/ml final concentration, Invitrogen-Molecular Probes, CA). The cells were washed once, re-suspended in Opti-MEM medium, fixed with Vectashield-antifade mounting medium (Vector Laboratories, CA), and observed under Leica TCS SP2 AOBS (Acousto Optical Beam Splitter) multi-photon laser confocal microscope (at excitation/emission wavelengths: 550/600 nm for pHrodo-labeled bioparticles, 405/410-550 nm for Hoechst 33342 dye) and under brightfield. Images taken at different wavelengths were merged, and composite pictures were obtained.

After confirming that the fluorescence is of phagocytosed bioparticles, comprehensive experiments were performed in presence and absence of effector molecules (SP-A and TLR4-MD2 proteins). The cells were pulsed with purified, native baboon lung SP-A and recombinant human TLR4-MD2 or MD2 proteins (RnD Systems, MN) for an hour prior to phagocytosis assay with pHrodo-conjugated, heat-killed E. coli K12 bioparticles (Invitrogen-Molecular Probes, CA). MD2 protein was also included, because SP-A is known to interact with MD2, and it was questioned if MD2 can influence the immune functions of DC-population. The assay was performed in serum-free Opti-MEM medium (Invitrogen, CA), as described by the manufacturer (Invitrogen-Molecular Probes, CA). The assay mixtures were incubated for another 3 hours at 37° C. in 5% $CO_2$ incubator. The fluorescence readings were taken at 550 nm excitation and 600 nm emission wavelengths using SpectraMax M2 spectrofluorometer (Molecular Devices, CA).

The phagocytosis index was calculated by subtracting the average fluorescence intensity of the reaction with bioparticles alone from the control (basal without any effector molecules) and experimental wells. Finally, the percent effect was calculated using the following formula:

% effect=(Net experimental phagocytosis/Net basal phagocytosis)×100%

The percent phagocytosis of E. coli bioparticles was also confirmed by fluorescence microscopy in representative reaction wells. The cell-free supernatants were collected after taking the fluorometric readings and stored at −80° C. for further analysis.

Cytokine (TNF-α) measurement: The TNF-α levels were measured in cell-free supernatants by enzyme linked immunosorbent assay (ELISA) using a commercially available kit (eBioscience, CA), as per the manufacturer's instructions. Briefly, the microwells of a 96 well plate were coated with diluted purified anti-human TNF-α antibody. The wells were washed, and nonspecific sites were blocked. Diluted recombinant human TNF-α (7.8-500 pg/ml standard) and cell-freesupernatant (1:10) were added to the antibody-coated wells, and the plate was incubated overnight at 4° C. The next day, the plate was washed and incubated with biotin-conjugated anti-human TNF-α antibody followed by avidin-horseradish peroxidase and substrate solution. The reaction was stopped by adding 2 N $H_2SO_4$ and read at 450 nm (Molecular Devices, CA).

Statistical Analysis: The results were analyzed by Student's t-test for statistical significance using Prism software (Graphpad, San Diego, Calif.). $p<0.05$ was considered significant.

Results of Example 1:

The fetal baboon lung DC-population collected from the top of the density gradient were unique to fetal baboons, and were not identified in adult baboons. The morphologic features and phenotypic characteristics have been described in the inventor's publication (Awasthi et al., 2009, the contents of which are expressly incorporated herein by reference).

Figure 2:
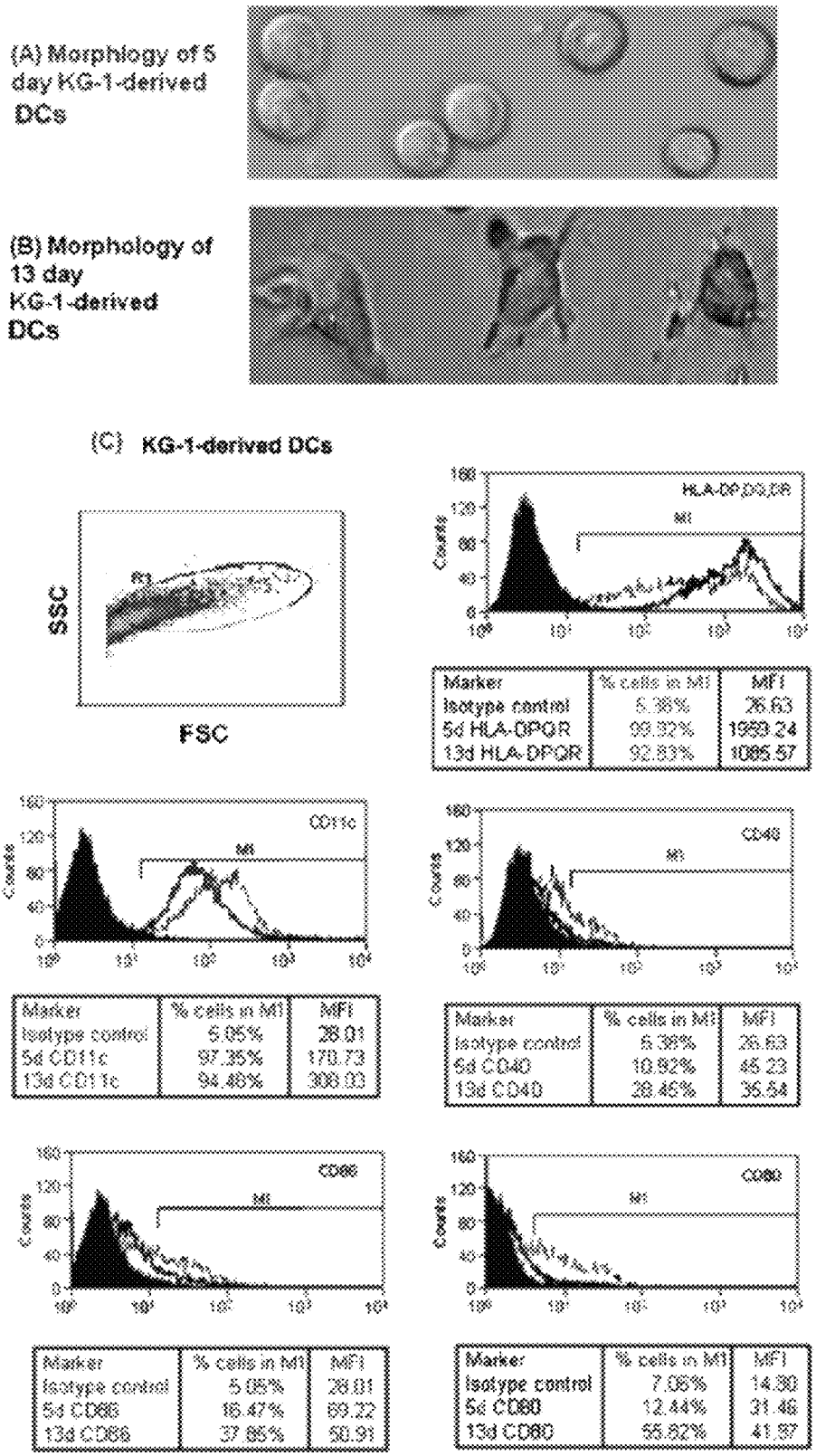
FIG. 2 depicts the morphology and phenotype of human KG-1-cells-derived dendritic cells (DCs), primary adult baboon lung DCs and fetal baboon lung DC-precursor cells. Photomicrographs of wet mount of KG-1-derived DCs after days (A): 5 and (B): 13, of in vitro culture in presence of recombinant human-GM-CSF, IL4 and TNF-α. Flow-cytometric histogram charts of (C): KG-1-derived DCs on days 5 (dark line) and 13 (faded line), (D): adult baboon lung DCs, and (E): fetal baboon lung DC-precursor cells. The cells were stained with DC-markers-specific, fluorescent-conjugated antibodies or isotype control antibody (black area). The cells with high forward scatter (FSC) and side scatter (SSC) were gated, and histogram charts were obtained. The percent number and mean fluorescent intensity (MFI) values of DC-marker positive KG-1-derived DCs are shown in tabulated form. The percent number of primary lung DC or DC-precursor cells positive for DC-markers (DC) is shown within the chart itself. Values shown within parenthesis indicate MFI values. The percent number and MFI values of isotype control (iso) stained cells in M1 region are also shown. The results presented here are representative of at least three experiments.
Figure 2:
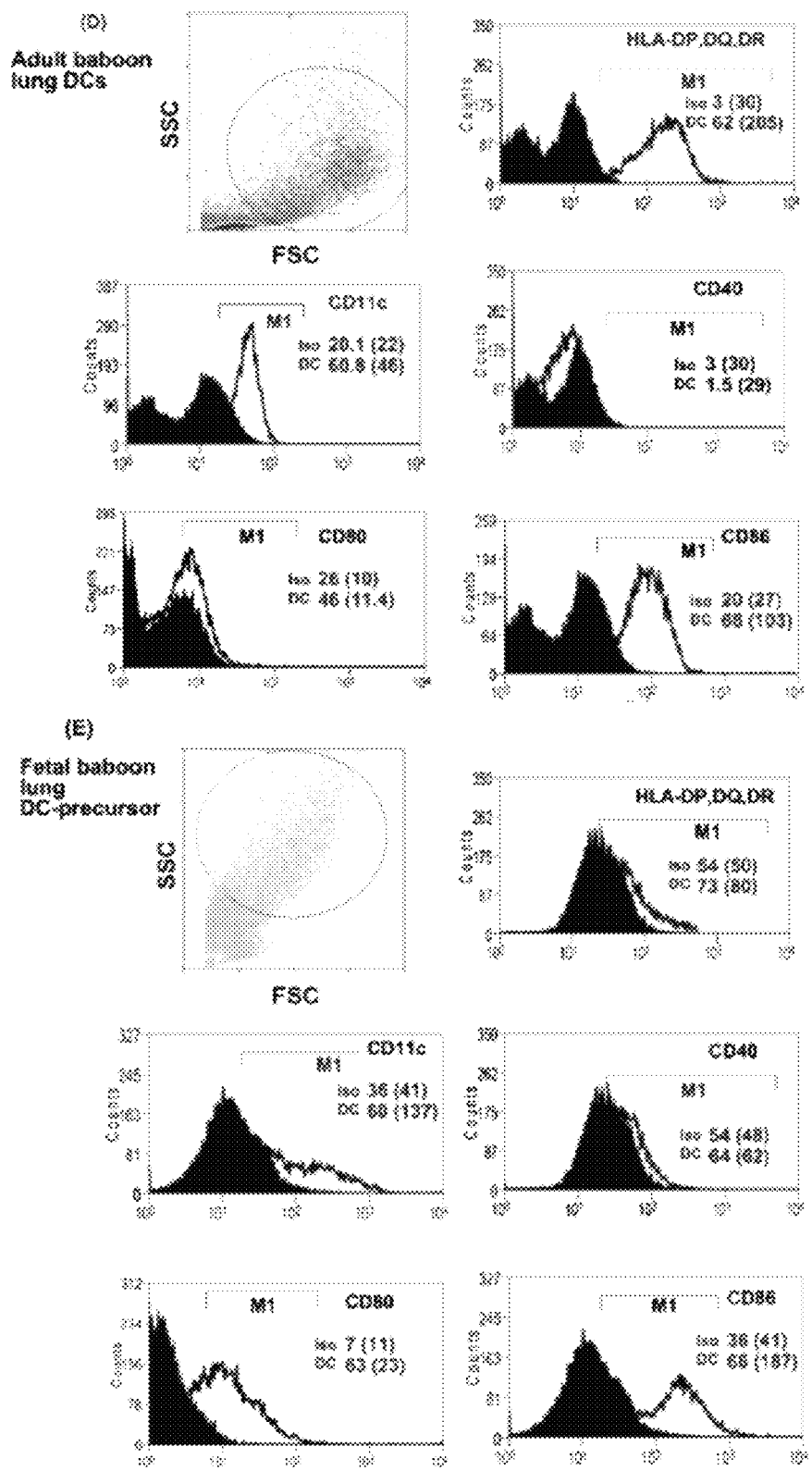

Prior to conducting experiments with adult baboon lung DCs or fetal baboon lung DC-precursor cells, the KG-1-DCs (harvested on 6th day of culture) were used in the initial experiments to optimize the concentration of effector molecules. Morphologically, KG-1-derived DCs harvested on day 5 of culture were round and did not show any tentacles or dendrites (typical of immature DCs). However, after 13 days, the DCs developed dendrites and an irregular shape, characteristic features of mature DCs (FIGS. 2A and B). Flow cytometry analysis of cell-surface-antibody-stained cells showed that KG-1 cells transform into DCs after 13 days and express HLA-DP,DQ,DR, CD11c, CD40, CD80 and CD86 cell-surface markers, characteristics of typical DCs (FIG. 2C). On comparison, it was found that the KG-1-derived DCs express DC-markers to levels similar to those in adult baboon lung DCs (FIGS. 2C and 2D). The fetal baboon lung DC-precursor cells showed negligible levels of DC-markers except CD80 and CD86 (FIG. 2E). Later, primary lung DCs isolated from healthy adult baboons and DC-precursor cells isolated from fetal baboons were used to study the immunomodulatory effects of SP-A and TLR4-MD2 proteins against infectious stimuli.

Characterization of purified native baboon lung SP-A. To elucidate the effects of SP-A, first native SP-A protein was first purified from bronchioalveolar lavage fluid specimens of a normal, healthy adult baboon (Awasthi et al., 1999; Awasthi et al., 2001). The purity and identity of the native baboon lung SP-A was confirmed by SDS-PAGE, western blotting and HPLC. Under partially-reducing conditions (heating and no DTT), SP-A separated as an oligomer, ~100 kDa trimer, and a 66 kDa dimer on the SDS-PAGE gel. Under reducing condition (heating+DTT), SP-A ran as a 32-34 kDa monomer and 66 kDa partially reduced dimer (FIG. 1A). The purified baboon lung SP-A protein was also immunoblotted with SP-A antibody which identified the SP-A-specific protein bands (FIG. 1B). The HPLC chromatogram further confirmed the purity of SP-A (FIG. 1C). Since the TLR4-MD2 proteins are less abundant in the biological system and it is difficult to obtain native TLR4-MD2 protein in sufficient quantity, the recombinant human-TLR4-MD2 protein (RnD Systems, MN) was used. As an adaptor molecule to TLR4, recombinant MD2 protein was also included in the phagocytosis assays.

Since TLR4 is a potent receptor for endotoxin, the presence of endotoxin can significantly influence the results. All of the solutions and reagents were prepared in endotoxin-free water, and all assays were performed in an aseptic environment. Endotoxin concentration was measured in the purified baboon SP-A, and in the reconstituted TLR4-MD2 and MD2 proteins by the chromogenic LAL method (Charles River Lab, MA). The endotoxin concentration was negligible in purified baboon SP-A (0.0003 ng/μg protein) and in recombinant TLR4-MD2 and MD2 protein suspensions (<0.006 ng/μg protein).

KG-1-derived DCs and primary DCs express negligible TLR4 protein under normal conditions; exogenously added TLR4-MD2 protein localizes mainly on the cell surface. The basal cell-surface expression of TLR4 on primary adult baboon lung DCs and KG-1 derived DCs was negligible (FIG. 3). The expression of TLR4 was also undetectable in fetal lung DC-precursor cells (FIG. 3). Thus, DCs were pulsed with recombinant TLR4-MD2 protein prior to the phagocytosis assay. The localization of Alexa-fluor 594-conjugated TLR4-MD2 protein in the KG-1-derived DCs was tracked and studied by confocal microscopy. Confocal images showed that the TLR4-MD2 protein localized mainly on the cell membrane (FIGS. 4A and 4B). Flow-cytometric analysis of DCs pulsed with Alexa-fluor 594-labeled TLR4-MD2 protein showed that there is an increase in MFI values and percent number of cells staining positive for Alexa-fluor 594 stain. These findings further confirmed that the TLR4-MD2 protein localizes on the cell-surface (FIG. 4C).

Exogenous addition of native SP-A and recombinant TLR4-MD2 proteins increases the phagocytic uptake of E. coli bioparticles. In this Example, pHrodo-labeled, heat-killed encapsulated E. coli K12 bioparticles were utilized for investigating the phagocytic ability of DCs. First, the fluorescence of phagocytosed bioparticles in KG-1-derived DCs was confirmed by confocal microscopy. The images showed that only the phagocytosed bioparticles fluoresce (FIG. 5A). In FIG. 5A, a fluorescent cell is focused that has taken up the bioparticles. In contrast, the extracellular bioparticles in the same field, settled at the bottom of the well (z-stack slice #69.8 μm) or floating towards the top (z-stack slice #1.94 μm) do not emit any fluorescence at all (FIGS. 5A and 5B).

In comprehensive phagocytosis experiments, the fluorescence signal reflecting the red fluorescence emitted by phagocytosed pHrodo-labeled E. coli bioparticles, was measured by spectrofluorometry using identical wavelengths setting. Briefly, the KG-1-derived DCs were incubated with purified baboon lung SP-A protein±TLR4-MD2 protein. The % net effect on phagocytosis was calculated in the presence of effector molecules (TLR4-MD2, MD2 and SP-A) after normalizing with the basal phagocytosis in the absence of the effector molecules. The percent phagocytosis calculated by fluorescence microscopy (number of fluorescing cells/total number of cells in a composite of 5 different fields) correlated with the phagocytosis indices calculated by the spectrofluorometry methods. These data demonstrate that both SP-A and TLR4-MD2 proteins increase the phagocytic uptake of E. coli bioparticles by 1.5-2 fold in concentration-dependent manner (p<0.05, FIGS. 5C and 5D). The MD2 protein alone did not affect the phagocytosis (FIG. 5E). Next, the phagocytosis assay was performed with primary lung DC or DC-precursor population in presence of purified SP-A (2 μM) and TLR4-MD2 (0.3 μM) proteins at concentrations that provided maximum phagocytic uptake in KG1-derived DCs (FIGS. 5F and 6). The results demonstrate that, similar to KG-1-derived DCs, the phagocytic uptake of E. coli is increased in the presence of exogenous SP-A (p<0.05) and TLR4-MD2 protein in primary baboon lung DCs. When SP-A and TLR4-MD2 proteins were added together, the phagocytic uptake of E. coli remained increased as compared to basal level; however, no additive effect was observed (FIG. 6).

SP-A reduces the TLR4-MD2 protein-induced TNF-α release against E. coli. TNF-α levels were measured in cell-free supernatants of primary adult baboon lung DCs and fetal baboon lung DC-precursor cells treated with SP-A±TLR4-MD2 proteins after 3 hours of phagocytosis reaction. Addition of purified lung SP-A did not induce the secretion of TNF-α by DCs in response to E. coli, but pulsing with TLR4-MD2 protein increased the TNF-α secretion significantly ($p<0.05$). However, when the SP-A and TLR4-MD2 proteins were added together to the cells and incubated further for another 3 hours with E. coli, the TNF-α levels were equivalent to those incubated without any exogenous protein or with SP-A only (FIG. 7). There was no major difference in responses elicited by DC-populations harvested from adult or fetal baboon lung (FIGS. 7A and 7B), except that the amounts of TNF-α were lower in fetal cells.

Discussion for Example 1

The inventor's results on fetal baboon bone marrow-derived DCs (Awasthi and Cooper, 2006) as well as the reports of others with monocytes (Kramer, 2003) provided evidence that DC functions (i.e., phagocytosis and cytokine secretion) are impaired during prenatal and neonatal periods (Awasthi and Cooper, 2006). However, recent understanding indicates that the tissue-resident DCs are different than the circulating or bone marrow-derived DCs (Diao et al., 2006). Results obtained by the inventor also demonstrate that fetal baboon lung cells are at precursor stage, express negligible levels of DC-markers, and are functionally defective in responding to infectious stimuli (Awasthi et al., 2009; Awasthi and Cooper, 2006). Although the developmental stage of the fetal lung DC-population remains to be completely elucidated in fetal baboons, they have been identified by the inventor as DC-precursor cells because they convert into typical DCs after incubation with DC-promoting cytokines (unpublished data).

One possibility is that since these cells are not fully equipped with TLR or other pathogen-pattern recognition receptors because of developmental immaturity, the DC-precursor cells are not capable of capturing the microorganisms. SP-A also serves as a pathogen-pattern recognition receptor and is known to stimulate DC-maturation and phagocytic uptake of infectious organisms (Kingma and Whitsett, 2006). However, at 125 days of gestation, SP-A is not detectable. NICU care and proper clinical management induce expression of both SP-A and TLR4 which reaches to optimal levels under normal conditions (Awasthi et al., 1999; Awasthi et al., 2001). However, despite an advanced and sophisticated clinical care, preterm babies are more prone to infection, and infection and ventilator-associated lung injury remarkably perturb the expression of SP-A and TLR4. Specifically, lavage pools of SP-A are decreased, and tissue expression of TLR4 is increased. These published results suggest that introduction of SP-A may help maintain the tissue homeostasis and exert anti-infective and anti-inflammatory effects (Lee et al., 2010; Goldmann et al., 2009; Madan et al., 2010; K. Hartshorn, 2010). The present Example was designed to determine if the introduction of SP-A will impact the functions of DCs in the lungs of preterm babies.

The present example was focused on studying selected immune functions: phagocytosis and cytokine secretion against infectious stimuli. Primary cells were pulsed with purified or recombinant protein preparations for two reasons: first, the genetic-transfection of primary DCs will require longer time for efficient protein expression, and longer incubation may induce phenotypic changes in DCs (Brinker et al., 2003); and second, the protein-pulsing mimics the physiological scenario, because both SP-A and TLR4 proteins are known to exist in soluble extracellular, cell surface as well as in intracellular forms under steady-state conditions (Iwami et al., 2000; Ochs et al., 2002). MD2 was also included in conjunction with TLR4, because it serves as an important adaptor molecule to TLR4 and binds to SP-A (Yamada et al., 2006). However, MD2 does not carry an intracellular signaling TIR domain and does not affect the phagocytic function of DCs on its own (FIG. 4). A few investigations have shown that SP-A and TLR4 proteins interact in vitro (Yamada et al., 2006; Ohya et al., 2006). Although the functional relevance of this interaction in fetal or neonatal lungs remains largely unexplored, the results of the present Example demonstrate that SP-A reduces TLR4-MD2-induced cytokine release against infectious stimuli.

The present Example demonstrates that an exogenous addition of SP-A and TLR4-MD2 proteins in the DC population increases phagocytic uptake of encapsulated E. coli (FIGS. 5 and 6). These findings are of clinical importance because encapsulated bacteria resist phagocytosis by antigen-presenting cells and mount an aggressive inflammatory response (Metkar, 2007). It is possible that purified SP-A can also directly kill some of the Gram-negative bacteria by increasing the membrane permeability as reported earlier (Kuzmenko et al., 2005). The SP-A-induced phagocytosis of E. coli bioparticles by DC-precursor cells point towards the importance of SP-A in improving immune functions in preterm babies. Interestingly, SP-A suppresses the TLR4-mediated cytokine release significantly in response to infectious stimuli (FIG. 7). Similar results have been obtained in *Ureaplasma* infection models in an established macrophage cell line RAW 264.7 and in mice (Okogbule-Wonodi et al., 2010; Famuyide et al., 2009). The present Example further supports the role of SP-A in improving the innate immune functions in preterm babies.

The results of this Example are of clinical importance because surfactant preparations currently-used in NICUs do not contain SP-A. Ultimately, this Example supports the idea of reformulating the currently-available clinical surfactant preparations to contain SP-A and their clinical usage in NICU.

Example 2

A Novel TLR4-Interacting Surfactant Protein-A-Derived Peptide Suppresses LPS-Induced TLR4 Expression and TNF-α Release Published reports suggest that the bronchioalveolar lavage pools (extracellular pools) of SP-A are significantly reduced in lungs of infected patients and animal models (Alcorn et al., 2005; Awasthi et al., 1999; Awasthi et al., 2001; Awasthi et al., 2004; Chang et al., 2006; Kajikawa et al., 2005). In contrast, the TLR4 expression is increased (Awasthi et al., 2008; Chang et al., 2006; Gagro et al., 2004; Kajikawa et al., 2005). The reduction in the amounts of SP-A, and simultaneous increase in TLR4 expression corroborates well with the clinical condition of patients having fulminant infection and inflammation, respectively. In these clinical scenarios, the introduction of SP-A should facilitate clearance of pathogens and attenuate inflammation. However, currently-available clinical surfactants do not contain SP-A or SP-D. Thus, a great need has been felt for designing a shorter fragment of SP-A as well as reformulating the surfactant.

Interestingly, recently published reports suggested that SP-A directly binds to TLR4 (Guillot et al., 2002; Yamada et al., 2006). The in vivo evidence of such an interaction has been lacking, and its functional relevance has not been fully elucidated. In this Example, the binding of SP-A to TLR4-MD2 in non-infected, normal baboon lung tissues was determined by co-immunoprecipitation/immunoblotting, and in vitro by a microwell-based method. Next, a bioinformatics approach was used to examine the interaction between SP-A and TLR4-MD2 proteins. In conjunction, potential binding regions were identified in an in silico model of the SP-A-TLR4-MD2 complex. Based on the information obtained from the bioinformatics analysis, an SP-A-derived peptide library was synthesized. Studies were further extended to investigate the functional relevance of SP-A-TLR4 interaction in a dendritic cell system. The present Example demonstrates that similar to native SP-A, an SP-A-derived peptide (SPA4; SEQ ID NO:3) binds to TLR4-MD2 protein, inhibits expression of TLR4 and reduces the release of TNF-α in response to the most potent TLR4-ligand: Gram-negative bacteria-derived lipopolysaccharide (LPS).

Materials and Methods of Example 2:

Animals: The animal studies were approved by the Institutional Animal Care and Use and Institutional Biosafety Committees at the University of Oklahoma Health Science Center (OUHSC), Oklahoma City, Okla. Baboons (*Papio anubis*) were maintained at the Baboon Research Resource, OUHSC, Oklahoma City, Okla. At the time of necropsy, lung tissue or bronchioalveolar lavage fluid specimens were obtained from normal healthy adult baboons. Gross and microscopic examinations of major viscera as well as the lung tissue specimens from these baboons showed no signs of inflammation or infection.

Preparation of baboon lung tissue homogenate: The frozen lung tissue samples were homogenized in a buffer containing 1% Igepal CA630, 0.1% sodium dodecyl sulfate, and protease inhibitors (1 µM leupeptin, 1 mM ethylenediamine tetraacetic acid, 0.7 mg/L pepstatin and 0.2 mM phenylmethyl sulphonyl fluoride; Sigma-Aldrich, MO) at a concentration of 100 mg tissue/ml buffer (Awasthi et al., 1999; Awasthi et al., 2001). The tissue homogenates were centrifuged to remove cell debris, and total protein concentration was measured in supernatants using the MicroBCA protein estimation kit (Pierce, IL).

Western blotting: The inventor has recognized the cross-reactivity of anti-human-SP-A- and anti-human-TLR4-antibodies with respective antigens in baboons, and studied the expression of SP-A and TLR4 in lung tissue homogenates of fetal and adult baboons, and neonate baboons having Bronchopulmonary dysplasia (Awasthi et al., 1999; Awasthi et al., 2008). Here, using western blotting, the immunoreactivity of these antibodies with respective antigens was first confirmed in baboon lung tissue homogenates to ensure the integrity of the antigens. Lysates of HEK-293 cells stably-transfected with human-TLR4-cDNA (provided by Invivogen, CA), and purified human- and baboon-lung SP-A proteins served as positive controls.

The protein samples were prepared in SDS-PAGE sample buffer without dithiothreitol (DTT)+no heating (non-reducing), without DTT+heating at 100° C. for 5 minutes (partially-reducing) or with DTT+heating at 100° C. for 5 minutes (reducing). The samples were loaded and separated on a SDS-PAGE gel (8% running and 5% stacking gel or Novex 4-20% Tris-glycine gel, Invitrogen, CA). Separated proteins were then electro-transferred overnight onto a nitrocellulose membrane. The nonspecific sites were blocked by incubating the membrane in 7% skim milk diluted in Tris-buffered saline containing 0.4% Tween 20 (TBST). The membranes were then incubated with anti-human-SP-A polyclonal antibody (Awasthi et al., 1999; Awasthi et al., 2001) or TLR4 antibody (eBioscience, CA) (Awasthi et al., 2008), diluted 1:1000 in TBST, for 1 hour at room temperature. The membrane was washed and then incubated with horseradish peroxidase (HRP)-conjugated-anti-mouse or anti-rabbit IgG antibody (1:1000 diluted in TBST; Sigma-Aldrich, MO). The immunoreactive bands were detected by Supersignal West Pico or Femto chemiluminescent substrate (Pierce, IL).

Immunoprecipitation of lung-SP-A or TLR4 and cross-immunoblotting: After confirming the reactivity of the antibodies and the integrity of TLR4 and SP-A proteins in baboon lung tissue homogenates, the physical binding between the two proteins was examined by immunoprecipitation/cross-immunoblotting. The SP-A and TLR4 proteins were immunoprecipitated from baboon lung tissue homogenates and cross-immunoblotted with anti-human-TLR4 and SP-A antibodies, respectively. The SP-A (IP-SP-A) and TLR4 (IP-TLR4) were immunoprecipitated using Primary Seize Immunoprecipitation kit (Pierce, IL) as per the manufacturer's instructions. Approximately 200 µg of anti-human-TLR4 or SP-A antibody (Awasthi et al., 2001; Awasthi et al., 2008) was conjugated to the AminoLink plus coupling gel column at 4° C. overnight. Five hundred µg to 1 mg of total lung tissue homogenate protein was loaded into the columns and the immunoprecipitation reaction was performed overnight at 4° C. The IP-SP-A and IP-TLR4 were eluted from the antibody-bound column using ImmunoPure elution buffer. No Calcium was added to the immunoprecipitation reaction at any step. Also, none of the buffers in the kit contained calcium.

Various amounts of IP-TLR4 and IP-SP-A were run on SDS-PAGE gels. The separated proteins were then transferred on nitrocellulose membrane using the i-Blot system (Invitrogen, CA). For cross-immunoblotting, IP-SP-A and IP-TLR4 were immunoblotted with anti-TLR4 and anti-SP-A antibodies, respectively, as described above. Positive controls included lung tissue homogenate protein, purified human SP-A and lysate-protein of HEK-293 cells-transfected with full-length, human-TLR4-cDNA. Negative controls included IP-SP-A and IP-TLR4 immunoblotted with a non-specific antibody, and immunoprecipitates from columns where the lung tissue homogenate or the primary antibody had been omitted.

Purification and characterization of native Baboon SP-A: SP-A was purified from bronchioalveolar lavage fluid of an adult baboon by a modification of the procedure described previously (Yang et al., 2005). The bronchioalveolar lavage fluid was collected from an adult baboon lung by instilling endotoxin-free, sterile normal saline (endotoxin-free 0.9% NaCl, 1.9-2 L with approximately 90% recovery). The lavage fluid was centrifuged, and the supernatant was concentrated using a tangential flow filtration technique (10 kDa hollow fiber filter; GE Healthcare Bio-Sciences Corp, NJ). The surfactant lipids were removed using isobutyl alcohol (1:5 ratio lavage:isobutyl alcohol). The dilapidated protein was centrifuged at 5000×g for 15 minutes at room temperature, dried under nitrogen gas, and subsequently completely dried in a lyophilizer (Labconco, MO). The dried lavage residue was rehydrated in extraction buffer (25 mM Tris, pH 7.5, 0.15 M NaCl, and 20 mM octyl-β-D-glucoside) overnight at 4° C. Rehydrated surfactant was extracted six times with extraction buffer by vortex mixing and centrifugation at 20,000×g for 30 minutes at 4° C. Insoluble SP-A was then suspended in solubilization buffer (5 mM HEPES, pH 7.5, 0.02% sodium azide) and dialyzed for 72 h against four changes of the solubilization buffer. Insoluble protein was removed by centrifugation at 50,000×g for 30 minutes at 4° C., and supernatant was adjusted to 20 mM $CaCl_2$ and 1 M NaCl to re-precipitate SP-A. Precipitated SP-A was pelleted by centrifugation at 50,000×g for 30 minutes at 4° C., and washed two times in 5 mM HEPES pH 7.5, 20 mM $CaCl_2$ and 1 M NaCl. The SP-A was suspended in 5 mM HEPES, 5 mM EDTA, pH 7.5 and dialyzed for 72 h against four changes of the solubilization buffer to remove EDTA. The purified SP-A was dialyzed against four changes of endotoxin-free, highly-purified water (Invitrogen, CA) for 72 h to remove any remaining EDTA or salts (CaCl$_2$ and NaCl). Finally, purified SP-A was lyophilized completely and resuspended in endotoxin-free Dulbecco's phosphate buffered saline. The purified protein was filter-sterilized using a 0.2 μm low-protein binding, HT Tuffryn membrane filter (Pall Life Sciences, NY) and stored frozen at −80° C. The protein concentration of purified SP-A was measured by microBCA method (Pierce, IL).

All the purification steps were performed under aseptic conditions using endotoxin-free solutions and reagents. The endotoxin concentration was measured using the End-point chromogenic *Limulus Amebocyte* Lysate (LAL) assay (Charles River Laboratories, MA). The purity of the SP-A protein was confirmed by SDS-PAGE and Western blotting using the procedures described above.

Interaction between purified baboon lung SP-A, SP-A-peptides and TLR4-MD2 proteins using a microwell-based method: The binding between the purified baboon lung SP-A, SP-A-peptides and recombinant TLR4-MD2 and MD2 proteins was studied in vitro using a microwell-based method (Awasthi et al., 2004). The soluble, recombinant TLR4-MD2 protein (R&D Systems, MN) consisted of a mixture of recombinant human-TLR4 and MD2 proteins. The recombinant extracellular domain of human TLR4 protein (Glu 24-Lys 631 amino acids), was joined with a DNA sequence encoding the signal peptide from human CD33 and a 10× histidine tag at the C-terminus (Accession # O00206). For MD2 protein, a DNA sequence encoding the signal peptide from human CD33 was joined with the mature region of human MD-2 (mature region, Glu 17-Asn 160 amino acids) and a 10× histidine tag at the C-terminus (Accession # Q9Y6Y9). The chimeric proteins were expressed in a mouse myeloma cell line, NS0 (R&D Systems, MN). The proteins were obtained from the manufacturer in carrier-free condition and reconstituted in PBS containing 0.1% low-endotoxin BSA (MP Biomedicals, OH). MD2, an adaptor molecule for TLR4, is expressed by immune cells, and is known to bind TLR4 in a non-covalent manner (Jain et al., 2008). Thus, the binding of SP-A to the recombinant MD2 protein (R&D Systems, MN) was also studied.

For the binding assay, microwell ultra-high-protein binding Immunolon 4HBX strips (Thermo Scientific, MA) were coated with soluble recombinant-TLR4-MD2 protein or MD2 protein (R&D Systems, 250 ng per well, diluted in 0.1 M NaHCO$_3$, pH 9.6) overnight at room temperature. The plates were washed three times, and non-specific sites were blocked for 2 h at room temperature using phosphate buffered saline containing 0.1% triton-X 100 and 3% nonfat milk (Buffer A). The wells were washed and incubated for 3 h at 37° C. with purified baboon lung SP-A (0.125-10 μg), SPA4 peptide (2-20 μg; SEQ ID NO:3) or adult baboon lung tissue homogenate protein (10-100 μg) diluted in 20 mM Tris (pH 7.4) buffer containing 0.15 M NaCl, 5 mM CaCl$_2$ or equal amount of bovine serum albumin (BSA) protein. The wells were washed with Buffer A and incubated with anti-human SP-A antibody (1:1000 diluted in Buffer A) for 2 h at room temperature followed by HRP-conjugated secondary antibody. The immune-complex was detected using 3,3',5,5'-tetramethylbenzidine (TMB) substrate system (Sigma-Aldrich, MO). The reaction was stopped with 2 N H$_2$SO$_4$ and read at 405 and/or 450 nm spectrophotometrically (Molecular Devices, CA).

JAWS II dendritic cell culture: The JAWS II dendritic cell line is an immortalized cell line derived from bone marrow of C57BL/6 mice (ATCC, Manassas, Va.). The cells were maintained in Alpha-modified minimum essential medium (Sigma, St Louis, Mo.) supplemented with 20% fetal bovine serum (FBS), 4 mM L-glutamine, 100 U/ml penicillin, 100 μg/ml streptomycin, 50 μg/ml gentamicin (Invitrogen, Grand Island, N.Y.) and 5 ng/ml of recombinant murine granulocyte macrophage-colony stimulating factor (Peprotech, Rocky Hill, N.J.). (Awasthi et al., 2005). The culture medium was replaced with fresh medium every 48 h.

Figure 8:
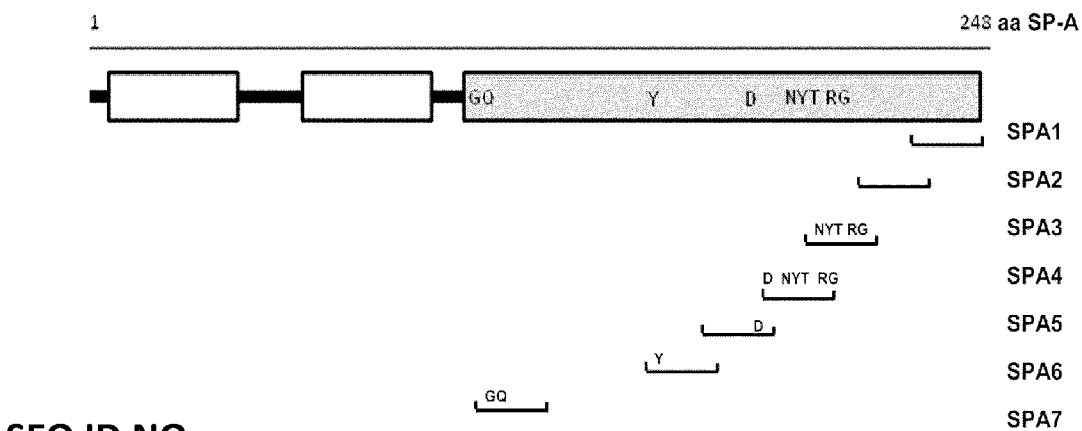
FIG. 8 illustrates the synthetic peptides derived from C-terminal CRD region of human-SP-A. The peptides sequences and their location in SP-A are shown within the figure. Underlined amino acids were recognized at the interface of SP-A-TLR4 complex in the in silico analysis (FIGS. 12 and 14).

LPS treatment of JAWS II dendritic cells with and without SP-A peptides: Based on the results of the bioinformatics analysis (described in Results section), SP-A peptides (SPA1 SEQ ID NO:258); SPA2 SEQ ID NO:259); SPA3 SEQ ID NO:4); SPA4 (SEQ ID NO:3); SPA5 (SEQ ID NO:5); SPA6 SEQ ID NO:260); and SPA7 SEQ ID NO:261) were synthesized. The amino acid sequences were derived from the C-terminal Carbohydrate Recognition Domain (CRD) of human SP-A corresponding to the TLR4-interacting sites identified in the in silico model of SP-A-TLR4-MD2 complex (FIG. 8). The 20-mer peptides were synthesized by Genscript Corp, NJ; and Mass Spectroscopy and HPLC analyses confirmed the characteristics and purity of synthesized peptides, respectively (data not shown). LAL test (Charles River Lab, MA) confirmed the absence of endotoxin in the peptide samples.

In Example 1, it was demonstrated that short-pulsing of baboon lung dendritic cells with purified lung SP-A and recombinant TLR4-MD2 protein leads to TLR4-induced cytokine release against *E. coli*. Thus, it was questioned if the SP-A-derived peptides from the TLR4-interacting regions will demonstrate a similar effect. The JAWS II dendritic cells (1 million) were treated with SP-A peptides (1 or 10 μM) with or without *E. coli* derived LPS (75 ng/ml, highly purified, low protein, Calbiochem, CA). In order to observe the anti-inflammatory properties of the SP-A peptides, the cells were treated with peptides for 1 hour prior to addition of LPS (pre-LPS treatment) or after 4 hours incubation with LPS (Post-LPS treatment). The incubation was continued for a total period of 5 hours. Control cells were treated with vehicle, LPS (75 ng/ml), and/or SP-A peptides (1 and 10 μM) for a period of 5 hours. The cell-free supernatants were collected and stored at −80° C. for further analysis.

TLR4 expression by immunocytochemistry: The JAWS II-DCs were seeded at a density of 25,000 cells per well of an 8-well chamber slide (Nalge Nunc international, New York, USA). Post-LPS (100 ng/ml) treatment with SPA4 peptide (1 and 10 μM; SEQ ID NO:3) followed, and the cells were fixed for 20 minutes with 3.5% paraformaldehyde prepared in PBS on ice. Permeablization was carried out for 20 minutes on ice with Alpha-MEM medium containing 10% FBS and 0.05% saponin and 10 mM HEPES (Inaba et al., 1998). The cells were washed with PBS supplemented with 1% FBS and 0.05% saponin (wash buffer). Non-specific binding sites were blocked using PBS containing 10% normal mouse serum (Sigma, St Louis, Mo.) for 1 hour at room temperature in a humidified chamber. A rabbit polyclonal antibody to mouse TLR4 (Abcam, Cambridge, Mass.) was added to the cells at a dilution of 1:50 and incubated overnight at 4° C. in a humidified chamber. The cells were washed three times for 5 minutes each, followed by incubation with 10 μg/ml Alexa Fluor 488-labeled donkey anti-rabbit IgG antibody (Molecular Probes, Carlsbad, Calif.) for 1 hour at room temperature in humidified chamber protected from light. The cells were incubated with 100 nM rhodamine-phalloidin (Cytoskeleton Inc, Denver Colo.) for 30 minutes at room temperature. Finally, 1 μg/ml Hoechst 3342 (Molecular Probes, Carlsbad, Calif.) dye was added to the cells. Confocal microscopic images were acquired at Imaging and core facility of Oklahoma Medical Research Foundation using the Zeiss LSM- 510META laser scanning confocal microscope. Images were acquired with lens objective of 63× with the x/y stack sizes being 146.2 µm using band pass filter specifications at 435-485, 560-615 and 505-530.

Cytokine (TNF-α) measurement: The TNF-α levels were measured in cell-free supernatants of JAWS II dendritic cells treated with LPS with or without SP-A peptides by enzyme linked immunosorbent assay (ELISA) as described earlier (Awasthi and Cox, 2003).

Statistical analysis: The results were analyzed by the Student t-test or ANOVA for statistical significance using Prism software (Graphpad, San Diego, Calif.). At $p<0.05$, the null hypothesis was rejected.

Results of Example 2

TLR4 and SP-A co-immunoprecipitated from baboon lung tissue homogenates. The inventor has previously shown that human-SP-A and TLR4-specific antibodies react with baboon-SP-A and TLR4 proteins, respectively (Awasthi et al., 1999; Awasthi et al., 2001; Awasthi et al., 2008). Using the same antibody clones, the integrity of SP-A and TLR4 was confirmed in baboon lung tissue homogenates. The immunoprecipitation of specific proteins was identified by immunoblotting the IP-SP-A and IP-TLR4 eluates from adult baboon lung tissue homogenates using SP-A- and TLR4-specific antibodies, respectively (FIG. 9A). The SDS-PAGE gel run of concentrated IP-SP-A showed additional protein bands besides SP-A, suggesting a number of SP-A-binding proteins (FIG. 9B). The lung tissue homogenate protein, lysate protein of HEK293 cells stably-transfected with full-length TLR4, and purified SP-A protein were run simultaneously as positive controls to confirm the identity of the IP-SP-A and IP-TLR4. The sizes of the TLR4 and SP-A protein bands corresponded to the respective proteins in baboon lung tissue homogenates, as published earlier (Awasthi et al., 1999; Awasthi et al., 2001; Awasthi et al., 2008). Neither SP-A nor TLR4 was immunoprecipitated when a nonspecific antibody was used in the column (data not shown).

Next, it was hypothesized that if the SP-A and TLR4 proteins interact with each other, the two proteins may exist together in the lung and may be co-immunoprecipitated from lung tissue homogenates. The cross-immunoblotting results indicate that SP-A and TLR4 are co-immunoprecipitated from baboon lung specimens (FIG. 9C). A major protein band of >100 kDa was identified in both IP-TLR4 and IP-SP-A when the IP-eluates were separated on a partially-reducing SDS-PAGE gel and cross-immunoblotted. Protein bands of 34 kDa (similar to SP-A monomer) and 66 kDa (SP-A dimer) were identified when IP-TLR4 was separated on a reducing SDS-PAGE gel and immunoblotted with anti-SP-A antibody (FIG. 9C). A protein band of 55 kDa (TLR4) was recognized when IP-SP-A was separated on reducing SDS-PAGE gel and immunoblotted with anti-TLR4 antibody (FIG. 9C). The specificity of the immunoprecipitation reaction was validated using appropriate negative controls (FIG. 9D). These results demonstrated that the IP-TLR4- and IP-SP-A-eluates did not contain any noon-specific protein or antibody fractions.

Characterization of purified native baboon lung SP-A: To further elucidate the interaction between SP-A and TLR4, native SP-A protein was first purified from bronchioalveolar lavage fluid specimens of a normal, healthy adult baboon (Awasthi et al., 1999; Awasthi et al., 2001). The purity and identity of the native baboon lung SP-A was confirmed by SDS-PAGE and western blotting. Under partially-reducing conditions (heating and no DTT), SP-A separated as an oligomer, a 90 kDa-100 kDa trimer, and a 66 kDa dimer on the SDS-PAGE gel. Under reducing conditions (heating+DTT), SP-A ran as a 32-34 kDa monomer and a 66 kDa partially reduced dimer. The purified baboon lung SP-A protein was also immunoblotted with SP-A antibody which identified the SP-A-specific protein bands. The solubility of purified baboon lung SP-A was 51% (Stenvall et al., 2005). Since the TLR4-MD2 proteins are less abundant in biological systems and distributed throughout, it is difficult to obtain native TLR4-MD2 protein in sufficient quantity. Thus, recombinant human-TLR4-MD2 protein (RnD Systems, MN) was included.

Since TLR4 is a potent receptor for endotoxin, the presence of endotoxin can significantly influence the results. Thus, all solutions and reagents were prepared in endotoxin-free water, and all assays were performed in an aseptic environment. Endotoxin concentration was measured in the purified baboon SP-A preparation and in the reconstituted TLR4-MD2 and MD2 proteins by the chromogenic LAL method. The endotoxin concentration was negligible in purified baboon SP-A (0.0003 ng/µg protein) and in recombinant TLR4-MD2 and MD2 protein suspensions (≤0.006 ng/µg protein).

Lung SP-A and recombinant TLR4-MD2 proteins interact in vitro. The surface-bound TLR4-MD2 and MD2 proteins showed binding with purified baboon lung SP-A and SP-A protein present in native form in lung tissue homogenate (FIGS. 10A and 10B). Purified baboon lung SP-A was also found to bind to surface-bound MD2 protein (FIG. 10C). In comparison, BSA (negative control) showed negligible binding to the TLR4-MD or MD2 protein.

Protein-protein docking and prediction of interacting amino acids at the interface of SP-A-TLR4-MD2 protein complex. In previous sections, the interaction between SP-A and TLR4-MD2 proteins was experimentally characterized. In this section, the bioinformatics approaches used to examine the interaction are described. First it is described how data was obtained for bioinformatic analyses; then, the in silico docking of SP-A with TLR4-MD2 is described, followed by a description of the rendering of the docking interface.

SP-A structure: Under physiological conditions, SP-A exists as an octadecamer comprising 6× trimer units (Palaniyar et al., 2000), and TLR4-MD2 exists as a dimer (Park et al., 2009). The trimeric crystal structure of neither the human SP-A nor the baboon SP-A is available in the protein data bank (PDB, www.rcsb.org/pdb) (Berman et al., 2000). Head et al., (2003) solved the crystal structure of the trimeric carbohydrate recognition domain/neck domain of SP-A. However, the PDB file and X-ray structure in the protein data bank were available for the monomeric subunit of rat SP-A (PDB ID:1R13) (Head et al., 2003). Using bioinformatics approaches, it is possible to obtain the structure of trimer by docking three monomers to form a single complex. SymmDock (Schneidman-Duhovny et al., 2005a; b), an automated server that deduces the structure of homomultimer with cyclic symmetry when the structure of a monomeric subunit is available, was used for the above task. SymmDock server returned 100 possible trimer complexes that differed in the arrangement of monomers, accompanied by a priority score. Of all the configurations returned by the server, only the top scoring complex was identical to the structure of the trimer shown in the prior art (Head et al., 2003; Palaniyar et al., 2000), and the rest had different arrangements.

Figure 11:
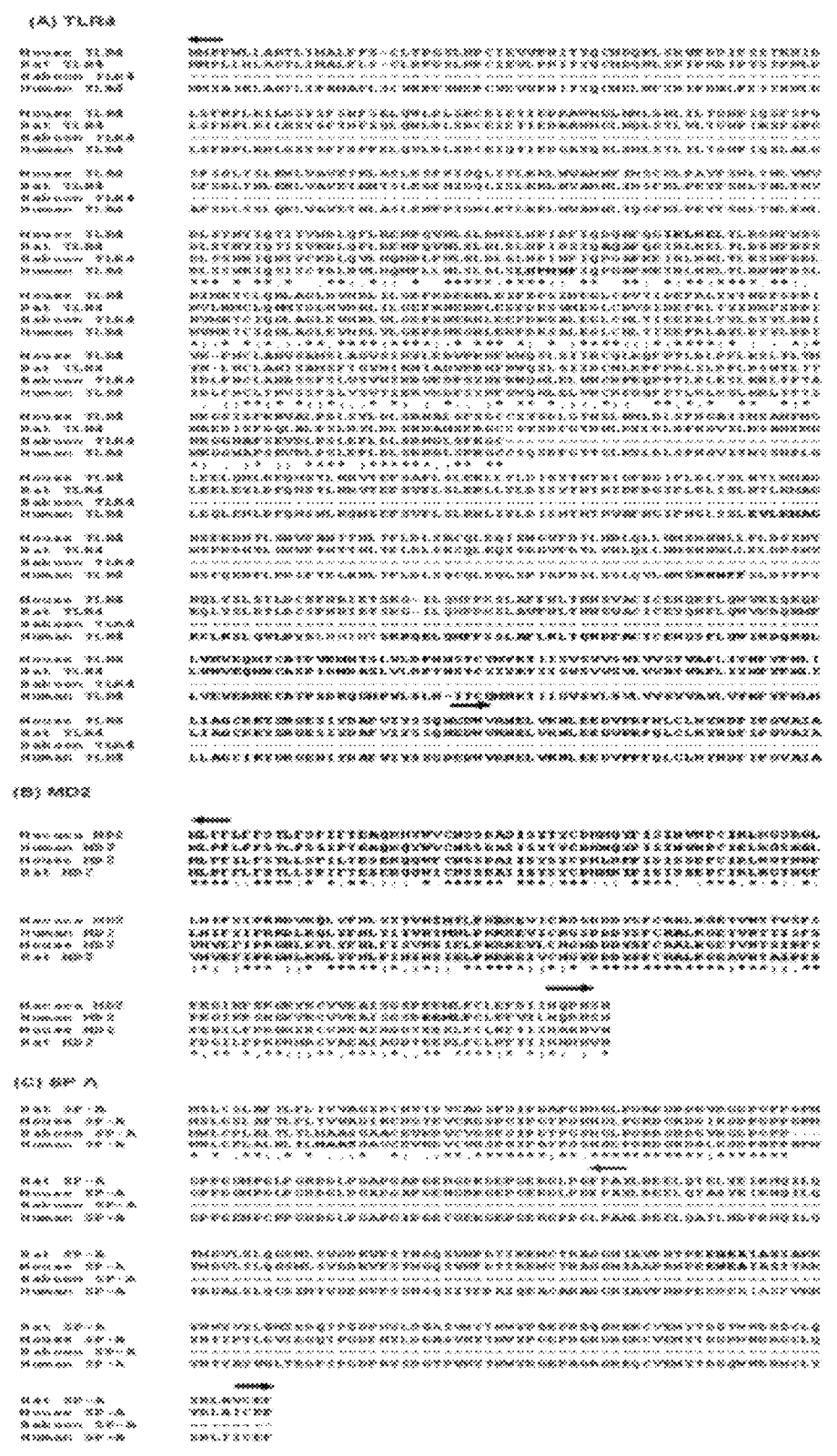

TLR4-MD2 structure: For TLR4-MD2 proteins, the amino acid sequences and dimer crystal structure of human TLR4-MD2 complex are available in PDB bank (PDB ID: 3FXI). Although the TLR4 and SP-A proteins are considered highly conserved proteins, SP-A, TLR4 and MD2 sequence homology was checked between the respective animal species using CLUSTALW multiple alignment program (Protein Information Resource, Georgetown University Medical Center, Washington D.C.). Only partial sequences were available for baboon SP-A and TLR4, and there was no information available on baboon MD2. The alignment results demonstrate that the SP-A, TLR4 and MD2 proteins are highly conserved among different species (including mouse, rat, macaca, baboon and human) (FIG. 11).

Figure 10:
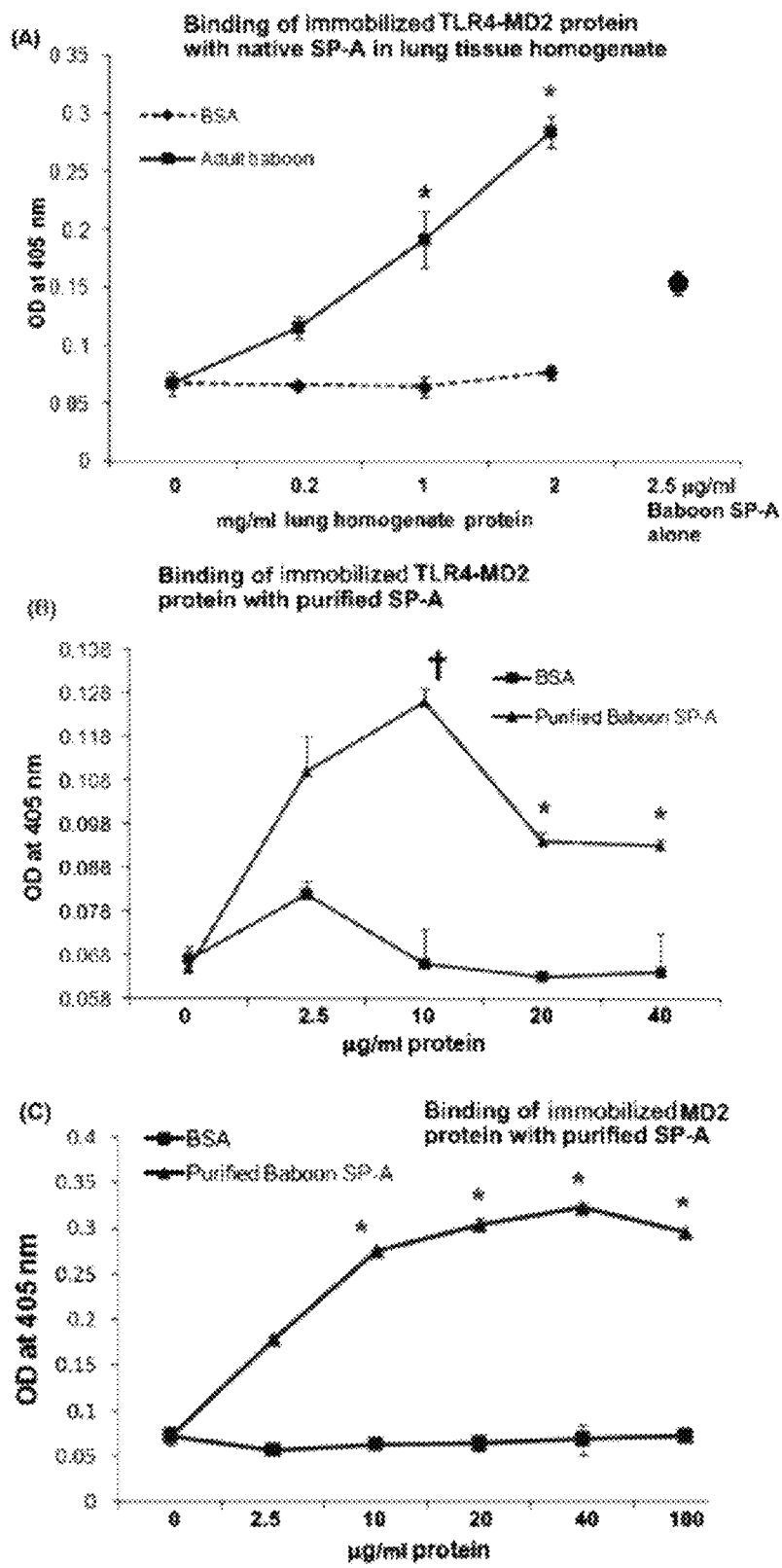
FIG. 10 graphically illustrates the binding between SP-A and recombinant-TLR4-MD2 or MD2 protein by a microwell based-method. Various concentrations of (A) lung tissue homogenate protein (0.2-2 mg/ml) (B) or purified SP-A protein (2.5-40 µg/ml) were incubated with immobilized recombinant TLR4-MD2 protein (0.25 µg per well) and the complex was detected using SP-A-specific antibody. (C) Binding between purified baboon lung SP-A and immobilized recombinant MD2 protein (0.25 µg per well). Various concentrations of purified SP-A protein (2.5-100 µg/ml) were added. The wells were washed and the complex was detected using SP-A-specific antibody. The binding of SP-A to BSA protein shows non-specific binding. The results are representative of two experiments performed in triplicate. The error bars represent standard error of mean (SEM).*$p<0.05$, †$p<0.1$ versus BSA control (t-test).
Figure 12:
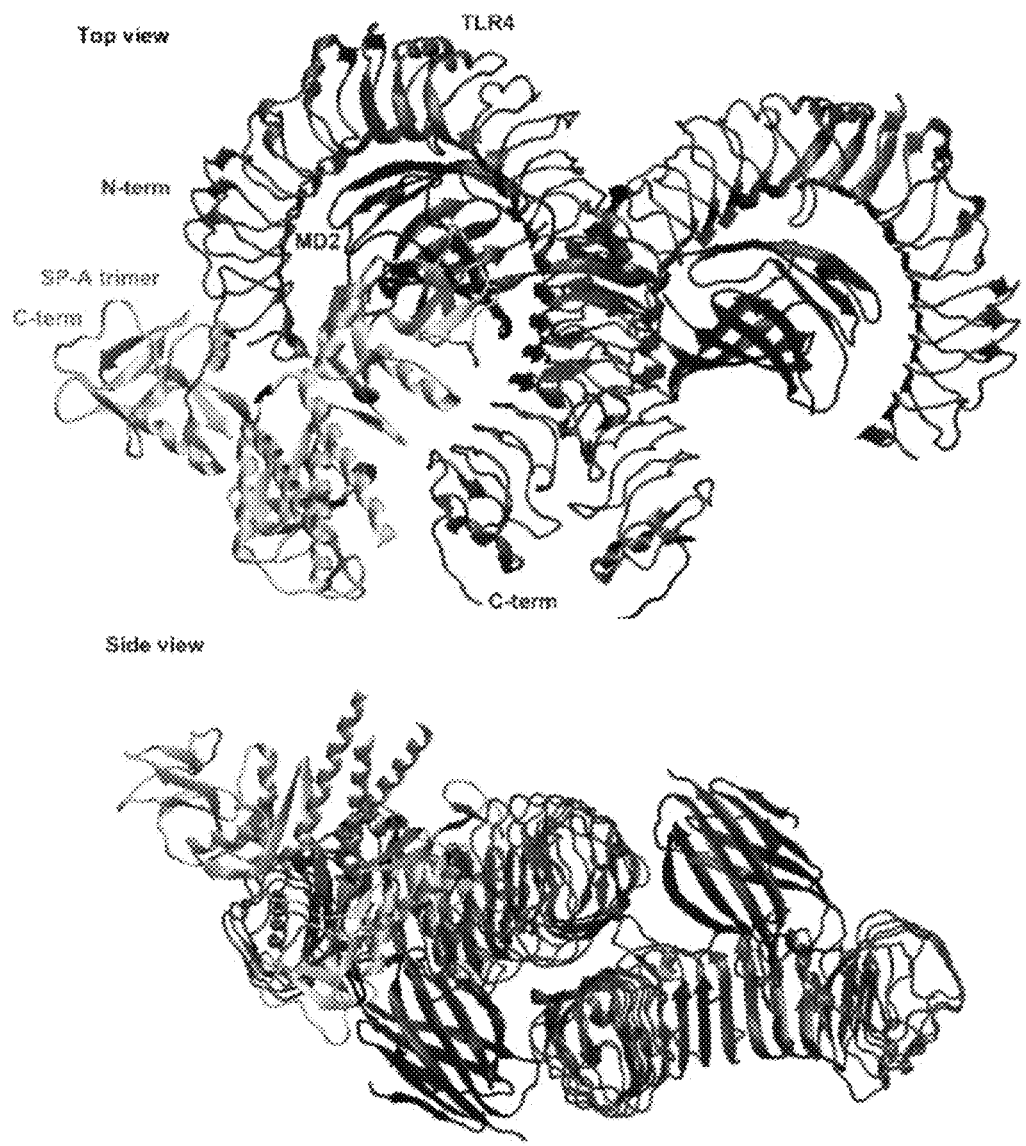
FIG. 12 illustrates that the c-terminal portion of SP-A binds to the extracellular domain of the TLR4-MD2 complex. First, the structure of SP-A trimer was predicted by the SymmDock program from the monomeric crystal structure (PDB ID 1R13). Next, the predicted trimer was used to dock with TLR4-MD2 complex (PDB ID 3FXI) using GRAMM-X webserver. The above configuration is the most likely interaction model, based on GRAMM-X server ranking and detailed analysis.

Protein-protein docking: Next, the protein-protein docking was carried out using Global Range Molecular Matching (GRAMM-X) methodology (Tovchigrechko and Vakser, 2006) on a public web server by submitting the PDB files (trimer assembly of SP-A and dimer receptor-adaptor molecule complex of TLR4 and MD2). GRAMM-X represents a new implementation of original GRAMM methodology that uses a smoothed Lennard-Jones potential on a fine grid during the global search Fast Fourier Transformation stage, followed by refinement optimization in continuous coordinates and rescoring with several knowledge-based potential terms (Tovchigrechko and Vakser, 2006). The top 100 docked configurations were visually examined to select the most plausible configurations. Results from published studies (Yamada et al., 2006) and the inventor's data were considered to set the inclusion and exclusion criteria for the selection of the most plausible model of SP-A-TLR4-MD2 complex. First, 90 configurations that did not show the MD2 adaptor molecule interacting with SPA in the SP-A-TLR4-MD2 complex were discarded, because the microwell-based assay results indicated binding between SP-A and MD2 adaptor molecule (FIG. 10). In the remaining 10 configurations, some were same configurations with the SP-A docked to a different monomer of the TLR4-MD2 dimer. Finally, only three distinct configurations remained. Of these three configurations, the configuration that had the highest area of contact between the molecules was chosen, which also happened to be the configuration ranked 'one'. It is a model in which the C-terminal portion of SP-A binds to the extracellular domain of TLR4 (FIG. 12).

Figure 13:
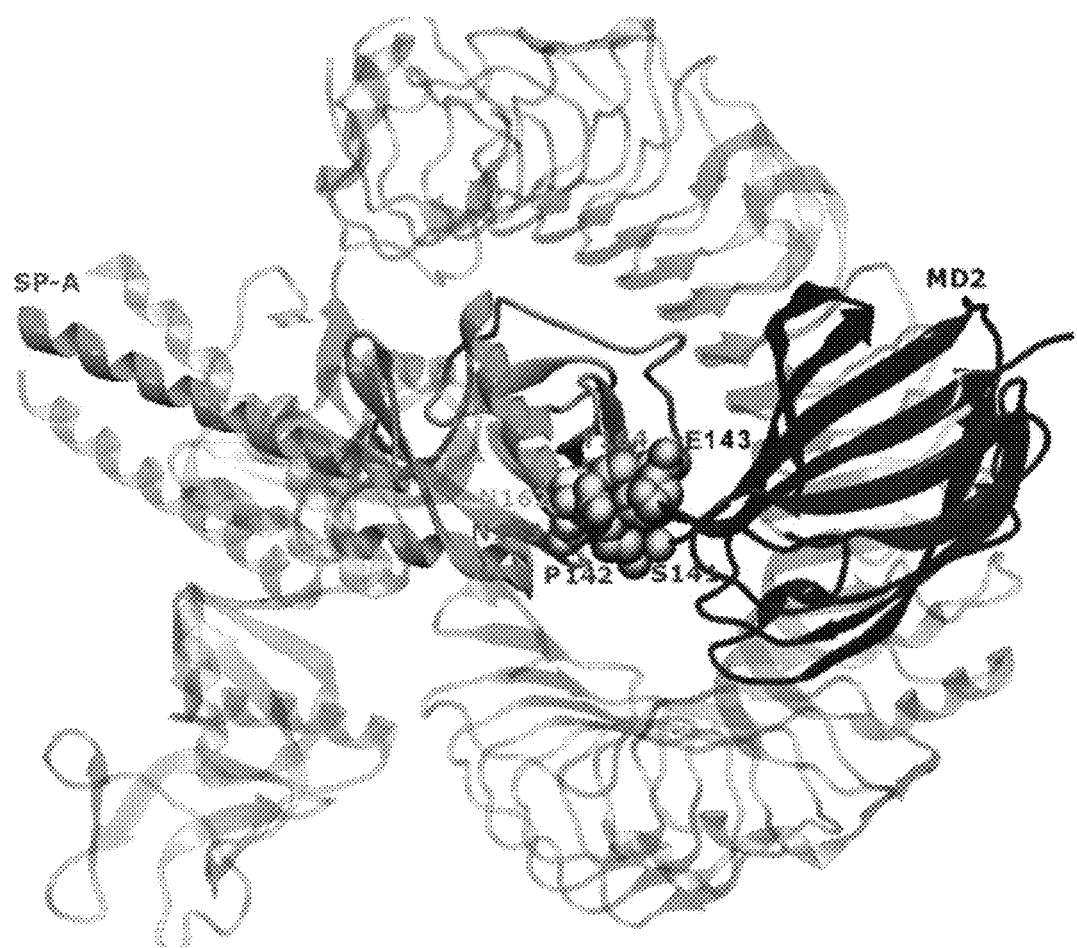
FIG. 13 illustrates the amino acids that are likely to interact in the docked model of SP-A-TLR4-MD2 complex, as shown in FIG. 12. In the illustration here, the other parts of the complex (two chains of SP-A and TLR4) are rendered transparent to focus on the SP-A-MD2 interaction site.
Figure 14:
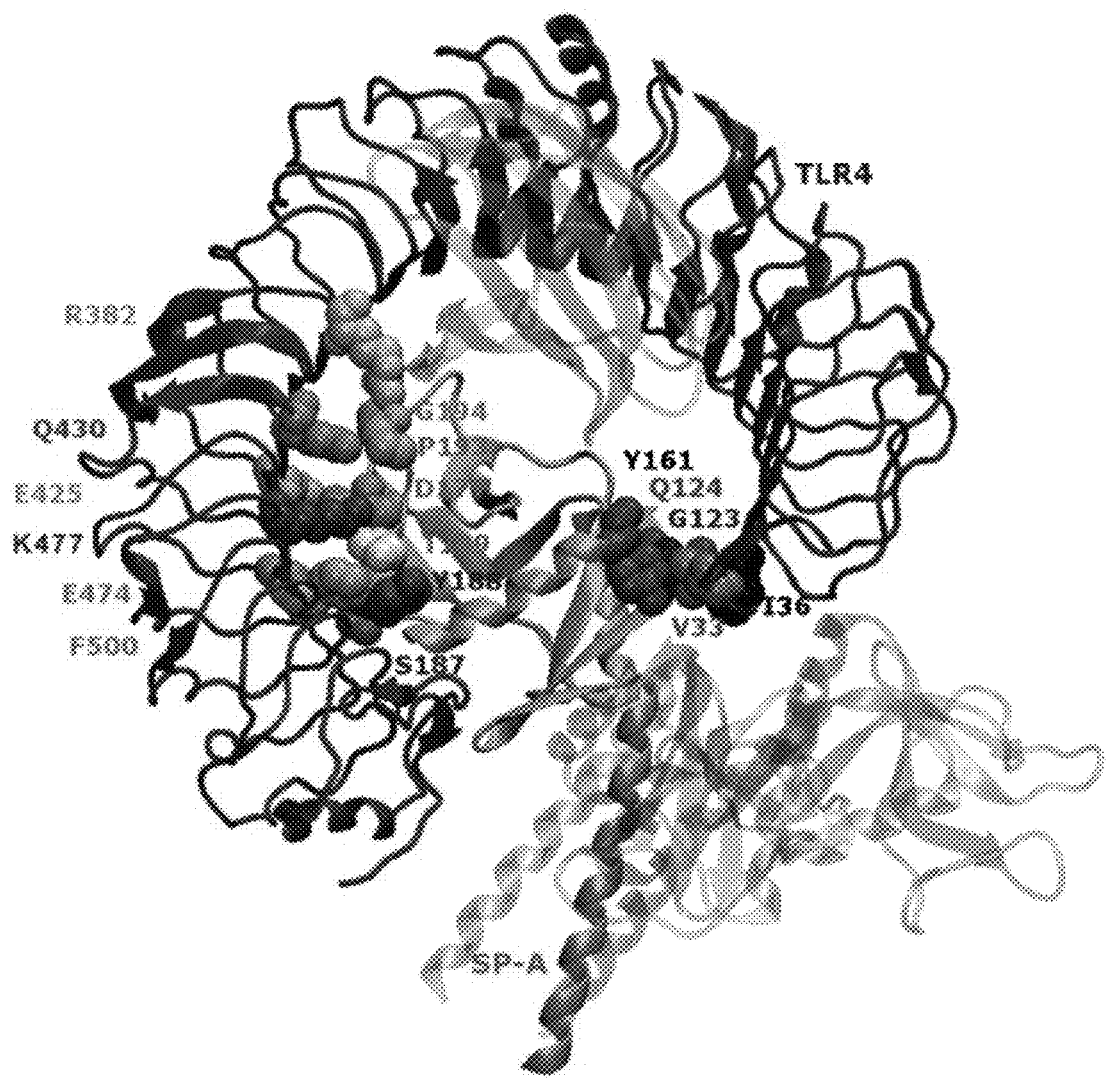
FIG. 14 illustrates the docked model of SP-A-TLR4-MD2 complex, as shown in FIG. 12. This illustration shows that SP-A interacts with TLR4 in SP-A-TLR4-MD2 complex in at least four different places. The second monomer of the TLR4-MD2 dimer has been removed from the original model here for clarity. Also, the non-interacting chains of SP-A and MD2 molecule have been rendered transparent.

Identification of amino acids at the interface of in silico model of SP-A-TLR4-MD2 protein complex: To examine the binding interface of the complex and identify the amino acids at the SP-A-TLR4 and SP-A-MD2 interfaces, the structures were input into another server called Knowledge-based FADE and Contacts (KFC; comprised of Fast Atomic Density Evaluator (K-Fade): shape specificity features and K-Con: biochemical contacts such as intermolecular hydrogen bonds and atomic contacts) (Darnell et al., 2007). The server predicts the binding hotspots and the associated prediction confidence based on the shape specificity features and biochemical contact features of the residues at the interface. The predicted docking configuration of the SP-A-TLR4-MD2 complex with high confidence (K-Fade>0.9 or K-Con>0.9) have been highlighted in FIGS. 13 and 14 using Van der Waals representation. The rendering was carried out using Visual Molecular Dynamics program (Humphrey et al., 1996). The amino acids (SP-A: Asn162-Asn163-Tyr164; MD2: Ser141-Pro142-Glu143) in the selected docked configuration were highlighted using a Van der Waals representation (FIG. 13). In the illustration (FIG. 13), the other parts of the complex (two chains of SP-A and TLR4) are rendered transparent to focus on the SP-A-MD2 interaction site. According to the prediction from the KFC server, the SP-A and TLR4 proteins interact at four different places (FIG. 14). The amino acids involved at the interface of TLR4 and SP-A (K-Fade>0.9 or K-Con>0.9) are listed in Table 2.

Functional Screening of SP-A library revealed a peptide (SPA4; SEQ ID NO:3) that reduces LPS-induced TNF-α secretion. Based on the in silico observations and homology to respective SP-A regions between rat and humans, the SP-A peptides derived from C-terminal CRD of human SP-A were synthesized. SP-A peptides were tested for purity by mass spectrometry (Genscript, CA) and for endotoxin contamination by LAL test.

TABLE 2

Amino acids identified at the SP-A-TLR4 interface.

| Molecule | Amino Acid | Residue # | K-Fade Conf | K-Con Conf |
|---|---|---|---|---|
| TLR4 (human TLR4) | VAL (V) | 33 | 1 | 1 |
|  | ILE (I) | 36 | 0.6 | 0.92 |
|  | ARG (R) | 382 | 1 | 1 |
|  | GLU (E) | 425 | 1 | 1 |
|  | GLN (Q) | 430 | 0.93 | 0.92 |
|  | GLU (E) | 474 | 0.9 | 1 |
|  | LYS (K) | 477 | 0.94 | 0.83 |
|  | PHE (F) | 500 | 1 | 0.91 |
| SP-A (rat-SP-A) | GLY (G) | 123 | 1 | 1 |
|  | GLN (Q) | 124 | 1 | 1 |
|  | TYR (Y) | 161 | 1 | 1 |
|  | ASP (N) | 177 | 0.92 | 1 |
|  | SER (S) | 187 | 1 | 0.85 |
|  | TYR (Y) | 188 | 1 | 0.81 |
|  | THR (T) | 189 | 0.91 | 0.82 |
|  | PRO (P) | 193 | 1 | 1 |
|  | GLY (G) | 194 | 1 | 1 |

Figure 15:
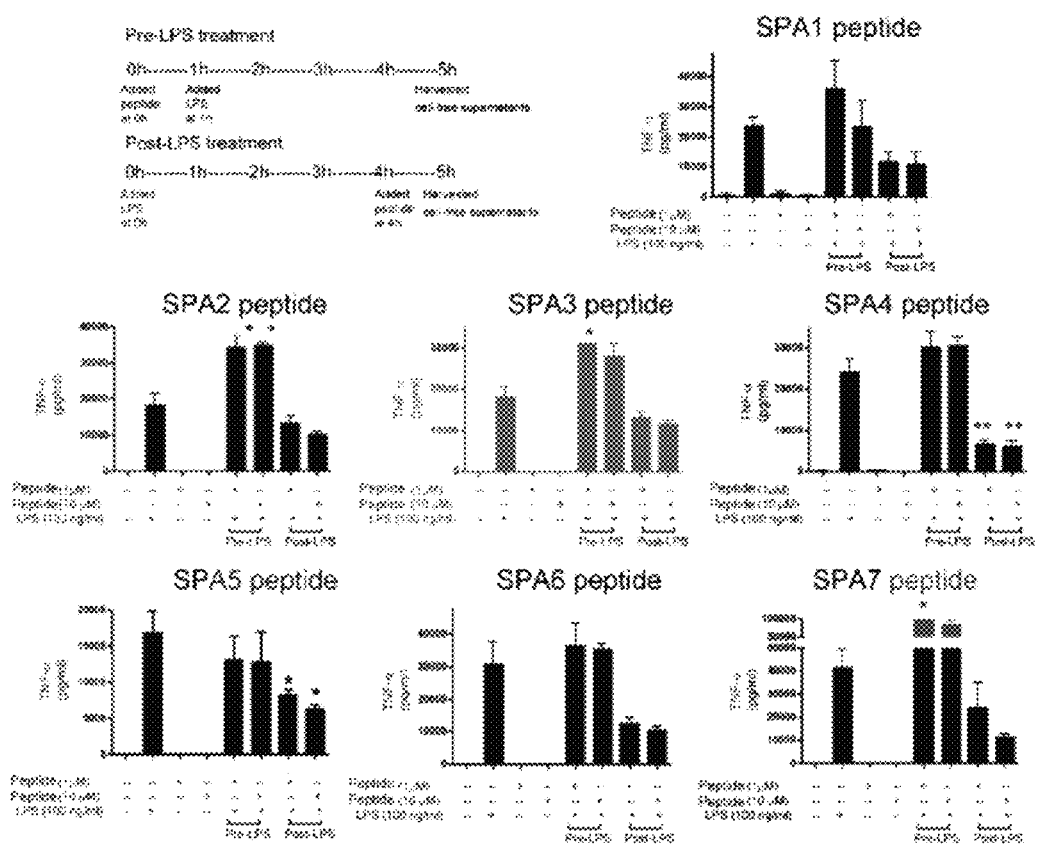
FIG. 15 graphically depicts the effect of synthetic SP-A peptides on LPS stimulated-TNF-α release by JAWS II dendritic cells. The experimental schematic is shown for pre-LPS and post-LPS treatment of cells with SP-A-peptides. The control cells were treated with vehicle control, SP-A-peptides (1 and 10 µM) or LPS (75 ng/ml) alone for 5 hours. The cell-free supernatants were collected after 5 hours of stimulation. The results are from three experiments performed in triplicate. The error bars represent SEM. *$p<0.05$ and **$p<0.001$ as compared to TNF-α levels in cell-free-supernatants of LPS-treated cells (Analysis of variance (ANOVA)).

Since an exaggerated activation of TLR4 is directly linked to secretion of pro-inflammatory cytokine (TNF-α) and SP-A in downregulating TLR4-induced TNF-α in lung dendritic cells (Example 1), SP-A peptides were screened for any changes in LPS-induced TNF-α cytokine secretion in JAWS II dendritic cells. Pre-LPS and post-LPS inflammation models were included in this study to investigate if the peptides affect the LPS-mediated responses, prophylactically or therapeutically. It was found that most of the peptides had no effect on LPS-induced TNF-α secretion in the pre-LPS model, except SPA2 (SEQ ID NO:248), SPA3 (SEQ ID NO:249) and SPA7 (SEQ ID NO:251), which stimulated a slight increase in TNF-α secretion. In the post-LPS model, two peptides (SPA4 and SPA5 peptides; SEQ ID NOS:3 and 5, respectively) were found that inhibited the secretion of TNF-α in post-LPS treated cells at both 1 and 10 μM concentrations (FIG. 15). However, the SPA4 peptide had more effect on LPS-induced TNF-α than SPA5 peptide (mean values 6448 versus 8284 pg/ml at 1 μM concentration, and 6101 versus 6319 pg/ml at 10 μM concentration). Coincidentally, the SPA4 peptide contains most of the amino acids recognized at the interface of SP-A and TLR4 in the in silico model of the SP-A-TLR4-MD2 complex, and SPA5 peptide contains the first 10 amino acids of the SPA4 peptide.

Figure 16:
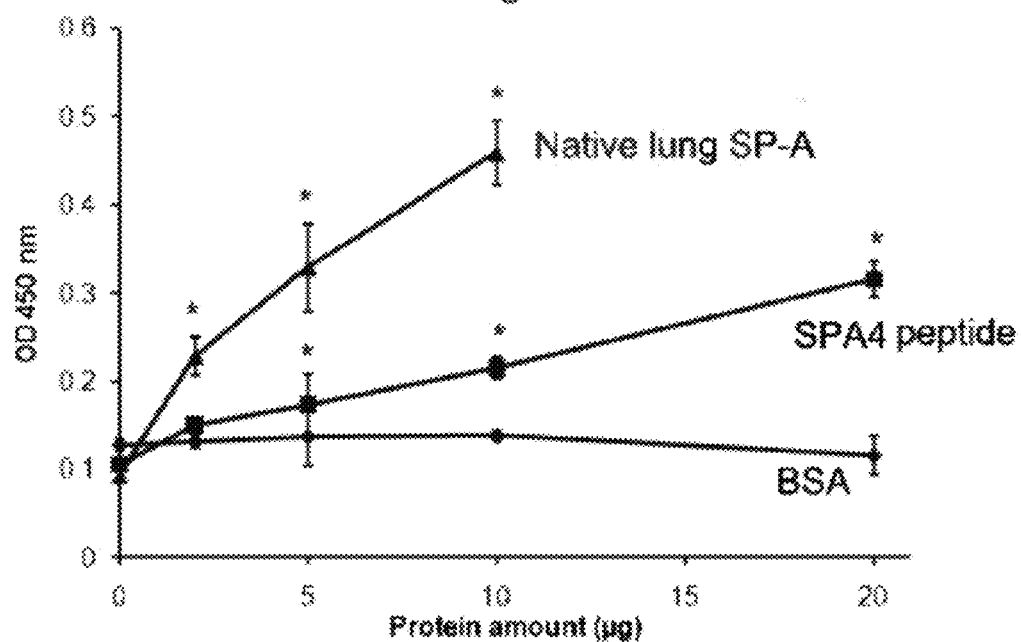
FIG. 16 graphically depicts the binding between SPA4 peptide and recombinant-TLR4-MD2 protein by a microwell based-method. Native SP-A purified from baboon lung was included as control. Various amounts of purified native SP-A protein (2-10 µg) or SPA4 peptide (2-20 µg) were incubated with immobilized recombinant TLR4-MD2 protein (0.25 µg per well), and the complex was detected using SP-A-specific antibody. The results are from one representative experiment of three experiments performed in triplicate. The error bars represent SEM. The binding of SP-A or SPA4 peptide to BSA protein shows non-specific binding. *$p<0.05$ as compared to 0 µg protein (t-test).

SPA4 peptide binds to TLR4 and blocks the LPS-induced TLR4 expression. Next, the binding of the SPA4 peptide with recombinant TLR4-MD2 protein was confirmed by an in vitro microwell-based binding assay. The binding results showed that similar to purified native SP-A, the SPA4 peptide binds to TLR4-MD2 protein (FIG. 16). Binding of the SPA4 peptide to TLR4-MD2 protein was observed as less efficient than the whole native SP-A protein, which exists as an octadecamer (composed of six trimers). The SPA4 peptide, however, represents a small portion of the TLR4-interacting region of SP-A derived from a monomer. Since a polyclonal antibody was utilized to detect the binding of SP-A and SPA4 peptide with TLR4-MD2 proteins, the epitope detection may differ depending on whether it is a fragment (SPA4 peptide) or a full-length protein (purified baboon lung SP-A).

Figure 17:
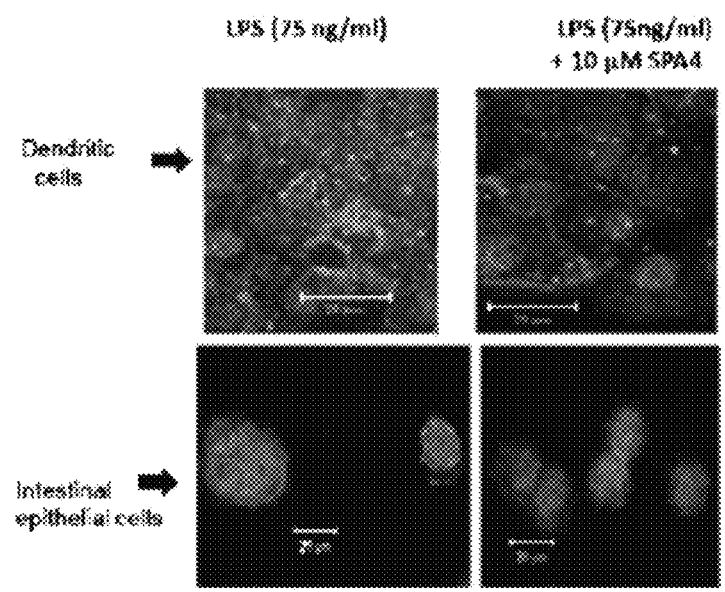
FIG. 17 depicts that SPA4 peptide reduced LPS-induced TLR4 expression. Rhodamin-phallodin (red) stained actin, Hoechst 3342 (blue) stained nucleus, and Alex fluor 488 (green) stained TLR4.

SPA4 peptide-induced changes in the expression of TLR4 were also investigated in dendritic cells. It was found that SPA4 peptide treatment reduced the basal TLR4 expression in JAWS II cells. These results further demonstrate that the LPS-induced TLR4 expression was also suppressed significantly after treatment with SPA4 peptide (*p<0.05, FIG. 17).

Discussion of Example 2

In lung, SP-A is synthesized by type II lung epithelial cells, and is secreted in alveoli as a component of surfactant (King and Clements, 1972). SP-A plays a critical role in pathogen-opsonization, clearance, downregulation of inflammation, and maintenance of lung function. Earlier the inventor observed that the amounts of SP-A secreted in alveoli are significantly reduced in preterm baby baboon having bronchopulmonary dysplasia and in mouse models of lung infection (Awasthi et al., 1999; Awasthi et al., 2001). Thus, it is reasonable to imagine that administration of SP-A should enhance clearance of pathogens and inhibit inflammation. Unfortunately, currently available surfactants do not contain SP-A, because it is a large and hydrophilic protein and cannot be mixed efficiently with surfactant lipids. Therefore, it is important to search for smaller fragments of SP-A. Unavailability of such an SP-A-derived fragment has been associated with the lack of an appropriate model to mimic such a complex scenario.

Since the discovery of TLR4 as a pathogen-recognition receptor that is mainly expressed by the antigen-presenting cells (Armstrong et al., 2004; Awasthi and Cropper, 2006; Basu and Fenton, 2004), it is now established that an exaggerated expression and activity of TLR4 leads to a deleterious inflammatory response. However, basal activity is important for antigen-presentation and adaptive immunity. Subsequent to finding the reduced levels of SP-A, it was observed that the expression of TLR4 is significantly increased in lungs of baby baboons having bronchopulmonary dysplasia (Awasthi et al., 2008). Similar results (i.e., reduction in SP-A and increase in TLR4 expression) have also been reported in other models by other investigators (Alcorn et al., 2005; Chang et al., 2006; Gagro et al., 2004; Kajikawa et al., 2005). The reduction in SP-A amounts and concomitant increase in TLR4 expression corroborates with the clinical condition of patients with lung infection where reduced pathogen-clearance is observed with robust inflammation.

A number of SP-A-binding proteins and receptors have been recognized; however their functions and expression by cell type remain unexplored (Gil et al., 2009; Stevens et al., 1995; Strayer et al., 1993; Wissel et al., 1996). The binding of SP-A to the TLR4 protein has also been recently shown to occur under in vitro conditions (Yamada et al., 2006); however, the in vivo evidence had been lacking, and functional relevance remained largely unexplored. Example 1 demonstrates that simultaneous pulsing of dendritic cells with SP-A and TLR4-MD2 proteins maintains the increased phagocytic uptake, but downregulates the TLR4-MD2-induced inflammatory response against infectious stimuli. It is believed that downregulation of the inflammatory response may be via interaction between SP-A and TLR4. Thus, a smaller fragment of SP-A containing the TLR4-interacting region should inhibit the TLR4-mediated inflammatory response while maintaining the basic functions of antigen-presenting cells.

In this Example, it was demonstrated that SP-A and TLR4 proteins are co-immunoprecipitated from baboon lung tissue homogenates. This is the first report where such an interaction between SP-A and TLR4 has been shown to exist in the lung by immunoprecipitation/immunoblotting and microwell-based methods using lung tissue homogenates and purified lung SP-A. Earlier, interaction between SP-A and TLR4 was studied with purified or recombinant forms of proteins by ligand-blot, microwell-based binding assay and BIAcore methods (Chroneos et al., 2010; Yamada et al., 2006). Bioinformatics simulation studies further support the interaction between SP-A and TLR4-MD2 protein. Although several aspects of TLR4 and SP-A binding are not clearly understood, it is clear that the lung microenvironment may significantly influence their interaction. It should be noted that in the antibody-based methods employed here, the kinetics and characteristics of binding between the two proteins depend on the antigen-antibody affinity. The specific binding sites of both the SP-A and TLR4 proteins and the kinetic parameters of the native-SP-A-TLR4 interaction needed further investigation. It is important to note that the native SP-A molecule (ligand) is quite large (octadecamer) because of the oligomerization of trimers (Pastva et al., 2007), and TLR4 protein is a homomer and associates with other adaptor (MD2) and signaling receptors for its activity (Re and Strominger, 2002). Moreover, it was also found that SP-A can bind to the TLR4 adaptor molecule MD2 as well. Thus, computer modeling of the SP-A-TLR4-MD2 complex was considered; an in silico model of SPA-TLR4-MD2 complex was obtained where the binding features fitted best with the results from immunobiochemical assays (FIGS. 9 and 10). The selected in silico model was analyzed further to identify potential binding sites and amino acids.

As identified earlier, the functional significance of such an interaction is very difficult to assess in vivo. The functional relevance of such an interaction can be better examined under in vitro conditions in a controlled environment using cell culture systems and the appropriate dosage of effector molecules. Thus, the JAWS II dendritic cell system, established in the inventor's lab (Awasthi et al., 2005; Awasthi and Cox, 2003), was used to investigate the effects of SP-A peptides derived from the TLR4-interacting region on cytokine response against a well-known inflammatory stimuli: LPS. It was found that SPA4 peptide (1) encodes most of the amino acids belonging to TLR4-interacting region in in silico model, (2) binds to TLR4-MD2 protein and (3) reduces LPS-induced TLR4 expression and cytokine response.

These results demonstrate that SP-A blocks the TLR4-MD2-mediated intracellular signaling and cytokine release against infectious stimuli. Recently in human monocytes culture system, Henning et al. found that SP-A did not affect TLR4 expression, but it downregulated the TLR4-mediated signaling against LPS (Henning et al., 2008). However, based on the information on the interacting amino acids at the SP-A-TLR4 interface in the computer-simulated SP-A-TLR4-MD2 complex model, and screening of the peptides, one peptide was identified (SPA4) that not only inhibits the LPS-stimulated TLR4 expression, but also suppresses LPS-induced TNF-α release.

Example 3

Use of SPA4 to Modulate TLR4 Signaling for Treatment of Intestinal Inflammation

About a million people are currently suffering from inflammatory bowel diseases (IBD) in the US alone, and new cases are being diagnosed at the rate of 10 cases per 100,000 people (American College of Gastroenterology). IBD causes chronic inflammation in the intestine with alternating periods of active and latent disease, and accounts for a huge economic cost associated with multiple clinic visits and hospitalizations. Chronic inflammation can lead to debilitating complications including colon cancer. Lifelong pharmacotherapy remains the mainstay of IBD management, whereas surgery is indicated for the treatment of refractory disease or specific complications.

Conventional IBD therapies include the use of aminosalicylates, corticosteroids and immunosuppressive drugs (e.g., methotrexate, cyclosporin A). These traditional treatment modalities provide symptomatic relief to some extent depending on the severity of the disease, but exert numerous side effects. The side effects can range from perturbed physiological functioning of important organ systems to potentially fatal opportunistic infections. However, recently a better understanding of the mucosal immune system and genetics involved in the pathogenesis of IBD led to development of biologic medications (Guidi et al., 2010; Bosani, et al., 2009; Melmed and Targan 2010; S. Hanauer, 2010). These medications include infliximab, adalimumab and certolizumab pegol, which are antibodies to block TNF-α, an inflammatory cytokine that is present in increased amounts in patients with IBD. Adverse reactions with these anti-TNF-α products include infusion or injection site reactions, upper respiratory infections and malignancies. Other new biologics that have recently entered into clinical trials include adhesion molecule inhibitor (Natalizumab), anti-IL-12, IFN-γ antibodies and growth factors (Gordon et al., 2002; Guan et al., 2009). As the safety and toxic effects remain to be completely evaluated for these new biologics, Natalizumab has already been temporarily discontinued due to JC virus brain infections. At a molecular level, these inhibitors and antibodies target the pre-formed or secreted inflammatory cytokines or cell-surface molecules that can provide neither cure nor a durable effect after discontinuation. Well thought-out strategies are needed to design novel treatment modalities that can provide more sustained therapeutic effect without any significant toxicity or side effects.

Toll-like receptor-4 (TLR4) was first discovered in 1996 as an innate immune recognition receptor for Gram negative bacterial lipopolysaccharide (LPS). Besides LPS, TLR4 is now known to recognize endogenous inflammatory signals, such as heat-shock proteins, fibronectin etc. Over a period of the last 15 years, since the discovery of TLR4, a great deal about its critical role in inflammatory responses in infectious and non-infectious diseases has been determined. Since inflammation is a hallmark of IBD, TLR4 is thought to be important. It has been recently hypothesized that TLR4-signaling probably serves a dual role in the gut as a mediator of both inflammation and mucosal repair. A hypothetical model was provided suggesting that basal TLR4-signaling is required for normal functioning and intestinal homeostasis. It is the exaggerated TLR4-signaling in response to physiological stressors (e.g., hypoxia) and infectious stimuli (e.g., LPS), that leads to intestinal inflammation. Thus, the novel therapeutic agents that can block this exaggerated TLR4/TLR4-signaling may eventually suppress the inflammatory response and help alleviate the symptoms of IBD.

Results of Example 3

SPA4 peptide (SEQ ID NO:3) inhibits the LPS-induced TLR4 expression in dendritic cells and SW480 intestinal (colonic) epithelial cells. After the shorter SP-A fragment (SPA4) was designed that showed binding to TLR4-MD2 protein (Example 2), its immunomodulatory effects were studied using well-established dendritic (JAWS II; ATCC, VA) (Vilekar et al., 2010) and intestinal epithelial cells (SW480; ATCC, VA). Both of these cells constitutively express the TLR4 gene; the protein expression is low in dendritic cells under basal conditions. LPS treatment induced TLR4 expression in both cell types. First, it was determined if the SPA4 peptide inhibits LPS-induced expression of TLR4 in these cells. The cells were treated with 75 ng/ml or 1 µg/ml E. coli-derived LPS (Calbiochem, CA; highly purified, low protein, does not activate TLR2 signaling) for 4 hours prior to addition of SPA4 peptide. After a total of 5 hours, TLR4 expression was studied by confocal microscopy.

Figure 25:
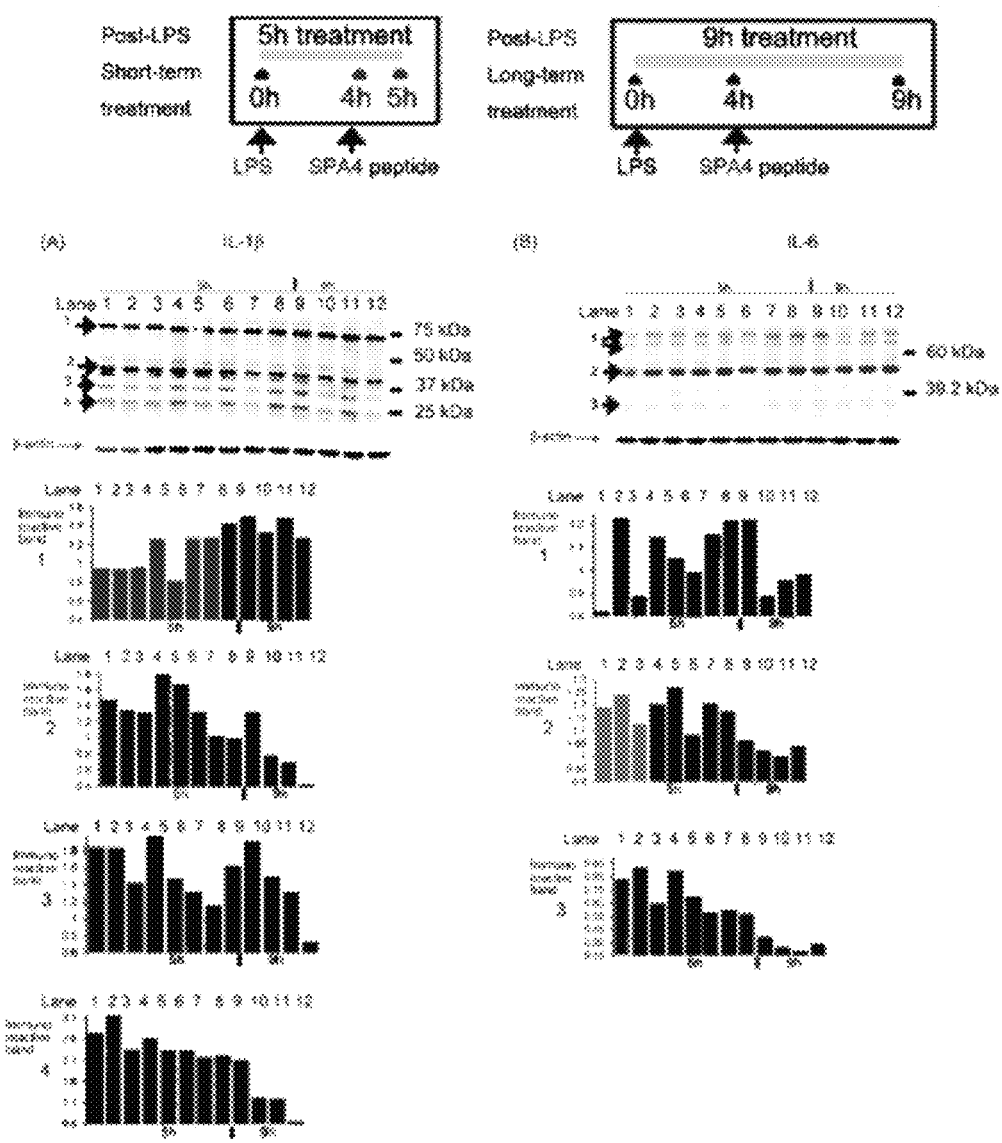
FIG. 25 illustrates the inhibition of LPS-induced expression of cellular IL-1β and IL-6 cytokines by SPA4 peptide. SW480 cells were treated with SPA4 peptide in (left panel) post-LPS challenge and (right panel) pre-LPS challenge models. Cell lysate proteins were probed with antibodies-specific to (A and C) IL-1β and (B and D) IL-6 cytokines. Densitometric readings of immunoreactive IL-1β and IL-6 bands were normalized with those of β-actin. Beta-actin served a loading control. Results are from one experiment of two independent experiments.
Figure 25:
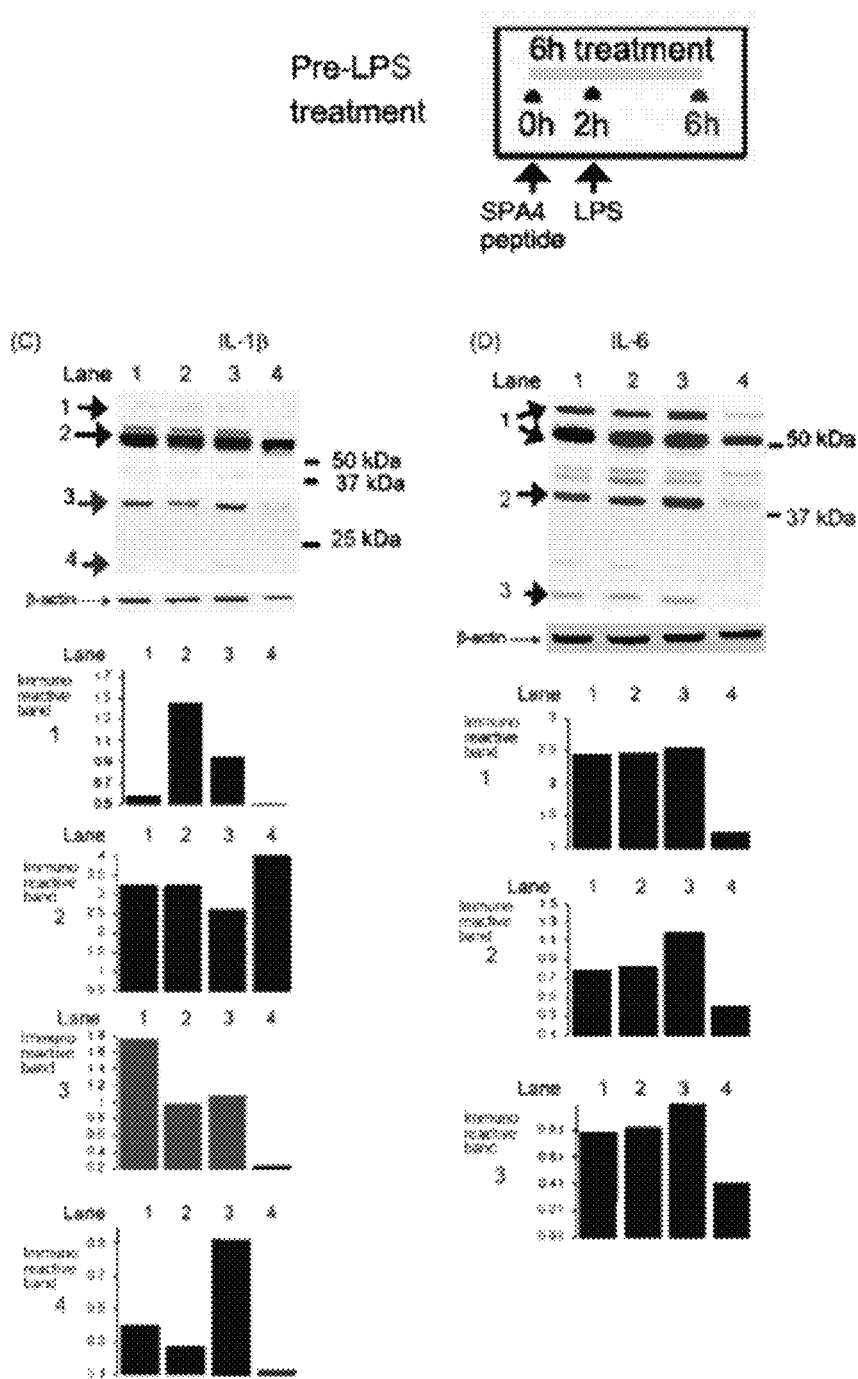

The results demonstrated that the SPA4 peptide reduced LPS-induced TLR4 expression to a basal level (FIG. 17) and inhibited the secretion of pro-inflammatory cytokines (FIGS. 15 and 25). These effects were not related to any cell toxicity, since the SPA4 peptide does not affect the viability of cells within this time period.

Figure 18:
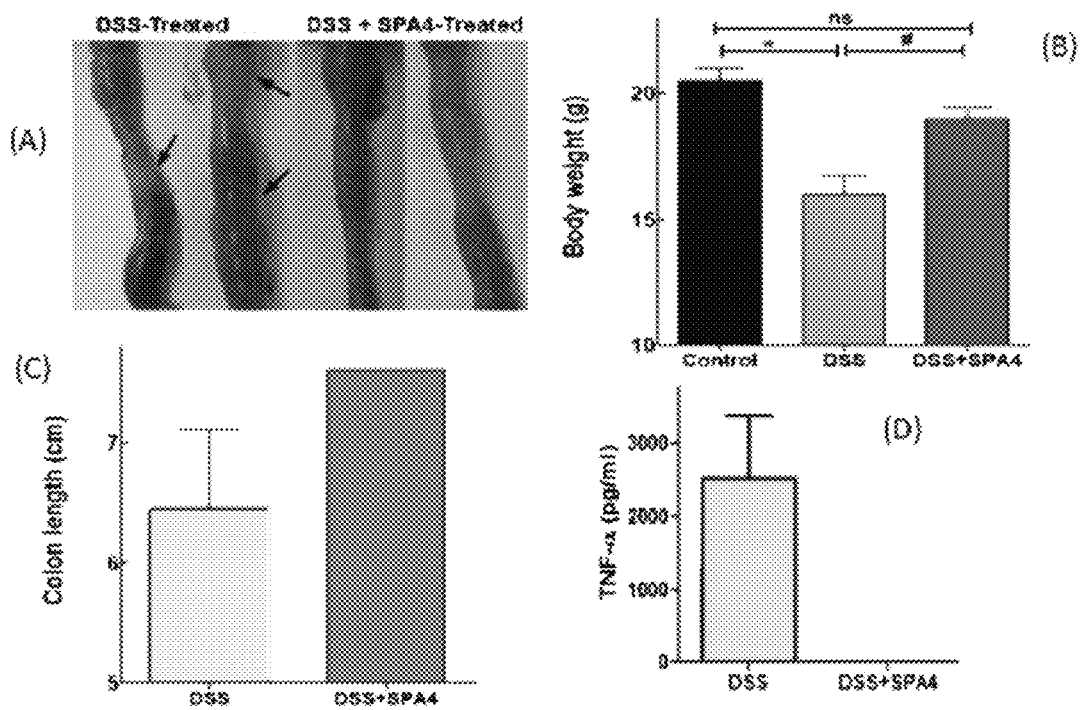
FIG. 18 illustrates that SPA4 peptide reduces inflammation in Dextran sulfate sodium (DSS)-colitis model. DSS challenge induced the colitis symptoms (edema and thickening shown with arrow). Mice with colitis lost about 25% of the body weight, colon was distended and shortened, and serum had increased levels of circulating TNF-α. Simultaneous treatment with SPA4 peptide (100 µg daily) reduced the (A) colitis symptoms. (B) The body weights (*$p<0.001$, #$p<0.01$, ns=not significant) and (C) colon lengths recovered after simultaneous treatment with SPA4 peptide. (D) SPA4 peptide treatment completely inhibited the DSS-induced serum TNF-α.

SPA4 peptide reduced serum TNF-α and inflammation in Dextran sodium sulfate (DSS)-colitis model in mice (FIG. 18). SPA4 peptide was also evaluated in the mouse model of DSS-colitis. DSS (3% in drinking water) was given to the mice for a period of 7 days. In the treatment group, mice were simultaneously injected with SPA4 peptide (100 µg daily via intraperitoneal route). After 2 days of recovery period, the mice were weighed, colons were macroscopically examined, and blood samples were harvested. The TNF-α levels were measured by ELISA.

FIG. 18 demonstrates that SPA4 peptide reduces inflammation in the DSS-colitis model. Mice with colitis lost about 25% body weight; in addition, their colons were distended and shortened. Also, increased levels of circulating TNF-α were detected in the serum. As shown in FIG. 18A, simultaneous treatment with SPA4 peptide reduced the amounts of distension and shortening of the colon, thus demonstrating that the SPA4 peptide reduced the colitis symptoms. In addition, FIGS. 18B and 18C demonstrate that simultaneous treatment with the SPA4 peptide recovered body weight (18B) and colon length (18C) when compared to the DSS-colitis mice. Finally, FIG. 18D demonstrates that SPA4 peptide treatment completely inhibited the DSS-induced serum levels of circulating TNF-α.

Therefore, this Example has demonstrated that the SPA4 peptide suppresses TLR4-signaling in intestinal epithelial and immune cells under inflammatory stress conditions. This suppression of TLR4 at the cellular level results in reducing intestinal inflammation in animals.

Example 4

SPA4 Inhibits Lipopolysaccharide-Induced NF-κB Signaling, Cytokines and Migration of Colon Cancer SW480 Cells Colorectal cancer is the third most common cancer and leading cause of cancer-related mortality in the United States. As per a recent annual report, 141,210 new cases of colorectal cancer and 49,380-associated-deaths were reported in the US only (National Cancer Institute at the National Institute of Health, Washington D.C.). An exaggerated inflammatory response has been reported to increase the risk of colorectal cancer in patients with inflammatory bowel disease (IBD), ulcerative colitis (UC) or Crohn's colitis. This inflammation-induced progression of cancer can potentially be suppressed by anti-inflammatory agents. Common anti-inflammatory medications include the use of aminosalicylates, corticosteroids and immunosuppressive drugs (e.g., methotrexate, cyclosporin A). While it remains to be established whether conventional anti-inflammatory agents can have chemopreventive effects against cancer, an understanding of mucosal immune system and genetics has led to the recent advancements in development of biologic medications against IBD and cancer, specifically anti-TNF-α products (Bosani et al., 2009). A number of anti-TNF-α products (antibodies and receptor antagonists) have been approved by the FDA for reducing inflammation in patients with colitis. Traditional medications and biologics provide only transient relief and have significant side effects that include increased risk of infections and perturbed physiological functioning of important organ systems. These treatment strategies provide short-lived symptomatic relief, mainly because these products act against already secreted TNF-α cytokine or other chemical mediators.

Key molecules involved in inflammatory pathways include Toll-like receptors (TLRs), nuclear factor (NF)-kB, cytokines, growth factors, kinases, cyclooxygenases and nitric oxide synthases. TLRs are unique because they not only sense the "danger signals" in the form of infectious agents or stress-ligands, but by the virtue of their intracellular Toll/Interleukin-1 receptor (TIR) domain, the TLRs are associated with a complex intracellular signaling network, including NF-κB-inflammatory pathway. Thus, new therapies targeting TLR may be of benefit in suppressing inflammation in more sustained fashion. Among a number of TLRs, Toll-like receptor-4 (TLR4) was first discovered in 1996 as an innate immune recognition receptor for Gram-negative bacterial lipopolysaccharide (LPS). TLR4 is now well-recognized as pattern-recognition receptor against a diverse array of ligands including endogenous stress ligands such as but not limited to, heat-shock proteins, fibronectin, etc. A number of recent studies have reported the involvement of TLR4 in colitis and cancer progression. Constitutive activation of TLR4 augments inflammatory response in colitis-induced tumorigenesis. Colon cancer cell lines SW480 and SW620 constitutively express TLR4. In SW480 cells, LPS treatment induces cytokine synthesis/secretion, cell-migration and adhesion. Increased cell migration and adhesion are hallmarks of tumor growth and metastasis. Thus, the inventor postulated that suppression of LPS-stimulated TLR4-signaling will help control inflammation and inflammation-induced metastatic property of SW480 cells. Presumably, a therapeutic that inhibits intracellular inflammatory signaling is expected to exert sustained anti-inflammatory effects and help prevent inflammation-induced cancer.

The previous Examples describe the identification of the TLR4-interacting SPA4 peptide, as well as its ability to reduce secretion of TNF-α by a dendritic cell line in response to LPS stimuli. In this Example, the ability of SP-A4 peptide to inhibit the LPS-induced TLR4-NF-κB signaling and resulting inflammatory response in SW480 colon cancer cell line was studied. Simultaneously, the effects of SPA4 peptide on migration, viability and cell cycle progression of SW480 cells were also investigated.

Materials and Methods for Example 4

Cell culture: Human colorectal adenocarcinoma cells: SW480, derived from the colon of a cancer patient (original stock from ATCC, VA), were obtained from the laboratory of Dr. Shrikant Anant (University of Kansas Medical Center, Kansas City, Kans.). The cells were maintained in Dulbecco's minimum essential medium (D-MEM, Invitrogen, CA), supplemented with high glucose (4.5 g/l D-glucose), sodium pyruvate (1 mM), L-glutamine (4 mM), fetal bovine serum (10%) and antibiomyco (1%, Invitrogen, CA). Cells were maintained at 37° C. in a humidified 5% $CO_2$ incubator.

Figure 19:
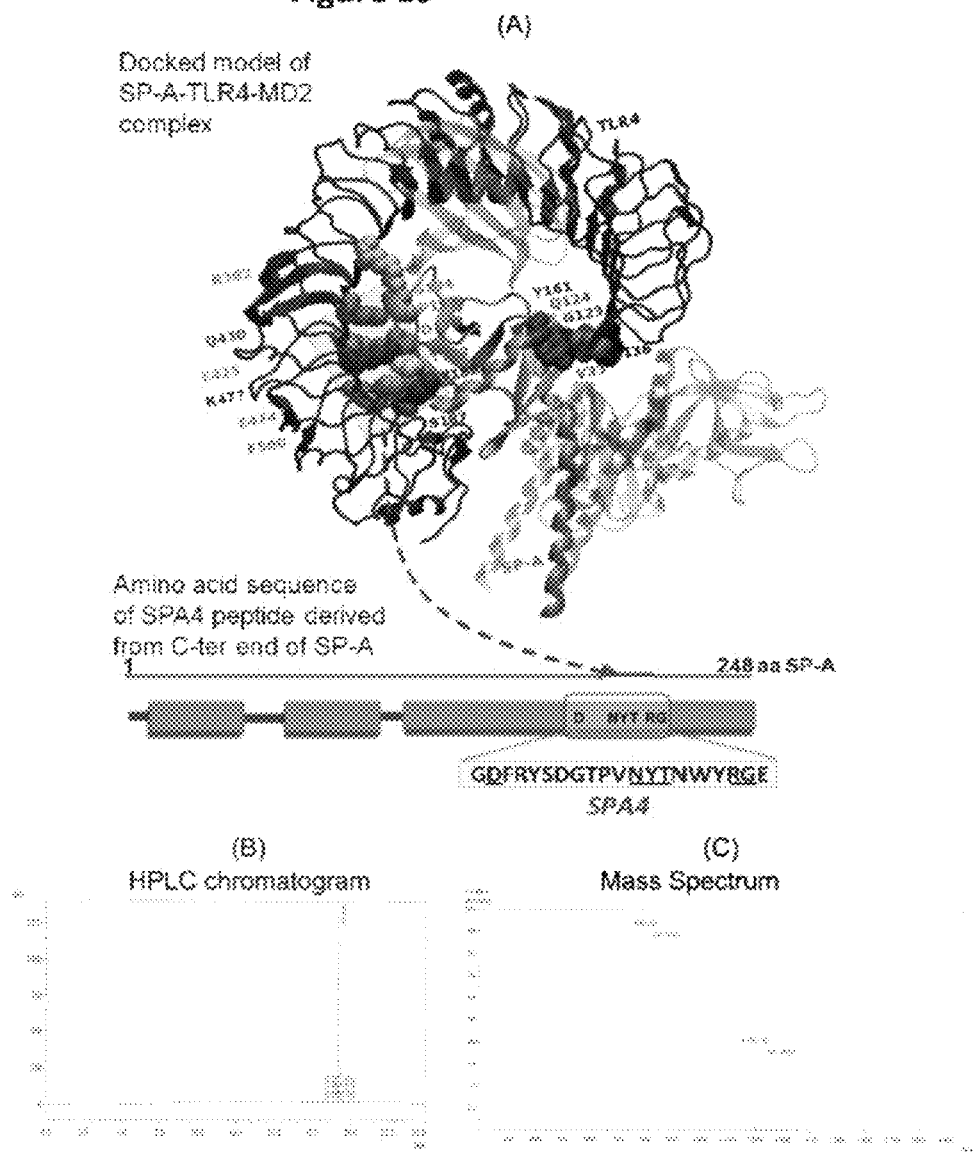
FIG. 19(A) illustrates the amino acid sequence of the SPA4 peptide derived from the TLR4-interacting region of SP-A.
FIG. 19(B) contains a high pressure liquid chromatogram (HPLC chromatogram), while FIG. 19(C) contains a mass spectrum.

SPA4 peptide: The 20-mer SPA4 peptide (amino acid sequence: GDFRYSDGT PVNYTNWYRGE; SEQ ID NO:3) derived from the C-terminal region of SP-A, was synthesized by Genscript (Piscataway, N.J.). The mass spectroscopy and high-performance liquid chromatography were performed on all the batch-preparations of the SPA4 peptide to confirm its purity (FIG. 19). The peptide was suspended in endotoxin-free HyClone Cell culture grade water, and endotoxin content was measured by *Limulus* Amoebocyte Lysate (LAL) assay (Charles River Laboratories International, Inc., Wilmington, Mass.).

Measurement of n-octanol/water partition coefficient ($K_{o/w}$) of SPA4 peptide: The n-octanol/water partition coefficient ($K_{o/w}$) is a measure of hydrophobicity/hydrophilicity. It is calculated as the ratio of the concentration of a chemical in n-octanol to that in water in a two-phase system at equilibrium. An equal volume of MiliQ water and n-Octanol was mixed in a microcentrifuge tube, and shaken for 4 hours at 25° C. Weighed amount of the SPA4 peptide was then added to this n-Octanol-water mixture and shaken overnight at 25° C. The SPA4 peptide-n-Octanol-water mixture was allowed to settle for 2 hours. The aqueous phase was separated by centrifugation at 16,000×g for 10 minutes. The concentration of SPA4 peptide in aqueous phase was measured by spectrophotometric absorbance readings at 280 nm. The concentration of the SPA4 peptide in n-Octanol phase was obtained after subtracting the amount of peptide in water phase from that of the total SPA4 peptide added. Finally, $K_{o/w}$ of SPA4 peptide was determined using following formula:

$$K_{o/w} = \frac{\text{concentration of SPA4 peptide in octanol phase}}{\text{concentration of SPA4 peptide in aqueous phase}}$$

Binding of SPA4 peptide to LPS: The binding of SPA4 peptide to LPS was studied by LAL assay as per the method described by Giacometti et al. (2004). Briefly, 0-20 µM SPA4 peptide or polymyxin B (positive control) solutions were added to 0.01 ng/ml *Escherichia coli* O111:B4 LPS (supplied with the kit, Charles River Laboratories International, Inc., Wilmington, Mass.) in the wells of a 96 well plate and incubated at 37° C. for 40 minutes. Fifty µl of LAL substrate solution was then added to each well, and the plate was incubated for another 10 minutes. Finally, substrate-buffer solution was added, and optical density readings (OD) were obtained at 405 nm after 0, 6 and 12 minutes of addition of substrate. AOD values for SPA4 peptide or polymyxin B incubated with LPS ($\Delta OD_{treatment}$), LPS alone ($\Delta OD_{LPS}$) and blank ($\Delta OD_{Blank}$) were calculated by subtracting the OD values obtained at 6 or 12 minutes from those obtained at 0 minutes. Percent binding of SPA4 peptide and polymyxin B was calculated at 6 and 12 minutes of reaction using following formula:

$$\text{Percent binding} = \frac{1 - (\Delta OD_{treatment} - \Delta OD_{blank})}{\Delta OD_{LPS} - \Delta OD_{Blank}} \times 100$$

Expression of TLR4: Next, the effect of SPA4 peptide on the expression of TLR4 in SW480 cells was investigated by immunocytochemistry and laser confocal microscopy. Briefly, about $2.5 \times 10^4$ cells were seeded in an 8-well chamber slide (Thermo Fisher Scientific, Rochester, N.Y.) in complete medium. The cells were treated with *E. coli* O111:B4-derived, highly-purified, low-protein LPS (100 ng/ml or 1.0 µg/ml; Calbiochem, CA) for 4 hours following 1 hour incubation with SPA4 peptide (1, 10 and 100 µM). The cells were fixed in 3.5% paraformaldehyde in Dulbecco's PBS (DPBS) and permeabilized with 0.05% saponin solution (Inaba et al. 1998). The wells were washed with DPBS supplemented with 1% FBS and 0.05% saponin, and stained with TLR4-specific antibody (1:50 dilution, Abcam, Mass.) and 10 µg/ml Alexa-fluor 488-labeled secondary anti-rabbit IgG antibody (Invitrogen-Molecular Probes, CA). After washing, the cells were stained with 100 nM rhodamin-phallodin (Cytoskeleton Inc, CO) and 1 μg/ml Hoechst 33342 dyes (Invitrogen-Molecular Probes, CA). Confocal microscopic images were acquired at the Imaging core facility of the Oklahoma Medical Research Foundation, Oklahoma City, using the Zeiss LSM-510 META laser scanning confocal microscope. Images were acquired with lens objective of 63× with the x/y stack sizes being 146.2 μm using band pass filter specifications at 435-485, 560-615 and 505-530.

NF-κB activity: Since binding of LPS to TLR4 activates NF-κB through MYD88-dependent and independent pathways, the effects of SPA4 peptide on basal and LPS-induced NF-κB activity were investigated in SW480 cells transfected with a dominant negative construct of MYD88 (MYD88DN) and NF-κB firefly-luciferase reporter plasmid DNA. Both the short-(1 hour) and long-term (5 hours) effects of the SPA4 peptide on NF-κB activity were studied.

The SW480 cells were transiently-transfected with NF-κB firefly-luciferase reporter plasmid pGL4.32 (luc2P/NF-κB-RE/Hygro, Promega, WI; provided by Dr. Kelly Standifer, Department of Pharmaceutical Sciences, University of Oklahoma Health Sciences Center, Oklahoma City, Okla.) and MYD88-dominant negative plasmid construct (MYD88DN, provided by Dr. Ruslan Medzhitov, Yale University, CT). MYD88 dominant negative plasmid DNA construct lacked the death domain and intermediate domain (Medzhitov et al., 1998). Briefly, NF-κB-Luciferase reporter and MYD88-dominant negative plasmids (1.0 μg each) were mixed with 6 μl of Fugene HD reagent (Roche, Ind.) in 92 μl of serum-free low-glucose DMEM medium (Invitrogen, CA), and incubated for 20 minutes at room temperature. The transfection-mix was then added to the SW480 cells. The SW480 cells transfected with a plasmid DNA construct expressing enhanced green fluorescent protein (pHYG-EGFP; Clontech, CA) were observed under Leica DM4000B fluorescent microscope. The transfection efficiency was calculated as percent of cells expressing EGFP over total number of cells in the brightfield channel. An empty vector plasmid DNA (pcDNA 3.0; obtained from Dr. Brian Ceresa, Department of Cell Biology, University of Oklahoma Health Sciences Center, Oklahoma City, Okla.) was used as negative control. The cells were incubated for 18-20 h at 37° C. in humidified 5% $CO_2$ chamber. After the completion of incubation period, fresh complete medium was added to the cells. Cells were then challenged with LPS (1.0 μg/ml) for 4 hours following the treatment with SPA4 peptide (1, 10, 50 μM) for 1 hour (total period of 5 hours; short-term treatment model) and 5 hours (total period of 9 hours; long-term treatment model). The LPS remained in the medium throughout the incubation period.

After completion of the incubation period, the medium supernatants were removed and cells were washed with room-temperature DPBS. The cell extracts were prepared using the reporter assay cell-lysis buffer (Promega, Fitchburg, Wis.) and stored at −80° C. for further analysis. The firefly-luciferase activity (measurement of NF-κB activity) was measured using the luciferase reporter assay system (Promega, Fitchburg, Wis.). Briefly, 50 μl of luciferase assay reagent was added to the 20 μl cell lysate by automated dispenser of Synergy HT multi-mode microplate reader (Biotek, Winooski, Vt.), and luminescence was read within 10 seconds. Total protein content in cell lysates was estimated using BCA protein assay kit (Pierce, Rockford, Ill.). The luciferase activity units were finally normalized with the total protein content of cell lysates.

Expression of NF-κB pathway molecules by immunoblotting: The expression of NF-κB pathway molecules (inhibitor kappa-Bα: IKBα, phosphorylated IKBα, p65, phosphorylated p65, RelB and COX-2) in SW480 cell-lysates treated with LPS±SPA4 peptide was studied by immunoblotting. For the immunoblotting, 10 μg of total cell-lysate proteins were fractionated on Novex 4-20% Tris-glycine gradient SDS-PAGE gel (Invitrogen, Carlsbad, Calif.) by electrophoresis. Separated proteins were electro-transferred onto a nitrocellulose membrane using iBlot gel transfer device (Invitrogen, Carlsbad, Calif.). The non-specific sites were blocked by incubating the membrane with 7% skimmed milk in Tris-buffered saline with 0.4% TWEEN®-20 (TBST) for 1 hour at room temperature. The blocked membranes were incubated overnight at 4° C. with 1:1000 diluted anti-human antibodies against NF-κB canonical pathway molecules: phosphorylated inhibitor kappa-Bα (IKBα), total-IKBα, p65, RelB (Cell Signaling Technology, Inc., Danvers, Mass.), phosphorylated p65 (Santacruz Biotech, Inc., Santa Cruz, Calif.) and cyclooxygenase-2 (COX-2; Santacruz Biotech, Inc., Santa Cruz, Calif.). The membranes were washed with TBST and incubated at room temperature for 45 minutes with 1:3500 diluted horse-radish peroxidase (HRP)-conjugated-secondary antibody (Sigma-Aldrich, St. Louis, Mo.). The immunoreactive bands were detected by Super Signal West Femto detection reagent (Thermo Fisher Scientific, Barrington, Ill.). In order to ensure equal protein loading in the wells, the membranes were stripped of probing antibodies at 60° C. for 45 minutes using a stripping solution containing 10% SDS, 0.5 M Tris and 3-mercaptoethanol (35 μl/ml), and re-probed with anti-actin antibody (Sigma-Aldrich, MO; 1:1000 in TBST). The immunoblots were imaged using the Ultraquant image acquisition program (UltraLum Inc., Claremont, Calif.). The densitometric readings were obtained for immunoreactive bands with Image J 1.42 q program (NIH, USA). Finally, arbitrary densitometric values for proteins of interest were normalized with those of β-actin.

Expression of IL-1β and IL-6: Two treatment models (post- and pre-LPS treatment) were utilized for assessing the effects of SPA4 peptide on LPS-induced cytokines: IL-1β and IL-6. Post-LPS treatment models (short-term and long-term) are described above. In pre-LPS treatment model, the SW480 cells were pretreated with SPA4 peptide (10 μM) for 2 hours, followed by LPS-challenge (1.0 μg/ml) for another 4 hours. The cell-lysates were prepared either in commercially available cell-culture lysis reagent (Promega, WI) or directly into SDS-PAGE sample buffer containing 50 mM dithiothreitol (Cell Signalling Technology, MA). Ten μg of cell-lysate proteins were separated on 4-20% Novex Tris-glycine gradient SDS-PAGE gel (Invitrogen, CA) or 10% separating-5% stacking acrylamide gel. The expression levels of cytokines were measured by immunoblotting as described above using 1:1000 diluted antibodies against IL-1β and IL-6. Both antibodies were purchased from Santacruz Biotech, CA.

Cell migration: SW480 cells were plated in 30 mm tissue-culture-treated dishes at a density of $1.0 \times 10^6$ cells per plate. At 80-90% confluence, a "reference line" was drawn at the bottom of the plate. The cells were scratched off from one side of the reference line using a rubber policeman. A picture was taken at 0 t that helped in marking the "start line". Cells were then washed with complete medium and incubated with LPS (1.0 μg/ml) and/or SPA4 peptide (1, 10 and 50 μM). Photomicrographs of cells migrated across the "start line" were taken in different fields after each treatment at 24, 48, and 72 hours (±2 hours) following traceable inscriptions made under the plate at three different points, with a Canon digital camera. On 24, 48 and 72 hour images, a second line was drawn along the edge of cells to represent the migration of cells. Cell migration was calculated by measuring the distance cells migrated from the "start line". Only the continuous migration of cells was considered for measurement. The islets of cells were disregarded. The cell migration was calculated using the following formula: (distance between "start line" at 0 h—"reference line")-(distance between "72 hours line"—"reference line").

Cell cycle analysis: The effect of SPA4 peptide on cell cycle progression was studied by flow-cytometry. About 500,000 cells were seeded per well into 6 well plate. The cells were challenged with LPS (100 ng/ml) for 4 hours. After the completion of 4 hours LPS-challenge period, SPA4 peptide (10, 50 and 100 µM) was added to the cells. Cells were further incubated for 20 and 40 hours. Vehicle-treated cells were also included. After 20 and 40 hours of total incubation period, both adherent and non-adherent cells were collected and centrifuged at 260×g for 5 minutes. The supernatant was discarded and cell pellet was washed with DPBS (Invitrogen-Gibco, NY). The cells were fixed in 70% ice-cold ethanol on ice for 1 hour and stained with a buffer containing 200 µg/ml DNase-free RNase A (Sigma, St Louis, Mo.), 0.1% v/v Triton-X 100 and 20 µg/ml propidium iodide (Molecular Probes, Carlsbad, Calif.). The cells were incubated at 4° C. for 30 minutes in the dark, before measuring cell fluorescence using Becton Dickson FACS Calibur flow cytometer. The single cells were selected by gating out the aggregates and the percent number of cell populations in different cell cycle phases were calculated by de-convoluting the results ModFIT software (Verity software house, Topsham, Me.).

Cell viability: The TLR4-NF-κB signaling can have multifaceted implications, including the effects on proliferation and viability of SW480 cells. Thus, the effect of SPA4 peptide on viability of SW480 cells was studied. The cells (250,000 and 500,000 per well) were seeded into 24 well plates and treated with SPA4 peptide (10, 50 and 100 µM) after LPS-challenge (100 ng/ml) for 4 hours. The LPS remained in the medium throughout the incubation period thereafter. The cells were collected after 3-5 days of treatment and stained with propidium iodide (1 µg/ml) for 20 minutes on ice. The stained cells were run on a flow-cytometer (Accuri flow cytometer, MI), and propidium iodide staining was assessed on FL2 channel. The histograms were obtained for each treatment using C Flow Plus software and compared between the groups. The % number of cells exhibiting positive (dead cells) and negative (live cells) propidium iodide staining were noted. Untreated cells and LPS-treated cells served as controls.

Statistics: The results were analyzed by one way Analysis of Variance (ANOVA) using a statistical analysis program (Graphpad Prism, CA). A p-value of <0.05 was noted, otherwise indicated.

Results of Example 4

Characteristics of SPA4 peptide: The SPA4 peptide batch preparations were always tested for purity by HPLC chromatography and Mass spectrometry (FIG. 19) or any contamination with endotoxin by LAL assay. The endotoxin level was undetectable (below the lower limit of 0.001 ng/ml) in reconstituted SPA4 peptide suspensions of all the batches.

Figure 20:
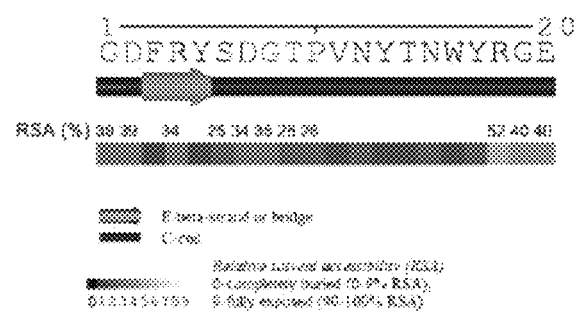
FIG. 20 illustrates the secondary structure and relative solvent accessibility (RSA) values for the 20mer SPA4 peptide (SEQ ID NO:31 as predicted by the Solvent AccesiBiLitiEs (SABLE) program (Division of Biomedical Informatics, Children Hospital Research Foundation, Cincinnati, Ohio). The values indicate RSA values of amino acids exhibiting >25% RSA values.

As per the computer simulation Solvent AccesiBiLitiEs (SABLE) program (Division of Biomedical Informatics, Children Hospital Research Foundation, Cincinnati, Ohio), the SPA4 peptide is predicted to have coiled and beta strand structures. Relative solvent accessibility (RSA) of 11 amino acid residues is above 25% (FIG. 20), suggesting that the SPA4 peptide is easily soluble in water. Furthermore, the Ko/w partition coefficient of the SPA4 peptide was measured. The Ko/w partition coefficient of SPA4 peptide was 0.56. These results further confirm that the SPA4 peptide is hydrophilic in nature.

SPA4 peptide does not bind to LPS. Example 2 illustrated that the SPA4 peptide binds to recombinant TLR4-MD2 protein. In order to further validate that the anti-inflammatory effects of SPA4 peptide are not through the binding of SPA4 peptide to TLR4-ligand LPS, the binding of SPA4 peptide to LPS was studied in vitro. The results in FIG. 21A show that the SPA4 peptide does not bind to LPS.

Additional evidence was provided by superimposing the predicted SPA4 peptide-binding site on a computer model exhibiting LPS-binding site within the TLR4-MD2 complex (Carpenter et al., 2009). Herein it was observed that the binding site of the SPA4 peptide to TLR4 remains farther away from the LPS-binding site (FIG. 21B).

Figure 22:
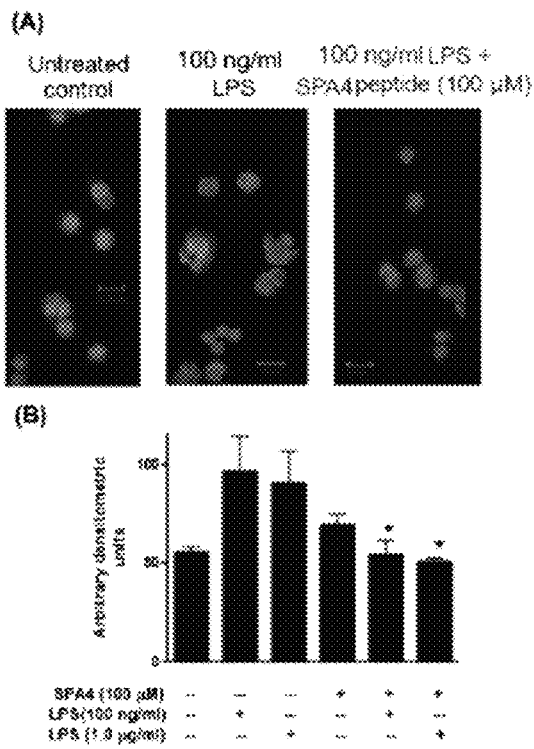
FIG. 22 illustrates the effect of SPA4 peptide on TLR4 expression. SW480 cells were challenged with LPS (100 ng/ml or 1.0 µg/ml) for 4 hours and treated with SPA4 peptide (100 µM) for 1 hour. The cells were subsequently stained with Alexa fluor 488-labeled antibody for TLR4 (green), nuclear stain Hoechst 33342 (blue) and cytoplasmic phalloidin stain (red). (A) Confocal images of cells representative fields are shown for cells treated with 100 ng/ml LPS+100 µM SPA4 peptide. (B) Confocal images of at least 10 different fields were acquired for the cells where nucleus and cytoplasm were visible in the same plane. The fluorescent staining for TLR4 was quantified by densitometry. Mean (SEM) densitometric units are shown as bars. Results are from one experiment representative of two independent experiments performed at different times. *$p<0.05$ versus LPS-challenged cells.

SPA4 peptide reduces the expression of TLR4. Next, the effects of SPA4 peptide on the expression of TLR4 were investigated by confocal microscopy. The results show that SW480 cells constitutively express TLR4. As expected, the TLR4 expression is further increased in response to Gram-negative bacterial LPS. However, the SPA4 peptide treatment reduced the LPS-stimulated TLR4 expression to basal level (FIG. 22), which was more pronounced with 100 µM SPA4 peptide, the maximum concentration tested.

Figure 23:
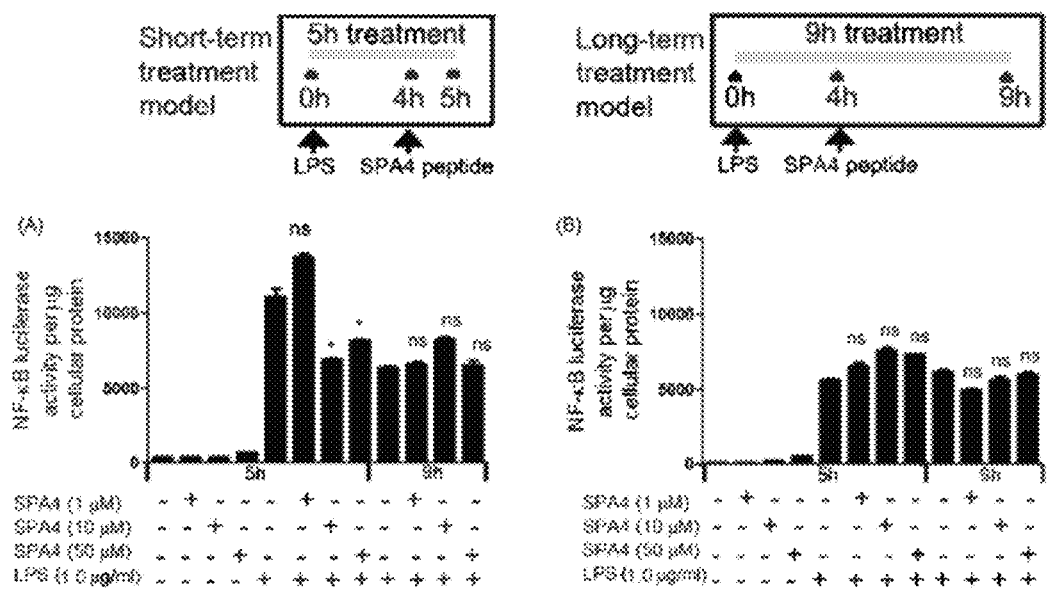
FIG. 23 shows that SPA4 peptide inhibits LPS-induced NF-κB activity. The luciferase activity was measured in cell lysates harvested after 5 hours and 9 hours of short-term and long-term SPA4 peptide treatment models of 1.0 µg/ml LPS-challenged SW480 cells. Cells were co-transfected with either (A) pcDNA-vector and NF-κB-luciferase reporter plasmid DNAs or (B) MYD88-dominant negative (MYD88DN) and NF-κB-luciferase reporter plasmid DNAs. The bars indicate mean (SEM) luminescence values normalized with µg total cell lysate protein. The results are from one experiment representative of four independent experiments performed in triplicate. *$p<0.05$ and ns: not significant versus LPS-challenged cells.

SPA4 peptide inhibits the LPS-induced MYD88-dependent NF-κB activity: Myeloid differentiation primary response gene (88; MYD88) is a known adaptor molecule of TLR4 and serves as an important molecule downstream of LPS-TLR4-MD2 binding, but upstream of activation of transcription factors (AP-1 and NF-κB) and transcription of cytokine and chemokine genes. The MYD88 engages IL-1 receptor-associated kinase (IRAK) molecule through its death domain and transduces the signal. In this Example, SW480 cells were transfected with MYD88 dominant negative construct (MYD88DN) lacking the death domain. The transfection efficiency was observed as 63-68%. The NF-κB activity was measured using a reporter plasmid (pGL4.32, Promega, WI) that contained five copies of NF-κB-response element driving the expression of luciferase reporter gene. The results show that the SPA4 peptide (at 10 and 50 µM concentrations) reduces the LPS induced-NF-κB activity after 5 hours. At 9 hours of treatment, the LPS induced NF-κB activity was, however, not significantly inhibited by 1, 10 or 50 µM concentrations of SPA4 peptide. The MYD88DN-transfected cells exhibited reduced NF-κB activity against LPS stimuli as compared to that in pcDNA3.0 vector plasmid DNA-transfected cells. The SPA4 peptide-treatment did not further reduce the NF-κB activity in cells transfected with dominant negative construct of MYD88, illustrating that the SPA4 peptide treatment affects only the MYD88-dependent NF-κB activity and does not affect the MYD88-independent NF-κ B activity (FIG. 23).

Expression of NF-κB signaling molecules is affected by SPA4 peptide: The effects of SPA4 peptide on LPS-induced TLR4-NF-κB signaling were studied in cells treated with SPA4 peptide (1, 10 and 50 µM) for a short-term and a long-term basis. The expression of NF-κB-signaling molecules was measured in cell lysates by immunoblotting. It was found that the SPA4 peptide alone did not affect the expression of any of the NF-κB signaling molecules studied, except for COX-2.

Figure 24:
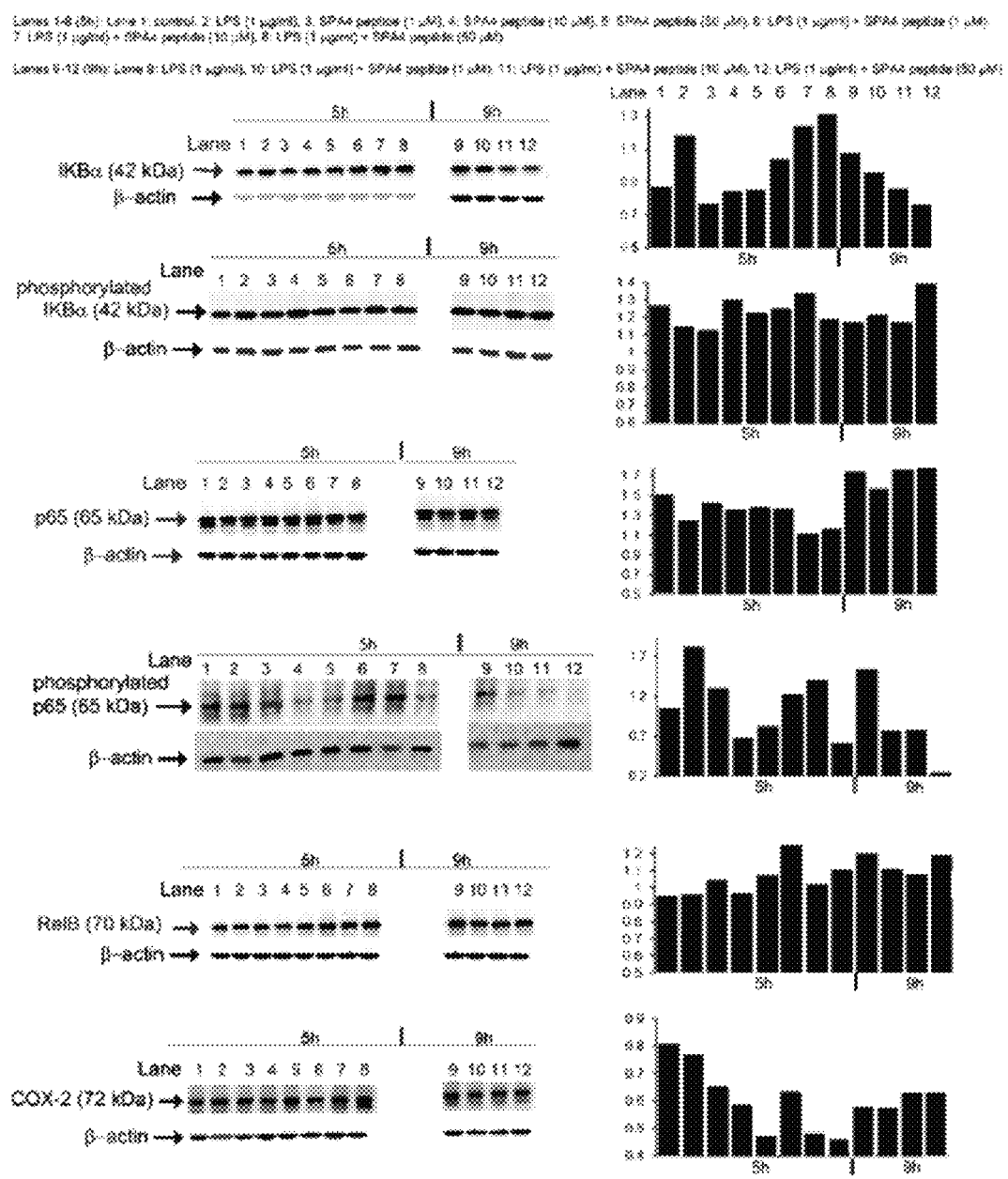
FIG. 24 illustrates the effect of SPA4 peptide on the expression of NF-κB signaling molecules: IKBα, phosphorylated IKBα, p65, phosphorylated p65, RelB and COX-2. Ten µg total cell lysate protein was run on 4-20% Tris-glycine SDS-PAGE gels in partially-reduced condition (heating at 95° C. for 5 minutes, no reducing agent). Separated proteins were immunoblotted with antibodies specific to respective molecules. Images of immune complexes were acquired and bands were analyzed densitometrically. (A) Acquired images of immunoreactive bands of IKBα, phosphorylated IKBα, p65, phosphorylated p65, RelB and COX-2 in SW480 cells treated with LPS±SPA4 peptide on short- and long-term basis (see FIG. 23). (B) Densitometric readings of particular immunoreactive molecule normalized with those of beta-actin (β-actin). β-actin was included as loading control. Results are from one experiment representative of two independent experiments.

As expected, an oscillating expression pattern was observed for the total IKBα, total p65 and COX-2 molecules in short- and long-term LPS-challenged SW480 cells. The SPA4 peptide treatment on short-term basis stimulated an increase in expression of total IKBα, but decrease in phosphorylated p65 and COX-2 expression. The long-term treatment with SPA4 peptide, on the other hand, decreased the total IKBα expression. The expression of phosphorylated p65 and COX-2 remained low. No effect was observed on the expression of phosphorylated IKBα or RelB molecules (FIG. 24).

SPA4 peptide inhibits the intracellular expression of IL-1β and IL-6. Immunoblotting with anti-human IL-1β antibody recognized three major precursor forms (identified as numerals 1, 2 and 3 in FIG. 25) and an active IL-1β (identified as numeral 4 in FIG. 25) in SW480 cell lysates. On comparison of densitometric units, the expression of IL-1β precursor form 1 was found to be increased or unchanged after treatment with SPA4 peptide from that in LPS-treated cells. However, the expression of low molecular weight precursors and active IL-1β was significantly decreased by treatment with SPA4 peptide in a dose-dependent manner at both 5 hours and 9 hours post-LPS treatment models. Similarly, in pre-LPS treatment model, a significant decrease in expression of IL-1β precursor and active forms was observed.

Next, the expression of IL-6 in cell-lysates of SW480 cells treated with LPS±SPA4 peptide was studied. Three major precursor forms of IL-6 (identified as numeral 1 for two reactive bands together and numeral 2 in FIG. 25) and an active form of IL-6 (identified as numeral 3 in FIG. 25) were recognized in immunoblots. The expression of IL-6 precursors or active form of IL-6 was not significantly affected in short-term treatment model. However, when treatment with SPA4 peptide was prolonged for 6 hours or 9 hours in pre- and post-LPS-treatment models, respectively, the IL-6 expression was significantly inhibited.

Figure 26:
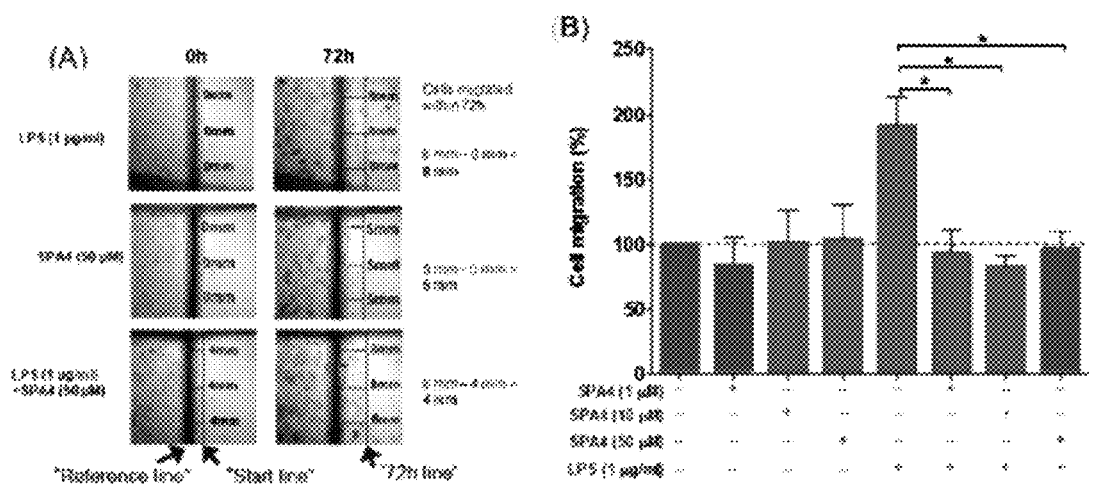
FIG. 26 illustrates the inhibition of LPS-stimulated migration of SW480 cells by SPA4 peptide. (A) Photomicrograph images are shown from one representative of four independent experiments performed at different times. At the beginning of the experiment, a "reference line" (central dark line) and markers were drawn at the bottom of the plate. After scraping, the cells were treated with LPS±SPA4 peptide. On the 0 h images, a "start line" was drawn to represent the starting points for cells. On 72 hours images, a second line was drawn along the edge of cells to represent the migration of cells. (B) Percent cell migration was calculated for LPS±SPA4 peptide-treated cells as compared to untreated control cells for each experiment. The bar chart is mean (SEM) of four independent experiments performed at different times. *$p<0.05$ versus LPS-challenged cells.

SPA4 peptide treatment inhibits the LPS-induced migration of SW480 cells. Increased cell migration is a known characteristic of tumor metastasis. As expected, LPS was found to induce the metastatic property (i.e., cell migration) of SW480 cells. Treatment with the SPA4 peptide inhibited the LPS-induced migration of SW480 cells (FIG. 26). The experiments were designed in a manner that the SPA4 peptide was added to the cells after 4 hours of LPS-treatment, the LPS and SPA4 peptide remained in the medium for the total duration of experiment. Since the inhibitory effect of SPA4 peptide was apparent as early as within 24 hours of treatment (data not shown) and remained consistent till 72 hours of treatment, it appears that the inhibition of migration of SW480 cells is initiated early and is maintained on long term basis.

Figure 27:
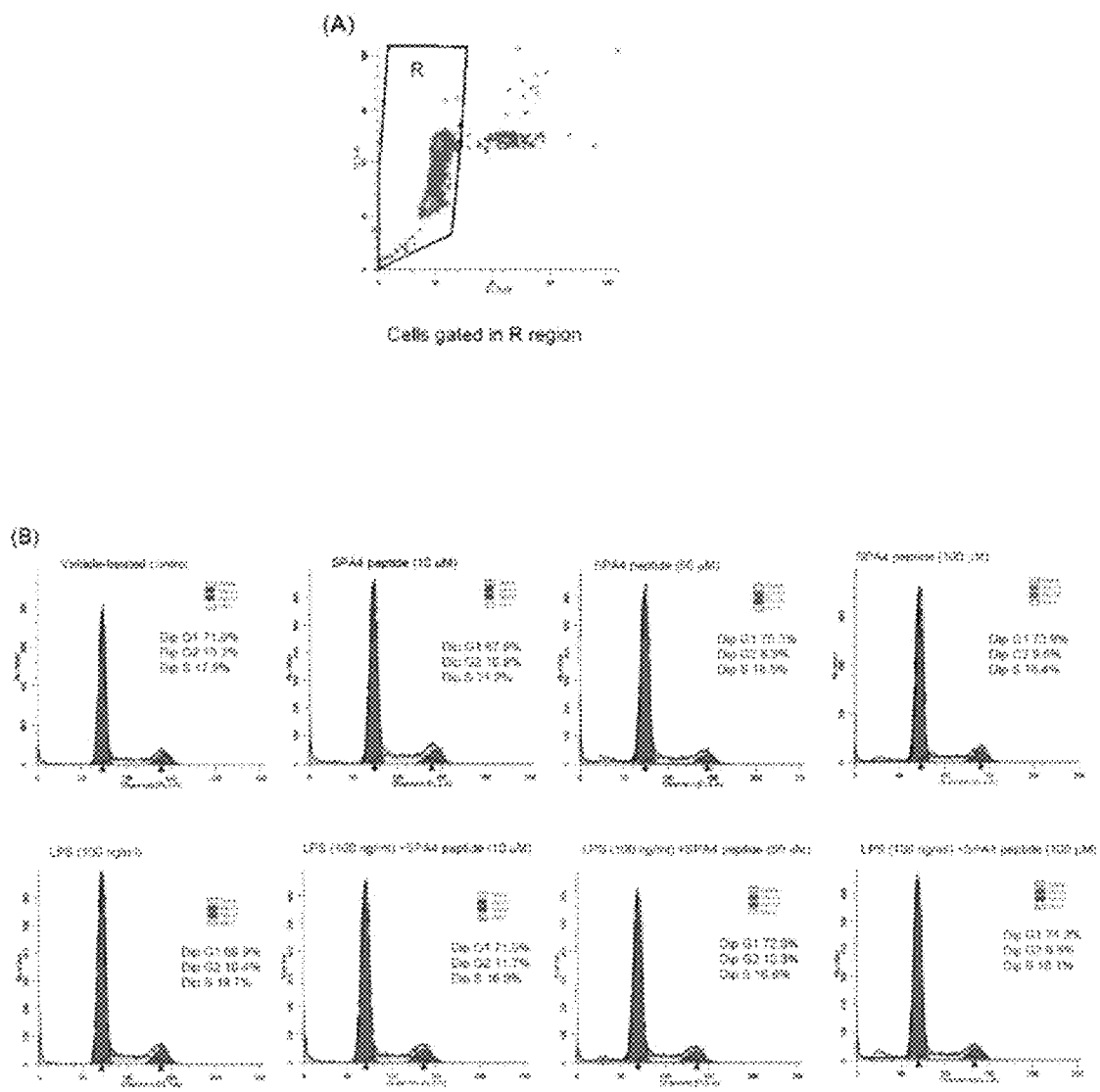
FIG. 27 illustrates the effect of SPA4 peptide on cell cycle progression of SW480 cells. SW480 cells were challenged with LPS (100 ng/ml) for 4 hours following the treatment with SPA4 peptide (10, 50 and 100 µM). After 40 h of total incubation period, cells were harvested, stained with propidium iodide and run on a flow-cytometer. Cell cycle analysis was performed using ModFIT program. The results are from one experiment representative of four independent experiments. (A) Strategy to gate out the cell aggregates by plotting FL3-Width (W) versus FL3-Area (A) dot-plot chart. Single cells are shown within R region. (B) ModFIT program was used to de-convolute the populations of single cells in R region and percentage values of each population are indicated within the chart.
Figure 28:
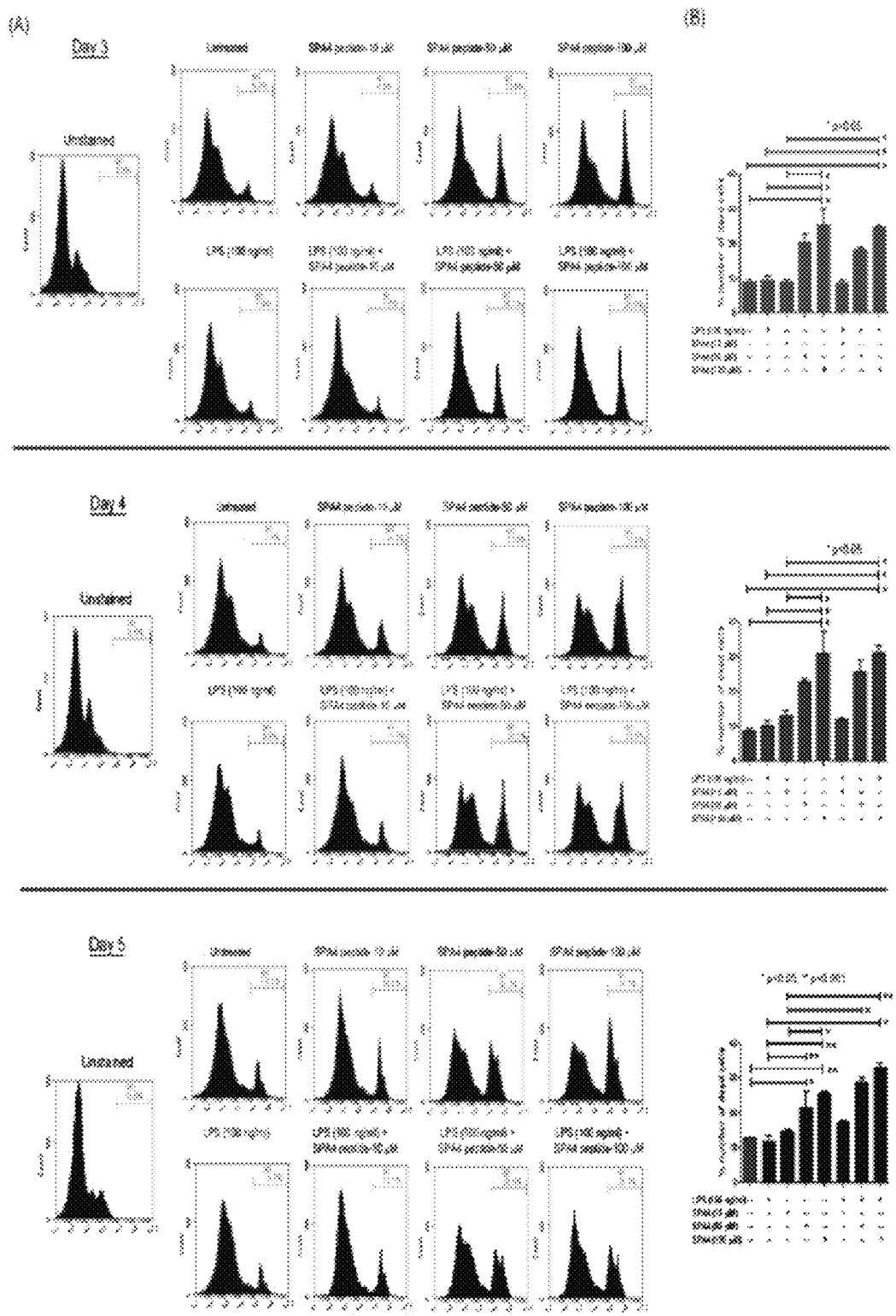
FIG. 28 shows that SPA4 peptide inhibits the viability of SW480 cells. SPA4 peptide inhibits the viability of SW480 cells. SW480 cells were challenged with LPS (100 ng/ml) for 4 hours following the treatment with SPA4 peptide (10, 50 and 100 µM). Cells were harvested after 3, 4 and 5 days of incubation, stained with propidium iodide and run on a flow-cytometer. (A) Percent numbers of dead cells are shown as cells staining positive for propidium iodide in marked region (M1) within histogram charts. The results are from one representative experiment. Unstained cells served as negative control for setting the gate. (B) Results shown here are mean (SEM) percent number of dead cells. Three independent experiments were performed at different times. *$p<0.05$, **$p<0.001$

SPA4 peptide treatment does not affect the cell cycle progression, but inhibits cell viability. It was found that LPS-treatment did not affect cell cycle progression or viability. Treatment with SPA4 peptide (10, 50 and 100 µM concentrations) did not affect the cell cycle progression of SW480 cells over a period of 40 h (FIG. 27). However, the viability of SW480 cells was reduced by SPA4 peptide as compared to untreated or LPS-stimulated cells (about 70% cells viable after SPA4 peptide treatment versus 90% cells viable after LPS- or no-stimulation; FIG. 28). The changes in cell-viability were observed as early as within three days of SPA4 peptide treatment. The inhibition of cell-viability was dependent on the concentration and duration of the treatment with the SPA4 peptide.

Discussion of Example 4

Toll-like receptor 4 (TLR4) has been well-recognized for its critical role in sensing of pathogens or pathogen-derived signals and immune regulation. Although its involvement in cancer has not been fully-established, an increased expression of TLR4 is associated with inflammation induced cancer. Correspondingly, reduced TLR4 activity was found to inhibit inflammatory cytokine secretion, cancer cell proliferation and cancer-associated pain. On the basis of these initial findings, it is proposed herein that TLR4-blocking novel therapeutics will help reduce the inflammation and inflammation-induced cancer-progression. SW480 colorectal cells were utilized as the model system for inflammation-induced cancer progression; the SW480 cells constitutively express TLR4. This Example was focused on studying the effects of a TLR4-interacting SPA4 peptide on TLR4-signaling, inflammatory response, cell migration, cell cycle and viability of SW480 cells.

The SPA4 peptide is derived from an endogenous host-defense protein: surfactant protein-A (SP-A). SP-A is mainly expressed as a component of lung surfactant; its expression has been noted at other mucosal surfaces, such as intestine, skin, eye and urinogenitary systems. In lung, SP-A maintains normal lung function and exerts anti-microbial and anti-inflammatory effects against pathogens and stress-ligands. Since during infection and inflammation, the amounts of SP-A are reduced significantly, an SP-A based surfactant or therapeutic may be of clinical value. It has not been possible to formulate an SP-A-based therapeutic because of its large size and its amenability to degradation. Using computer-modeling and functional screening of a small peptide library, a shorter region of SP-A was identified from the TLR4-interacting region and referred to herein as the SPA4 peptide. Example 2 illustrates that the SPA4 peptide inhibits the LPS-induced inflammatory response in JAWS II dendritic cell line.

Figure 21:
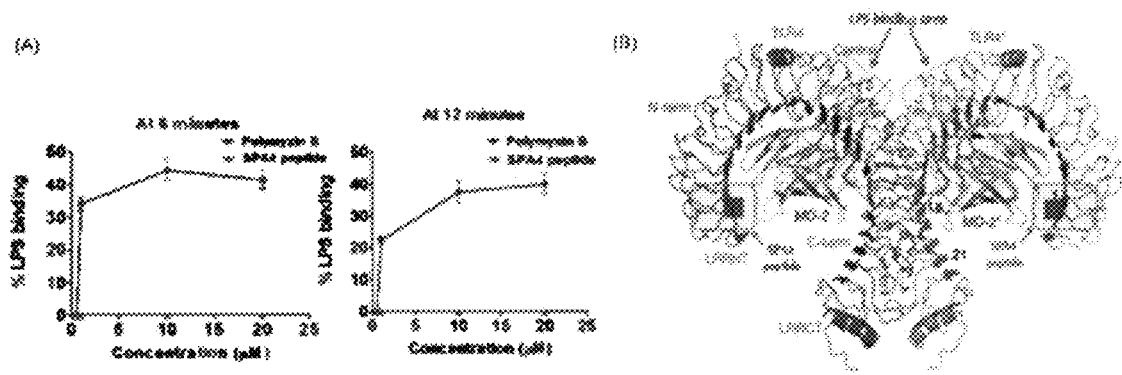
FIG. 21 illustrates binding of SPA4 peptide to LPS-TLR4-MD2. (A) SPA4 peptide does not bind to LPS as measured by Limulus Amoebocyte Lysate (LAL) assay. The assay reaction was read after 6 and 12 minutes of substrate-addition. An equivalent amount of polymyxin B was included as positive control. (B) Computer model of LPS-TLR4-MD2 showing the binding sites of LPS (within yellow shadowed area) and SPA4 peptide (shown within blue shadowed area). LPS, TLR4 and MD2 structures are shown in red, blue/green and grey colors, respectively. This figure is reprinted and adapted by permission from MacMillan Publisher Ltd (Park et al., 2009).

TLR4-signaling is induced in response to a number of endogenous and exogenous ligands, including bacterial LPS. LPS binds to TLR4-MD2 complex and induces inflammatory response via activation of a complex intracellular signaling network. The SW480 cells constitutively express TLR4, and LPS is known to induce inflammatory response, adhesion and migration. Thus, this system was utilized to investigate the effects of SPA4 peptide on LPS-induced TLR4-NF-κB signaling, inflammation and cancer cell properties. In order to understand the mechanism of action of SPA4 peptide, first it was confirmed that the SPA4 peptide does not directly bind to stress-ligand LPS, and the binding site of LPS onto the TLR4-MD2 complex is farther away from the binding site of SPA4 peptide. (FIG. 21). These results indicate that the SPA4 peptide neither binds to LPS nor interferes with the binding of LPS to TLR4-MD2 complex. Furthermore, since SPA4 peptide is hydrophilic (Ko/w=0.56), the SPA4 peptide most likely does not enter into the cytoplasm of the cell by crossing the hydrophobic cell membrane, and does not directly affect the intracellular inflammatory signaling. Overall, these results support the notion that the anti-inflammatory effects of SPA4 peptide are exhibited through its interaction with TLR4.

LPS is known to induce inflammation via activation of TLR4-NF-κB signaling in MYD88-dependent as well as MYD88-independent manner. Full-length SP-A has been identified to inhibit NF-κB activity, but upstream molecular events occurring after SP-A-TLR4 interaction remain unknown. As such, the LPS-TLR4-MD2-signaling is quite complex. Nothing is known in particular for SPA4 peptide. This Example shows that the SPA4 peptide inhibits NF-κB-activity in a MYD88-dependent manner. Furthermore, SPA4 peptide induces the expression of IKBα, an inhibitor of NF-κB, but does not affect the Ser 32-phosphorylated IKBα. The increase in the expression of IKBα is in accordance with the published data on full-length SP-A (Wu et al., 2004). Since NF-κB is composed of five different subunits, c-Rel, RelB, p65, p50 and p52, it was investigated if the stimulation of IKBα translates into the inhibition of these downstream factors. Inhibition of phosphorylation of p65 by SPA4 peptide translates into the inhibition of NF-κB activity (FIG. 24). These results illustrate that SPA4 peptide inhibits the TLR4-NF-κB signaling in response to inflammatory stimuli.

An oscillating pattern of expression of signaling molecules were observed in 5 hour and 9 hour treatment-models; it is possible that different mechanisms in conjunction with NF-κB are affected downstream of the binding of SPA4 peptide to TLR4. In conjunction with the inhibition of NF-κB signaling by SPA4 peptide, a significant decrease in the amounts of LPS-induced IL-1β and IL-6 cytokines were observed. This reduction in inflammatory signaling and cytokine response correlated with inhibition of LPS-induced cell migration. Although a change in cell cycle progression was not observed, significant reduction in cell viability was observed upon treatment with SPA4 peptide. The percent cell-death increased as per the increase in duration and treatment dose of SPA4 peptide. These results will facilitate development of a novel chemopreventive immunotherapeutic to control inflammation-induced cancer progression in patients with colitis.

Example 5

In Example 5, the efficacy of SPA4 peptide in inhibiting LPS-induced acute inflammation was investigated in a mouse model of LPS-inflammation. Balb/c Mice were challenged with E. coli 0111:B4 highly purified, low protein-derived LPS (0.1 or 1 or 15 μg/g body wt) via an intraperitoneal route, one hour prior to treatment with SPA4 peptide (2.5 μg/g body weight) or full-length purified SP-A (0.5 μg/g body weight) via an intraperitoneal route. The mice were monitored for endotoxic-shock like clinical symptoms (including, but not limited to, ruffled fur, eye exudates, diarrhea, prostration, and lack of reactivity), and these symptoms were scored on the basis of severity from 0 to 3, and average clinical symptom indices were calculated for each animal based on the symptom grades (Metkar et al., 2007). Endotoxic-shock like clinical symptoms were noted (at 5 or 7 hours), and mice were sacrificed at different time-intervals after LPS challenge. Major organs and blood specimens were collected. Secreted amounts of TNF-α cytokine were measured in serum and lung tissue homogenates by ELISA method.

At the molecular level, the effects of SPA4 peptide on LPS-induced NF-κB activity were studied in dendritic cells (JAWS II cells) co-transfected with NFκB luciferase reporter plasmid construct and dominant negative construct of MYD88 (an adaptor protein downstream of TLR4; MYD88DN). Briefly, JAWS II dendritic cells (0.5×10$^6$) were transfected with NF-κB luciferase reporter and/or MYD88DN using TransIT-TKO transfection reagent as described earlier (Awasthi S et al., 2003). After 20-24 hours of incubation, the transfected cells were challenged with LPS (100 ng/ml) for 4 hours and treated with SPA4 peptide (10 μM) for 1 hour. After the completion of 5 hours incubation, the cell lysates were prepared in cell lysis buffer and NF-κB-luciferase reporter activity was measured as per the manufacturer's instructions (Promega, WI).

SPA4 peptide inhibits LPS-induced NF-κB activity upstream of MYD88 in dendritic cells. The MYD88 is an intracellular adaptor protein which transduces the LPS-TLR4-signal to NF-κB. Although LPS-TLR4 binding is known to induce NF-κB in MYD88-independent manner also, the inhibition of the NF-κB activity in MYD88–/–-transfected cells by SPA4 peptide was equivalent to that in untreated MYD88–/–-transfected cells against LPS challenge (FIG. 29). These results illustrate that SPA4 peptide does not affect MYD88-independent NF-κB activity. These results are in accordance with the results presented in SW480 cells in Example 4.

The endotoxic shock-like symptoms induced after LPS challenge were measured (Metkar et al., Infect Immun 2007). Results presented in FIG. 30 show that SPA4 peptide and full-length SP-A inhibit the LPS (0.1 μg/g body weight)-induced clinical symptoms.

LPS is known to induce the secretion of TNF-α, and a significant amount is detected in the blood. In FIG. 31, it was found that LPS (0.1 μg/g body weight)-induced circulatory TNF-α amounts are reduced after treatment with SPA4 peptide and full-length SP-A. The results are in accordance with published data in the literature on anti-inflammatory effects of full-length SP-A (Borron P et al., Am J Physiol Lung Cell Mol Physiol, 2000. 278: L840-847). Similar to SP-A, SPA4 peptide also inhibited LPS-induced TNF-alpha in vivo through its interaction with TLR4 and suppression of NF-κB activity. Also, these results corroborate with findings presented in Examples 2 and 3.

Figure 32:
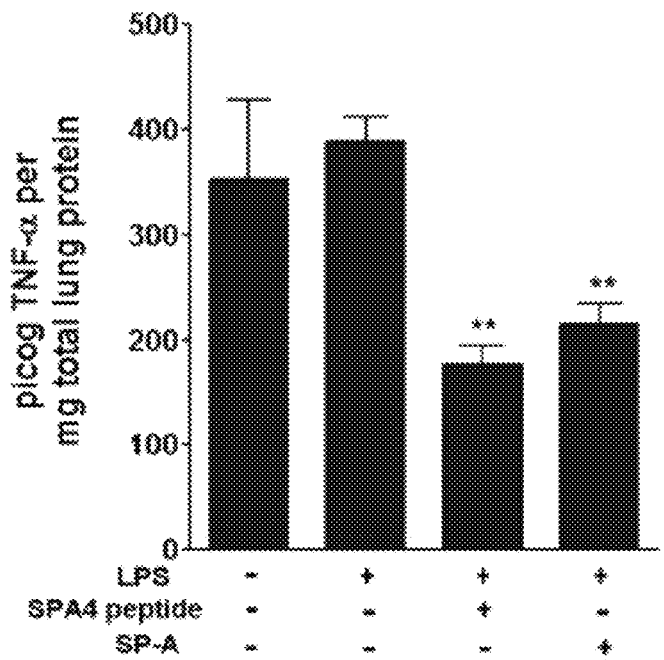
FIG. 32 illustrates that SPA4 peptide treatment reduces the LPS-induced TNF-α levels in lung tissue homogenates. Mice were challenged with 1 µg LPS per g body weight intraperitoneally at 0 h and treated with SPA4 peptide (2.5 µg/g body wt) or SP-A (Malt baboon SP-A, 0.5 µg/g body wt) at 1 hour, and sacrificed at 5 hours. Lung tissues were harvested at the time of sacrifice. TNF-alpha levels were measured in lung tissue homogenates by ELISA, and normalized with total lung tissue homogenate protein. Mean (SEM) pg TNF-alpha amounts per mg total lung protein are shown within the bar chart.
Figure 33:
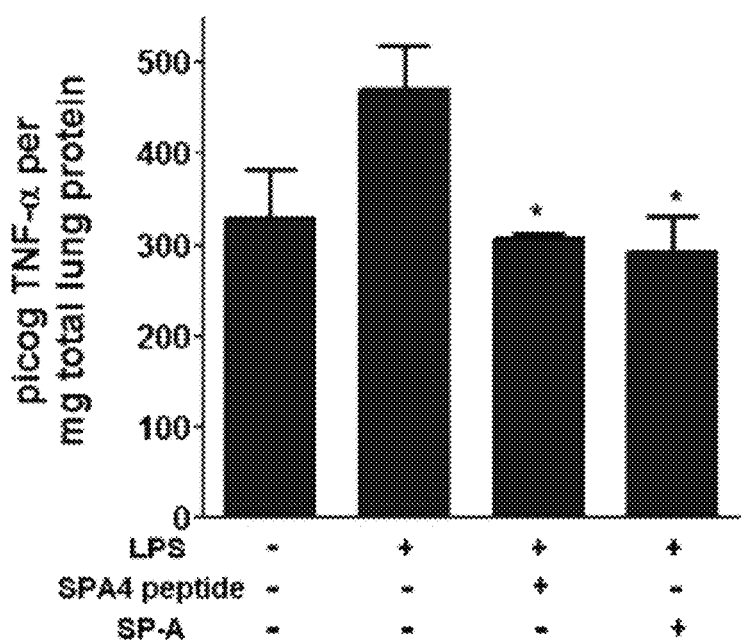
FIG. 33 illustrates a High-dose LPS Challenge model. Mice were challenged with 15 µg LPS per g body weight intraperitoneally at 0 h and treated with SPA4 peptide (2.5 µg/g body wt) or SP-A (Malt baboon SP-A, 0.5 µg/g body wt) at 1 hour, and sacrificed at 5 hours. Lung tissues were harvested at the time of sacrifice. TNF-alpha levels were measured in lung tissue homogenates by ELISA, and normalized with total lung tissue homogenate protein. Mean (SEM) pg TNF-alpha amounts per mg total lung protein are shown within the bar chart.

SPA4 peptide treatment also reduced LPS-induced TNF-α levels in lung tissue homogenates. FIGS. 32 and 33 illustrate that the amounts of LPS-induced TNF-alpha are low in lung tissues of mice challenged with LPS (1 μg/g body weight or 15 μg/g body weight) and treated with full-length SP-A and SPA4 peptide. Similar observations are expected for SPA4 peptide inhibition of the inflammatory response in other organs.

In summary, the results show that the treatment with SPA4 peptide inhibited NF-κB luciferase activity in dendritic cells, inflammatory symptoms, and TNFα levels in serum and lung tissue homogenates of mice against LPS stimuli. Moreover, the inhibition of LPS-induced NF-κB activity by SPA4 peptide was indistinguishable from those challenged with LPS alone, in absence of functional MYD88. Taken together, the results indicate that the SPA4 peptide exerts its inhibitory effect on the TLR-NF-κB pathway upstream of MYD88 adaptor protein and thereby regulates the TNFα response.

Thus, in accordance with the present invention, there have been provided compositions, as well as methods of producing and using same, that fully satisfy the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

REFERENCES

The following references, to the extent that they provide exemplary procedural or other details supplementary to those set forth herein, are specifically incorporated herein by reference.

Abreu et al. (2002) *J Biol Chem* 277:20431-7.
Ackerman et al. (2003) *J Immunol.* 170:4178-88.
Alcorn et al. *Am J Physiol Lung Cell Mol Physiol* 289:L1113-1122.
Armstrong et al. (2004) *Am J Respir Cell Mol Biol* 31:241-245.
Awasthi S (2010) *Recent Pat Antiinfect Drug Discov* 5:115-123.
Awasthi et al. (2005) *J Immunol* 175:3900-3906.
Awasthi et al. (1999) *Am J Respir Crit Care Med* 160:942-949.

Awasthi et al. (2001) *Am J Respir Crit Care Med* 163:389-397.
Awasthi et al. (2003) *Biotechniques* 35:600-602, 604.
Awasthi et al. (2006) *Cell Immunol* 240:31-40.
Awasthi et al. (2008) *Dev Comp Immunol* 32:1088-1098.
Awasthi et al. (2004) *Respir Res* 5:28.
Awasthi et al. (2009) *Immunol Cell Biol.* 87:419-27.
Banks et al. (1999) *J Comp Pathol.* 120:1-13.
Barton et al. (2007) *Sem in Immunol* 19:33-40.
Basu S et al. (2004) *Am J Physiol Lung Cell Mol Physiol* 286:L887-892.
Berman et al. (2000) *Nucleic Acids Res* 28:235-242.
Bharadwaj et al. (2005) *J Surg Res.* 127:29-38.
Blander J M (2007) *Cell Microbiol.* 9:290-9.
Blander J M (2008) *Ann Rheum Dis.* 67 Suppl 3:iii44-9.
Bosani et al. (2009) *Biologics* 3:77-97.
Brinker et al. (2003) *Am J Physiol Lung Cell Mol Physiol* 284:L232-241.
Carpenter et al. (2009) *Biochem. J.* 422:1-10.
Chang et al. (2006) *J Immunol* 176:3010-3018.
Darnell et al. (2007) *Proteins* 68:813-823.
De Jager et al. *Genes Immun* 8:387-97.
Diao et al. (2006) *J Immunol.* 176:7196-206.
Edwards D A (2004) *J Math Biol* 49:272-292.
Edwards D A (2006) *Bull Math Biol* 68:627-654.
Fach et al. (2007) *Viral Immunol.* 20:119-30.
Fajardo-Moser et al. (2008) *Int J Med Microbiol.* 298:11-20.
Famuyide et al. (2009) *Pediatr Res.* 66:162-7.
Fukata et al. (2005) *Am J Physiol Gastrointest Liver Physiol* 288:G1055-65.
Gagro et al. (2004) *Clin Exp Immunol* 135:267-272.
Giamcometti et al. (2004) *Am J Respir Crit Care Med.,* 169:187-194.
Gil et al. (2009) *J Biol Chem* 284:7495-7504.
Goldmann et al. (2009) *Diagn Pathol.* 4:8.
Gordon et al. (2002) *Aliment Pharmacol Ther* 16:699-705.
Guan et al. (2009) *Vaccine* 27:7096-104.
Guidi et al. (2010) *Eur Rev Med Pharmacol Sci* 14:342-6.
Guillot et al. (2002) *J Immunol* 168:5989-5992.
Guillot et al. (2004) *J Biol Chem* 279:2712-2718.
Hanauer S B (2010) *Nat Rev Gastroenterol Hepatol* 7:63-4.
Hartshorn K L (2010) *Front Biosci* (Schol Ed) 2:527-46.
He et al. (2009) *Respir Res* 10:126.
Head et al. (2003) *J Biol Chem* 278:43254-43260.
Henning et al. (2008) *J Immunol* 180:7847-7858.
Hoebe et al. (2006) *Curr Pharm Des* 12:4123-4134.
Holt et al. (1995) *Adv Exp Med. Biol.* 378:177-81.
Hulette et al. (2001) *Arch Dermatol Res.* 293:147-58.
Humphrey et al. (1996) *J Mol Graph* 14:33-38, 27-38.
Inaba et al. (1998) *J Exp Med* 188:2163-2173.
Iwami et al. (2000) *J Immunol.* 165:6682-6.
Jain et al. (2008) *Blood.*
Johansson et al. (1997) *Eur J Biochem* 244:675-693.
Kajikawa et al. (2005) *Gene* 344:193-202.
Kawai et al. (2007) *Semin Immunol* 19:24-32.
King et al. (1972) *Am J Physiol* 223:715-726.
Kingma et al. (2006) *Curr Opin Pharmacol.* 6:277-83.
Kramer et al. (2003) *Pediatr Res.* 54:52-7.
Kramer et al. (2009) *Innate Immun.* 15:101-7.
Kramer et al. (2009) *Semin Fetal Neonatal Med.* 14:2-7.
Kuroki et al. (2007) *Cell Microbiol* 9:1871-1879.
Kuzmenko et al. (2005) *J Biol Chem.* 280:25913-9.
Leaphart et al. (2007) *J Immunol* 179:4808-20.
Lee et al. (2010) *J Immunol.* 184:6479-91.
Lommatzsch et al. (2007) *Eur Respir J.* 30:878-86.
Lv et al. (2009) *J Trauma* 66:124-131.
Madan et al. (2010) *Mol Immunol.* 47:1923-30.
Maes et al. (2006) *Int Arch Allergy Immunol* 141:354-368.
Masten et al. (2006) *J Immunol.* 177:7784-93.
Medzhitov et al. (1998) *Mol. Cell.* 2:253-258.
Melmed et al. (2010) *Nat Rev Gastroenterol Hepatol* 7:110-7.
Metkar et al. (2007) *Infect Immun.,* 75:5415-5424.
Miyake K (2007) *Semin Immunol* 19:3-10.
Myszka et al. (1998) *Anal Biochem* 265:326-330.
Ochs et al. (2002) *Am J Respir Cell Mol. Biol.* 26:91-8.
Ohteki T (2007) *Allergol Int.* 56:209-14.
Ohya et al. (2006) *Biochemistry.* 45:8657-64.
Okogbule-Wonodi et al. (2010) *Innate Immun.*
Palaniyar et al. (2000) *Biochemistry* 39:6310-6316.
Park et al. (2009) *Nature* 458:1191-1195.
Pastva et al. (2007) *Proc Am Thorac Soc* 4:252-257.
Re et al. (2002) *J Biol Chem* 277:23427-23432.
Sabatte et al. (2007) *Cytokine Growth Factor Rev.* 18:5-17.
Sano et al. (2005) *Mol Immunol.* 42:279-87.
Schneidman-Duhovny et al. (2005a) *Proteins* 60:224-231.
Schneidman-Duhovny et al. (2005b) *Nucleic Acids Res* 33:W363-367.
Stevens et al. (1995) *Biochem J* 308 (Pt 1):77-81.
Strayer et al. (1993) *J Biol Chem* 268:18679-18684.
Torok et al. (2004) *Clin Immunol* 112:85-91.
Tovchigrechko et al. (2006) *Nucleic Acids Res* 34:W310-314.
van Vliet et al. (2007) *Curr Opin Immunol.* 19:435-40.
Vilekar et al. (2010) In *American Association of Immunologists,* pp. Abstract. Baltimore.
Villar et al. (2010) *Respir Res* 11:27.
Webb et al. (2005) *Crit Rev Immunol.* 25:465-91.
Wissel et al. (1996) *Am J Physiol* 271:L432-440.
Wright J R (1997) *Physiol Rev* 77:931-962.
Wright J R (2004) *Biol Neonate.* 85:326-32.
Wu et al. (2004) *Am J Respir Cell Mol Biol.* 31:587-594.
Yamada et al. (2006) *J Biol Chem* 281:21771-21780.
Yang et al. (2005) *J Biol Chem* 280:34447-34457.

What is claimed is:

1. A composition, comprising an isolated peptide fragment of SEQ ID NO:1, wherein the peptide fragment is less than 50 amino acids in length and comprises the amino acid sequence as set forth in SEQ ID NO:3, and wherein the isolated peptide binds to Toll-like receptor-4 (TLR-4).

2. The composition of claim 1, wherein the peptide fragment comprises a portion of the C-terminal carbohydrate recognition domain of SEQ ID NO:1.

3. The composition of claim 1, wherein the peptide fragment is less than 40 amino acids in length.

4. The composition of claim 1, wherein the peptide fragment is less than 30 amino acids in length.

5. The composition of claim 1, wherein the peptide fragment is less than 25 amino acids in length.

6. The composition of claim 1, wherein the peptide fragment is 20 amino acids in length.

7. A composition, comprising an isolated peptide that binds to TLR-4, the isolated peptide comprising amino acids 12-19 of SEQ ID NO:3 and wherein the isolated peptide comprises an amino acid sequence that differs by one or two amino acids from SEQ ID NO:3.

8. A pharmaceutical composition comprising a pharmaceutically acceptable carrier and an isolated peptide having an amino acid sequence that differs by one or two amino acids from SEQ ID NO:3 and comprises amino acids 12-19 of SEQ ID NO:3, and wherein the isolated peptide binds to TLR-4.

* * * * *

UNITED STATES PATENT AND TRADEMARK OFFICE
CERTIFICATE OF CORRECTION

PATENT NO.        : 8,623,832 B2
APPLICATION NO.   : 13/289820
DATED             : January 7, 2014
INVENTOR(S)       : Shanjana Awasthi Page 1 of 1

It is certified that error appears in the above-identified patent and that said Letters Patent is hereby corrected as shown below:

In the Specification:
Column 1, line 52: Delete "bronchioalveolar" and replace with -- bronchoalveolar --
Column 6, line 6: Delete "(SEQ ID NO:31" and replace with -- (SEQ ID NO:3) --
Column 22, line 59: Delete "bronchioalveolar" and replace with -- bronchoalveolar --
Column 22, line 61: Delete "bronchioalveolar" and replace with -- bronchoalveolar --
Column 23, line 2: Delete "dilapidated" and replace with -- delipidated --
Column 25, line 35: Delete "S-well" and replace with -- 8-well --
Column 27, line 43: Delete "bronchioalveolar" and replace with -- bronchoalveolar --
Column 30, line 45: Delete "bronchioalveolar" and replace with -- bronchoalveolar --
Column 31, line 22: Delete "bronchioalveolar" and replace with -- bronchoalveolar --
Column 32, line 39: Delete "bronchioalveolar" and replace with -- bronchoalveolar --
Column 32, line 41: Delete "bronchioalveolar" and replace with -- bronchoalveolar --
Column 32, line 49: Delete "dilapidated" and replace with -- delipidated --
Column 35, line 59: Delete "bronchioalveolar" and replace with -- bronchoalveolar --
Column 44, line 41: Delete "AOD" and replace with -- ΔOD --
Column 46, line 30: Delete "3-mercaptoethanol" and replace with -- β-mercaptoethanol --

Signed and Sealed this
First Day of April, 2014

Michelle K. Lee
*Deputy Director of the United States Patent and Trademark Office*

SEQUENCE LISTING

<160> NUMBER OF SEQ ID NOS: 261

<210> SEQ ID NO 1
<211> LENGTH: 248
<212> TYPE: PRT
<213> ORGANISM: Homo sapiens

<400> SEQUENCE: 1

Met Trp Leu Cys Pro Leu Ala Leu Asn Leu Ile Leu Met Ala Ala Ser
1               5                   10                  15

-continued

```
Gly Ala Val Cys Glu Val Lys Asp Val Cys Val Gly Ser Pro Gly Ile
             20                  25                  30
Pro Gly Thr Pro Gly Ser His Gly Leu Pro Gly Arg Asp Gly Arg Asp
         35                  40                  45
Gly Leu Lys Gly Asp Pro Gly Pro Pro Gly Met Gly Pro Pro Gly
 50                  55                  60
Glu Met Pro Cys Pro Pro Gly Asn Asp Gly Leu Pro Gly Ala Pro Gly
 65                  70                  75                  80
Ile Pro Gly Glu Cys Gly Lys Gly Glu Pro Gly Glu Arg Gly Pro
                 85                  90                  95
Pro Gly Leu Pro Ala His Leu Asp Glu Glu Leu Gln Ala Thr Leu His
             100                 105                 110
Asp Phe Arg His Gln Ile Leu Gln Thr Arg Gly Ala Leu Ser Leu Gln
             115                 120                 125
Gly Ser Ile Met Thr Val Gly Glu Lys Val Phe Ser Ser Asn Gly Gln
 130                 135                 140
Ser Ile Thr Phe Asp Ala Ile Gln Glu Ala Cys Ala Arg Ala Gly Gly
 145                 150                 155                 160
Arg Ile Ala Val Pro Arg Asn Pro Glu Glu Asn Glu Ala Ile Ala Ser
                 165                 170                 175
Phe Val Lys Lys Tyr Asn Thr Tyr Ala Tyr Val Gly Leu Thr Glu Gly
             180                 185                 190
Pro Ser Pro Gly Asp Phe Arg Tyr Ser Asp Gly Thr Pro Val Asn Tyr
             195                 200                 205
Thr Asn Trp Tyr Arg Gly Glu Pro Ala Gly Arg Gly Lys Glu Gln Cys
 210                 215                 220
Val Glu Met Tyr Thr Asp Gly Gln Trp Asn Asp Arg Asn Cys Leu Tyr
225                 230                 235                 240
Ser Arg Leu Thr Ile Cys Glu Phe
                 245

<210> SEQ ID NO 2
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: 3-9 amino acids; each position may contain any
      amino acid

<400> SEQUENCE: 2

Asn Tyr Thr Xaa Arg Gly
1               5

<210> SEQ ID NO 3
<211> LENGTH: 20
<212> TYPE: PRT
<213> ORGANISM: Homo sapiens

<400> SEQUENCE: 3

Gly Asp Phe Arg Tyr Ser Asp Gly Thr Pro Val Asn Tyr Thr Asn Trp
1               5                   10                  15

Tyr Arg Gly Glu
            20

<210> SEQ ID NO 4
<211> LENGTH: 20
<212> TYPE: PRT
<213> ORGANISM: Homo sapiens
```

-continued

<400> SEQUENCE: 4

Val Asn Tyr Thr Asn Trp Tyr Arg Gly Glu Pro Ala Gly Arg Gly Lys
1               5                   10                  15

Glu Gln Cys Val
            20

<210> SEQ ID NO 5
<211> LENGTH: 20
<212> TYPE: PRT
<213> ORGANISM: Homo sapiens

<400> SEQUENCE: 5

Tyr Val Gly Leu Thr Glu Gly Pro Ser Pro Gly Asp Phe Arg Tyr Ser
1               5                   10                  15

Asp Gly Thr Pro
            20

<210> SEQ ID NO 6
<211> LENGTH: 20
<212> TYPE: PRT
<213> ORGANISM: Homo sapiens

<400> SEQUENCE: 6

Gly Ala Phe Arg Tyr Ser Asp Gly Thr Pro Val Asn Tyr Thr Asn Trp
1               5                   10                  15

Tyr Arg Gly Glu
            20

<210> SEQ ID NO 7
<211> LENGTH: 10
<212> TYPE: PRT
<213> ORGANISM: Homo sapiens

<400> SEQUENCE: 7

Gly Asp Phe Arg Tyr Ser Asp Gly Thr Pro
1               5                   10

<210> SEQ ID NO 8
<211> LENGTH: 5
<212> TYPE: PRT
<213> ORGANISM: Homo sapiens

<400> SEQUENCE: 8

Gly Asp Phe Arg Tyr
1               5

<210> SEQ ID NO 9
<211> LENGTH: 5
<212> TYPE: PRT
<213> ORGANISM: Homo sapiens

<400> SEQUENCE: 9

Asp Phe Arg Tyr Ser
1               5

<210> SEQ ID NO 10
<211> LENGTH: 5
<212> TYPE: PRT
<213> ORGANISM: Homo sapiens

<400> SEQUENCE: 10

Phe Arg Tyr Ser Asp
1               5

```
<210> SEQ ID NO 11
<211> LENGTH: 5
<212> TYPE: PRT
<213> ORGANISM: Homo sapiens

<400> SEQUENCE: 11

Arg Tyr Ser Asp Gly
1               5

<210> SEQ ID NO 12
<211> LENGTH: 5
<212> TYPE: PRT
<213> ORGANISM: homo sapiens

<400> SEQUENCE: 12

Tyr Ser Asp Gly Thr
1               5

<210> SEQ ID NO 13
<211> LENGTH: 5
<212> TYPE: PRT
<213> ORGANISM: homo sapiens

<400> SEQUENCE: 13

Ser Asp Gly Thr Pro
1               5

<210> SEQ ID NO 14
<211> LENGTH: 5
<212> TYPE: PRT
<213> ORGANISM: homo sapiens

<400> SEQUENCE: 14

Asp Gly Thr Pro Val
1               5

<210> SEQ ID NO 15
<211> LENGTH: 5
<212> TYPE: PRT
<213> ORGANISM: homo sapiens

<400> SEQUENCE: 15

Gly Thr Pro Val Asn
1               5

<210> SEQ ID NO 16
<211> LENGTH: 5
<212> TYPE: PRT
<213> ORGANISM: homo sapiens

<400> SEQUENCE: 16

Thr Pro Val Asn Tyr
1               5

<210> SEQ ID NO 17
<211> LENGTH: 5
<212> TYPE: PRT
<213> ORGANISM: homo sapiens

<400> SEQUENCE: 17

Pro Val Asn Tyr Thr
1               5

<210> SEQ ID NO 18
```

```
<211> LENGTH: 5
<212> TYPE: PRT
<213> ORGANISM: homo sapiens

<400> SEQUENCE: 18

Val Asn Tyr Thr Asn
1               5

<210> SEQ ID NO 19
<211> LENGTH: 5
<212> TYPE: PRT
<213> ORGANISM: homo sapiens

<400> SEQUENCE: 19

Asn Tyr Thr Asn Trp
1               5

<210> SEQ ID NO 20
<211> LENGTH: 5
<212> TYPE: PRT
<213> ORGANISM: homo sapiens

<400> SEQUENCE: 20

Tyr Thr Asn Trp Tyr
1               5

<210> SEQ ID NO 21
<211> LENGTH: 5
<212> TYPE: PRT
<213> ORGANISM: homo sapiens

<400> SEQUENCE: 21

Thr Asn Trp Tyr Arg
1               5

<210> SEQ ID NO 22
<211> LENGTH: 5
<212> TYPE: PRT
<213> ORGANISM: homo sapiens

<400> SEQUENCE: 22

Asn Trp Tyr Arg Gly
1               5

<210> SEQ ID NO 23
<211> LENGTH: 5
<212> TYPE: PRT
<213> ORGANISM: Homo sapiens

<400> SEQUENCE: 23

Trp Tyr Arg Gly Glu
1               5

<210> SEQ ID NO 24
<211> LENGTH: 6
<212> TYPE: PRT
<213> ORGANISM: homo sapiens

<400> SEQUENCE: 24

Gly Asp Phe Arg Tyr Ser
1               5

<210> SEQ ID NO 25
<211> LENGTH: 6
<212> TYPE: PRT
<213> ORGANISM: homo sapiens
```

<400> SEQUENCE: 25

Asp Phe Arg Tyr Ser Asp
1               5

<210> SEQ ID NO 26
<211> LENGTH: 6
<212> TYPE: PRT
<213> ORGANISM: homo sapiens

<400> SEQUENCE: 26

Phe Arg Tyr Ser Asp Gly
1               5

<210> SEQ ID NO 27
<211> LENGTH: 6
<212> TYPE: PRT
<213> ORGANISM: homo sapiens

<400> SEQUENCE: 27

Arg Tyr Ser Asp Gly Thr
1               5

<210> SEQ ID NO 28
<211> LENGTH: 6
<212> TYPE: PRT
<213> ORGANISM: homo sapiens

<400> SEQUENCE: 28

Tyr Ser Asp Gly Thr Pro
1               5

<210> SEQ ID NO 29
<211> LENGTH: 6
<212> TYPE: PRT
<213> ORGANISM: homo sapiens

<400> SEQUENCE: 29

Ser Asp Gly Thr Pro Val
1               5

<210> SEQ ID NO 30
<211> LENGTH: 6
<212> TYPE: PRT
<213> ORGANISM: homo sapiens

<400> SEQUENCE: 30

Asp Gly Thr Pro Val Asn
1               5

<210> SEQ ID NO 31
<211> LENGTH: 6
<212> TYPE: PRT
<213> ORGANISM: homo sapiens

<400> SEQUENCE: 31

Gly Thr Pro Val Asn Tyr
1               5

<210> SEQ ID NO 32
<211> LENGTH: 6
<212> TYPE: PRT
<213> ORGANISM: homo sapiens

<400> SEQUENCE: 32

```
Thr Pro Val Asn Tyr Thr
1               5

<210> SEQ ID NO 33
<211> LENGTH: 6
<212> TYPE: PRT
<213> ORGANISM: homo sapiens

<400> SEQUENCE: 33

Pro Val Asn Tyr Thr Asn
1               5

<210> SEQ ID NO 34
<211> LENGTH: 6
<212> TYPE: PRT
<213> ORGANISM: homo sapiens

<400> SEQUENCE: 34

Val Asn Tyr Thr Asn Trp
1               5

<210> SEQ ID NO 35
<211> LENGTH: 6
<212> TYPE: PRT
<213> ORGANISM: homo sapiens

<400> SEQUENCE: 35

Asn Tyr Thr Asn Trp Tyr
1               5

<210> SEQ ID NO 36
<211> LENGTH: 6
<212> TYPE: PRT
<213> ORGANISM: homo sapiens

<400> SEQUENCE: 36

Tyr Thr Asn Trp Tyr Arg
1               5

<210> SEQ ID NO 37
<211> LENGTH: 6
<212> TYPE: PRT
<213> ORGANISM: homo sapiens

<400> SEQUENCE: 37

Thr Asn Trp Tyr Arg Gly
1               5

<210> SEQ ID NO 38
<211> LENGTH: 6
<212> TYPE: PRT
<213> ORGANISM: homo sapiens

<400> SEQUENCE: 38

Asn Trp Tyr Arg Gly Glu
1               5

<210> SEQ ID NO 39
<211> LENGTH: 7
<212> TYPE: PRT
<213> ORGANISM: homo sapiens

<400> SEQUENCE: 39

Gly Asp Phe Arg Tyr Ser Asp
1               5
```

```
<210> SEQ ID NO 40
<211> LENGTH: 7
<212> TYPE: PRT
<213> ORGANISM: homo sapiens

<400> SEQUENCE: 40

Asp Phe Arg Tyr Ser Asp Gly
1               5

<210> SEQ ID NO 41
<211> LENGTH: 7
<212> TYPE: PRT
<213> ORGANISM: homo sapiens

<400> SEQUENCE: 41

Phe Arg Tyr Ser Asp Gly Thr
1               5

<210> SEQ ID NO 42
<211> LENGTH: 7
<212> TYPE: PRT
<213> ORGANISM: homo sapiens

<400> SEQUENCE: 42

Arg Tyr Ser Asp Gly Thr Pro
1               5

<210> SEQ ID NO 43
<211> LENGTH: 7
<212> TYPE: PRT
<213> ORGANISM: homo sapiens

<400> SEQUENCE: 43

Tyr Ser Asp Gly Thr Pro Val
1               5

<210> SEQ ID NO 44
<211> LENGTH: 7
<212> TYPE: PRT
<213> ORGANISM: homo sapiens

<400> SEQUENCE: 44

Ser Asp Gly Thr Pro Val Asn
1               5

<210> SEQ ID NO 45
<211> LENGTH: 7
<212> TYPE: PRT
<213> ORGANISM: homo sapiens

<400> SEQUENCE: 45

Asp Gly Thr Pro Val Asn Tyr
1               5

<210> SEQ ID NO 46
<211> LENGTH: 7
<212> TYPE: PRT
<213> ORGANISM: homo sapiens

<400> SEQUENCE: 46

Gly Thr Pro Val Asn Tyr Thr
1               5

<210> SEQ ID NO 47
<211> LENGTH: 7
```

```
<212> TYPE: PRT
<213> ORGANISM: homo sapiens

<400> SEQUENCE: 47

Thr Pro Val Asn Tyr Thr Asn
1               5

<210> SEQ ID NO 48
<211> LENGTH: 7
<212> TYPE: PRT
<213> ORGANISM: homo sapiens

<400> SEQUENCE: 48

Pro Val Asn Tyr Thr Asn Trp
1               5

<210> SEQ ID NO 49
<211> LENGTH: 7
<212> TYPE: PRT
<213> ORGANISM: homo sapiens

<400> SEQUENCE: 49

Val Asn Tyr Thr Asn Trp Tyr
1               5

<210> SEQ ID NO 50
<211> LENGTH: 7
<212> TYPE: PRT
<213> ORGANISM: homo sapiens

<400> SEQUENCE: 50

Asn Tyr Thr Asn Trp Tyr Arg
1               5

<210> SEQ ID NO 51
<211> LENGTH: 7
<212> TYPE: PRT
<213> ORGANISM: homo sapiens

<400> SEQUENCE: 51

Tyr Thr Asn Trp Tyr Arg Gly
1               5

<210> SEQ ID NO 52
<211> LENGTH: 7
<212> TYPE: PRT
<213> ORGANISM: homo sapiens

<400> SEQUENCE: 52

Thr Asn Trp Tyr Arg Gly Glu
1               5

<210> SEQ ID NO 53
<211> LENGTH: 8
<212> TYPE: PRT
<213> ORGANISM: homo sapiens

<400> SEQUENCE: 53

Gly Asp Phe Arg Tyr Ser Asp Gly
1               5

<210> SEQ ID NO 54
<211> LENGTH: 8
<212> TYPE: PRT
<213> ORGANISM: homo sapiens
```

```
<400> SEQUENCE: 54

Asp Phe Arg Tyr Ser Asp Gly Thr
1               5

<210> SEQ ID NO 55
<211> LENGTH: 8
<212> TYPE: PRT
<213> ORGANISM: homo sapiens

<400> SEQUENCE: 55

Phe Arg Tyr Ser Asp Gly Thr Pro
1               5

<210> SEQ ID NO 56
<211> LENGTH: 8
<212> TYPE: PRT
<213> ORGANISM: homo sapiens

<400> SEQUENCE: 56

Arg Tyr Ser Asp Gly Thr Pro Val
1               5

<210> SEQ ID NO 57
<211> LENGTH: 8
<212> TYPE: PRT
<213> ORGANISM: homo sapiens

<400> SEQUENCE: 57

Tyr Ser Asp Gly Thr Pro Val Asn
1               5

<210> SEQ ID NO 58
<211> LENGTH: 8
<212> TYPE: PRT
<213> ORGANISM: homo sapiens

<400> SEQUENCE: 58

Ser Asp Gly Thr Pro Val Asn Tyr
1               5

<210> SEQ ID NO 59
<211> LENGTH: 8
<212> TYPE: PRT
<213> ORGANISM: homo sapiens

<400> SEQUENCE: 59

Asp Gly Thr Pro Val Asn Tyr Thr
1               5

<210> SEQ ID NO 60
<211> LENGTH: 8
<212> TYPE: PRT
<213> ORGANISM: homo sapiens

<400> SEQUENCE: 60

Gly Thr Pro Val Asn Tyr Thr Asn
1               5

<210> SEQ ID NO 61
<211> LENGTH: 8
<212> TYPE: PRT
<213> ORGANISM: homo sapiens

<400> SEQUENCE: 61

Thr Pro Val Asn Tyr Thr Asn Trp
```

<210> SEQ ID NO 62
<211> LENGTH: 8
<212> TYPE: PRT
<213> ORGANISM: homo sapiens

<400> SEQUENCE: 62

Pro Val Asn Tyr Thr Asn Trp Tyr
1               5

<210> SEQ ID NO 63
<211> LENGTH: 8
<212> TYPE: PRT
<213> ORGANISM: homo sapiens

<400> SEQUENCE: 63

Val Asn Tyr Thr Asn Trp Tyr Arg
1               5

<210> SEQ ID NO 64
<211> LENGTH: 8
<212> TYPE: PRT
<213> ORGANISM: homo sapiens

<400> SEQUENCE: 64

Asn Tyr Thr Asn Trp Tyr Arg Gly
1               5

<210> SEQ ID NO 65
<211> LENGTH: 8
<212> TYPE: PRT
<213> ORGANISM: homo sapiens

<400> SEQUENCE: 65

Tyr Thr Asn Trp Tyr Arg Gly Glu
1               5

<210> SEQ ID NO 66
<211> LENGTH: 9
<212> TYPE: PRT
<213> ORGANISM: homo sapiens

<400> SEQUENCE: 66

Gly Asp Phe Arg Tyr Ser Asp Gly Thr
1               5

<210> SEQ ID NO 67
<211> LENGTH: 9
<212> TYPE: PRT
<213> ORGANISM: homo sapiens

<400> SEQUENCE: 67

Asp Phe Arg Tyr Ser Asp Gly Thr Pro
1               5

<210> SEQ ID NO 68
<211> LENGTH: 9
<212> TYPE: PRT
<213> ORGANISM: homo sapiens

<400> SEQUENCE: 68

Phe Arg Tyr Ser Asp Gly Thr Pro Val
1               5

```
<210> SEQ ID NO 69
<211> LENGTH: 9
<212> TYPE: PRT
<213> ORGANISM: homo sapiens

<400> SEQUENCE: 69

Arg Tyr Ser Asp Gly Thr Pro Val Asn
1               5

<210> SEQ ID NO 70
<211> LENGTH: 9
<212> TYPE: PRT
<213> ORGANISM: homo sapiens

<400> SEQUENCE: 70

Tyr Ser Asp Gly Thr Pro Val Asn Tyr
1               5

<210> SEQ ID NO 71
<211> LENGTH: 9
<212> TYPE: PRT
<213> ORGANISM: homo sapiens

<400> SEQUENCE: 71

Ser Asp Gly Thr Pro Val Asn Tyr Thr
1               5

<210> SEQ ID NO 72
<211> LENGTH: 9
<212> TYPE: PRT
<213> ORGANISM: homo sapiens

<400> SEQUENCE: 72

Asp Gly Thr Pro Val Asn Tyr Thr Asn
1               5

<210> SEQ ID NO 73
<211> LENGTH: 9
<212> TYPE: PRT
<213> ORGANISM: homo sapiens

<400> SEQUENCE: 73

Gly Thr Pro Val Asn Tyr Thr Asn Trp
1               5

<210> SEQ ID NO 74
<211> LENGTH: 9
<212> TYPE: PRT
<213> ORGANISM: Homo sapiens

<400> SEQUENCE: 74

Thr Pro Val Asn Tyr Thr Asn Trp Tyr
1               5

<210> SEQ ID NO 75
<211> LENGTH: 9
<212> TYPE: PRT
<213> ORGANISM: homo sapiens

<400> SEQUENCE: 75

Pro Val Asn Tyr Thr Asn Trp Tyr Arg
1               5

<210> SEQ ID NO 76
<211> LENGTH: 9
<212> TYPE: PRT
```

<213> ORGANISM: homo sapiens

<400> SEQUENCE: 76

Val Asn Tyr Thr Asn Trp Tyr Arg Gly
1               5

<210> SEQ ID NO 77
<211> LENGTH: 9
<212> TYPE: PRT
<213> ORGANISM: homo sapiens

<400> SEQUENCE: 77

Asn Tyr Thr Asn Trp Tyr Arg Gly Glu
1               5

<210> SEQ ID NO 78
<211> LENGTH: 10
<212> TYPE: PRT
<213> ORGANISM: homo sapiens

<400> SEQUENCE: 78

Gly Asp Phe Arg Tyr Ser Asp Gly Thr Pro
1               5                   10

<210> SEQ ID NO 79
<211> LENGTH: 10
<212> TYPE: PRT
<213> ORGANISM: homo sapiens

<400> SEQUENCE: 79

Asp Phe Arg Tyr Ser Asp Gly Thr Pro Val
1               5                   10

<210> SEQ ID NO 80
<211> LENGTH: 10
<212> TYPE: PRT
<213> ORGANISM: homo sapiens

<400> SEQUENCE: 80

Phe Arg Tyr Ser Asp Gly Thr Pro Val Asn
1               5                   10

<210> SEQ ID NO 81
<211> LENGTH: 10
<212> TYPE: PRT
<213> ORGANISM: homo sapiens

<400> SEQUENCE: 81

Arg Tyr Ser Asp Gly Thr Pro Val Asn Tyr
1               5                   10

<210> SEQ ID NO 82
<211> LENGTH: 10
<212> TYPE: PRT
<213> ORGANISM: homo sapiens

<400> SEQUENCE: 82

Tyr Ser Asp Gly Thr Pro Val Asn Tyr Thr
1               5                   10

<210> SEQ ID NO 83
<211> LENGTH: 10
<212> TYPE: PRT
<213> ORGANISM: homo sapiens

<400> SEQUENCE: 83

Ser Asp Gly Thr Pro Val Asn Tyr Thr Asn
1               5                   10

<210> SEQ ID NO 84
<211> LENGTH: 10
<212> TYPE: PRT
<213> ORGANISM: homo sapiens

<400> SEQUENCE: 84

Asp Gly Thr Pro Val Asn Tyr Thr Asn Trp
1               5                   10

<210> SEQ ID NO 85
<211> LENGTH: 10
<212> TYPE: PRT
<213> ORGANISM: homo sapiens

<400> SEQUENCE: 85

Gly Thr Pro Val Asn Tyr Thr Asn Trp Tyr
1               5                   10

<210> SEQ ID NO 86
<211> LENGTH: 10
<212> TYPE: PRT
<213> ORGANISM: homo sapiens

<400> SEQUENCE: 86

Thr Pro Val Asn Tyr Thr Asn Trp Tyr Arg
1               5                   10

<210> SEQ ID NO 87
<211> LENGTH: 10
<212> TYPE: PRT
<213> ORGANISM: homo sapiens

<400> SEQUENCE: 87

Pro Val Asn Tyr Thr Asn Trp Tyr Arg Gly
1               5                   10

<210> SEQ ID NO 88
<211> LENGTH: 10
<212> TYPE: PRT
<213> ORGANISM: homo sapiens

<400> SEQUENCE: 88

Val Asn Tyr Thr Asn Trp Tyr Arg Gly Glu
1               5                   10

<210> SEQ ID NO 89
<211> LENGTH: 11
<212> TYPE: PRT
<213> ORGANISM: homo sapiens

<400> SEQUENCE: 89

Gly Asp Phe Arg Tyr Ser Asp Gly Thr Pro Val
1               5                   10

<210> SEQ ID NO 90
<211> LENGTH: 11
<212> TYPE: PRT
<213> ORGANISM: homo sapiens

<400> SEQUENCE: 90

Asp Phe Arg Tyr Ser Asp Gly Thr Pro Val Asn
1               5                   10

<210> SEQ ID NO 91
<211> LENGTH: 11
<212> TYPE: PRT
<213> ORGANISM: homo sapiens

<400> SEQUENCE: 91

Phe Arg Tyr Ser Asp Gly Thr Pro Val Asn Tyr
1               5                   10

<210> SEQ ID NO 92
<211> LENGTH: 11
<212> TYPE: PRT
<213> ORGANISM: homo sapiens

<400> SEQUENCE: 92

Arg Tyr Ser Asp Gly Thr Pro Val Asn Tyr Thr
1               5                   10

<210> SEQ ID NO 93
<211> LENGTH: 11
<212> TYPE: PRT
<213> ORGANISM: homo sapiens

<400> SEQUENCE: 93

Tyr Ser Asp Gly Thr Pro Val Asn Tyr Thr Asn
1               5                   10

<210> SEQ ID NO 94
<211> LENGTH: 11
<212> TYPE: PRT
<213> ORGANISM: homo sapiens

<400> SEQUENCE: 94

Ser Asp Gly Thr Pro Val Asn Tyr Thr Asn Trp
1               5                   10

<210> SEQ ID NO 95
<211> LENGTH: 11
<212> TYPE: PRT
<213> ORGANISM: homo sapiens

<400> SEQUENCE: 95

Asp Gly Thr Pro Val Asn Tyr Thr Asn Trp Tyr
1               5                   10

<210> SEQ ID NO 96
<211> LENGTH: 11
<212> TYPE: PRT
<213> ORGANISM: homo sapiens

<400> SEQUENCE: 96

Gly Thr Pro Val Asn Tyr Thr Asn Trp Tyr Arg
1               5                   10

<210> SEQ ID NO 97
<211> LENGTH: 11
<212> TYPE: PRT
<213> ORGANISM: homo sapiens

<400> SEQUENCE: 97

Thr Pro Val Asn Tyr Thr Asn Trp Tyr Arg Gly
1               5                   10

<210> SEQ ID NO 98

```
<211> LENGTH: 11
<212> TYPE: PRT
<213> ORGANISM: homo sapiens

<400> SEQUENCE: 98

Pro Val Asn Tyr Thr Asn Trp Tyr Arg Gly Glu
1               5                   10

<210> SEQ ID NO 99
<211> LENGTH: 12
<212> TYPE: PRT
<213> ORGANISM: homo sapiens

<400> SEQUENCE: 99

Gly Asp Phe Arg Tyr Ser Asp Gly Thr Pro Val Asn
1               5                   10

<210> SEQ ID NO 100
<211> LENGTH: 12
<212> TYPE: PRT
<213> ORGANISM: homo sapiens

<400> SEQUENCE: 100

Asp Phe Arg Tyr Ser Asp Gly Thr Pro Val Asn Tyr
1               5                   10

<210> SEQ ID NO 101
<211> LENGTH: 12
<212> TYPE: PRT
<213> ORGANISM: homo sapiens

<400> SEQUENCE: 101

Phe Arg Tyr Ser Asp Gly Thr Pro Val Asn Tyr Thr
1               5                   10

<210> SEQ ID NO 102
<211> LENGTH: 12
<212> TYPE: PRT
<213> ORGANISM: homo sapiens

<400> SEQUENCE: 102

Arg Tyr Ser Asp Gly Thr Pro Val Asn Tyr Thr Asn
1               5                   10

<210> SEQ ID NO 103
<211> LENGTH: 12
<212> TYPE: PRT
<213> ORGANISM: homo sapiens

<400> SEQUENCE: 103

Tyr Ser Asp Gly Thr Pro Val Asn Tyr Thr Asn Trp
1               5                   10

<210> SEQ ID NO 104
<211> LENGTH: 12
<212> TYPE: PRT
<213> ORGANISM: homo sapiens

<400> SEQUENCE: 104

Ser Asp Gly Thr Pro Val Asn Tyr Thr Asn Trp Tyr
1               5                   10

<210> SEQ ID NO 105
<211> LENGTH: 12
<212> TYPE: PRT
<213> ORGANISM: homo sapiens
```

<400> SEQUENCE: 105

Asp Gly Thr Pro Val Asn Tyr Thr Asn Trp Tyr Arg
1               5                   10

<210> SEQ ID NO 106
<211> LENGTH: 12
<212> TYPE: PRT
<213> ORGANISM: homo sapiens

<400> SEQUENCE: 106

Gly Thr Pro Val Asn Tyr Thr Asn Trp Tyr Arg Gly
1               5                   10

<210> SEQ ID NO 107
<211> LENGTH: 12
<212> TYPE: PRT
<213> ORGANISM: homo sapiens

<400> SEQUENCE: 107

Thr Pro Val Asn Tyr Thr Asn Trp Tyr Arg Gly Glu
1               5                   10

<210> SEQ ID NO 108
<211> LENGTH: 13
<212> TYPE: PRT
<213> ORGANISM: homo sapiens

<400> SEQUENCE: 108

Gly Asp Phe Arg Tyr Ser Asp Gly Thr Pro Val Asn Tyr
1               5                   10

<210> SEQ ID NO 109
<211> LENGTH: 13
<212> TYPE: PRT
<213> ORGANISM: homo sapiens

<400> SEQUENCE: 109

Asp Phe Arg Tyr Ser Asp Gly Thr Pro Val Asn Tyr Thr
1               5                   10

<210> SEQ ID NO 110
<211> LENGTH: 13
<212> TYPE: PRT
<213> ORGANISM: homo sapiens

<400> SEQUENCE: 110

Phe Arg Tyr Ser Asp Gly Thr Pro Val Asn Tyr Thr Asn
1               5                   10

<210> SEQ ID NO 111
<211> LENGTH: 13
<212> TYPE: PRT
<213> ORGANISM: homo sapiens

<400> SEQUENCE: 111

Arg Tyr Ser Asp Gly Thr Pro Val Asn Tyr Thr Asn Trp
1               5                   10

<210> SEQ ID NO 112
<211> LENGTH: 13
<212> TYPE: PRT
<213> ORGANISM: homo sapiens

<400> SEQUENCE: 112

```
Tyr Ser Asp Gly Thr Pro Val Asn Tyr Thr Asn Trp Tyr
1               5                   10
```

<210> SEQ ID NO 113
<211> LENGTH: 13
<212> TYPE: PRT
<213> ORGANISM: homo sapiens

<400> SEQUENCE: 113

```
Ser Asp Gly Thr Pro Val Asn Tyr Thr Asn Trp Tyr Arg
1               5                   10
```

<210> SEQ ID NO 114
<211> LENGTH: 13
<212> TYPE: PRT
<213> ORGANISM: homo sapiens

<400> SEQUENCE: 114

```
Asp Gly Thr Pro Val Asn Tyr Thr Asn Trp Tyr Arg Gly
1               5                   10
```

<210> SEQ ID NO 115
<211> LENGTH: 13
<212> TYPE: PRT
<213> ORGANISM: homo sapiens

<400> SEQUENCE: 115

```
Gly Thr Pro Val Asn Tyr Thr Asn Trp Tyr Arg Gly Glu
1               5                   10
```

<210> SEQ ID NO 116
<211> LENGTH: 14
<212> TYPE: PRT
<213> ORGANISM: homo sapiens

<400> SEQUENCE: 116

```
Gly Asp Phe Arg Tyr Ser Asp Gly Thr Pro Val Asn Tyr Thr
1               5                   10
```

<210> SEQ ID NO 117
<211> LENGTH: 14
<212> TYPE: PRT
<213> ORGANISM: homo sapiens

<400> SEQUENCE: 117

```
Asp Phe Arg Tyr Ser Asp Gly Thr Pro Val Asn Tyr Thr Asn
1               5                   10
```

<210> SEQ ID NO 118
<211> LENGTH: 14
<212> TYPE: PRT
<213> ORGANISM: homo sapiens

<400> SEQUENCE: 118

```
Phe Arg Tyr Ser Asp Gly Thr Pro Val Asn Tyr Thr Asn Trp
1               5                   10
```

<210> SEQ ID NO 119
<211> LENGTH: 14
<212> TYPE: PRT
<213> ORGANISM: homo sapiens

<400> SEQUENCE: 119

```
Arg Tyr Ser Asp Gly Thr Pro Val Asn Tyr Thr Asn Trp Tyr
1               5                   10
```

<210> SEQ ID NO 120
<211> LENGTH: 14
<212> TYPE: PRT
<213> ORGANISM: homo sapiens

<400> SEQUENCE: 120

Tyr Ser Asp Gly Thr Pro Val Asn Tyr Thr Asn Trp Tyr Arg
1               5                   10

<210> SEQ ID NO 121
<211> LENGTH: 14
<212> TYPE: PRT
<213> ORGANISM: homo sapiens

<400> SEQUENCE: 121

Ser Asp Gly Thr Pro Val Asn Tyr Thr Asn Trp Tyr Arg Gly
1               5                   10

<210> SEQ ID NO 122
<211> LENGTH: 14
<212> TYPE: PRT
<213> ORGANISM: homo sapiens

<400> SEQUENCE: 122

Asp Gly Thr Pro Val Asn Tyr Thr Asn Trp Tyr Arg Gly Glu
1               5                   10

<210> SEQ ID NO 123
<211> LENGTH: 15
<212> TYPE: PRT
<213> ORGANISM: homo sapiens

<400> SEQUENCE: 123

Gly Asp Phe Arg Tyr Ser Asp Gly Thr Pro Val Asn Tyr Thr Asn
1               5                   10                  15

<210> SEQ ID NO 124
<211> LENGTH: 15
<212> TYPE: PRT
<213> ORGANISM: homo sapiens

<400> SEQUENCE: 124

Asp Phe Arg Tyr Ser Asp Gly Thr Pro Val Asn Tyr Thr Asn Trp
1               5                   10                  15

<210> SEQ ID NO 125
<211> LENGTH: 15
<212> TYPE: PRT
<213> ORGANISM: homo sapiens

<400> SEQUENCE: 125

Phe Arg Tyr Ser Asp Gly Thr Pro Val Asn Tyr Thr Asn Trp Tyr
1               5                   10                  15

<210> SEQ ID NO 126
<211> LENGTH: 15
<212> TYPE: PRT
<213> ORGANISM: homo sapiens

<400> SEQUENCE: 126

Arg Tyr Ser Asp Gly Thr Pro Val Asn Tyr Thr Asn Trp Tyr Arg
1               5                   10                  15

<210> SEQ ID NO 127
<211> LENGTH: 15

```
<212> TYPE: PRT
<213> ORGANISM: homo sapiens

<400> SEQUENCE: 127

Tyr Ser Asp Gly Thr Pro Val Asn Tyr Thr Asn Trp Tyr Arg Gly
1               5                   10                  15

<210> SEQ ID NO 128
<211> LENGTH: 15
<212> TYPE: PRT
<213> ORGANISM: homo sapiens

<400> SEQUENCE: 128

Ser Asp Gly Thr Pro Val Asn Tyr Thr Asn Trp Tyr Arg Gly Glu
1               5                   10                  15

<210> SEQ ID NO 129
<211> LENGTH: 16
<212> TYPE: PRT
<213> ORGANISM: homo sapiens

<400> SEQUENCE: 129

Gly Asp Phe Arg Tyr Ser Asp Gly Thr Pro Val Asn Tyr Thr Asn Trp
1               5                   10                  15

<210> SEQ ID NO 130
<211> LENGTH: 16
<212> TYPE: PRT
<213> ORGANISM: homo sapiens

<400> SEQUENCE: 130

Asp Phe Arg Tyr Ser Asp Gly Thr Pro Val Asn Tyr Thr Asn Trp Tyr
1               5                   10                  15

<210> SEQ ID NO 131
<211> LENGTH: 16
<212> TYPE: PRT
<213> ORGANISM: homo sapiens

<400> SEQUENCE: 131

Phe Arg Tyr Ser Asp Gly Thr Pro Val Asn Tyr Thr Asn Trp Tyr Arg
1               5                   10                  15

<210> SEQ ID NO 132
<211> LENGTH: 16
<212> TYPE: PRT
<213> ORGANISM: homo sapiens

<400> SEQUENCE: 132

Arg Tyr Ser Asp Gly Thr Pro Val Asn Tyr Thr Asn Trp Tyr Arg Gly
1               5                   10                  15

<210> SEQ ID NO 133
<211> LENGTH: 16
<212> TYPE: PRT
<213> ORGANISM: homo sapiens

<400> SEQUENCE: 133

Tyr Ser Asp Gly Thr Pro Val Asn Tyr Thr Asn Trp Tyr Arg Gly Glu
1               5                   10                  15

<210> SEQ ID NO 134
<211> LENGTH: 17
<212> TYPE: PRT
<213> ORGANISM: homo sapiens
```

<400> SEQUENCE: 134

Gly Asp Phe Arg Tyr Ser Asp Gly Thr Pro Val Asn Tyr Thr Asn Trp
1               5                   10                  15

Tyr

<210> SEQ ID NO 135
<211> LENGTH: 17
<212> TYPE: PRT
<213> ORGANISM: homo sapiens

<400> SEQUENCE: 135

Asp Phe Arg Tyr Ser Asp Gly Thr Pro Val Asn Tyr Thr Asn Trp Tyr
1               5                   10                  15

Arg

<210> SEQ ID NO 136
<211> LENGTH: 17
<212> TYPE: PRT
<213> ORGANISM: homo sapiens

<400> SEQUENCE: 136

Phe Arg Tyr Ser Asp Gly Thr Pro Val Asn Tyr Thr Asn Trp Tyr Arg
1               5                   10                  15

Gly

<210> SEQ ID NO 137
<211> LENGTH: 17
<212> TYPE: PRT
<213> ORGANISM: homo sapiens

<400> SEQUENCE: 137

Arg Tyr Ser Asp Gly Thr Pro Val Asn Tyr Thr Asn Trp Tyr Arg Gly
1               5                   10                  15

Glu

<210> SEQ ID NO 138
<211> LENGTH: 18
<212> TYPE: PRT
<213> ORGANISM: homo sapiens

<400> SEQUENCE: 138

Gly Asp Phe Arg Tyr Ser Asp Gly Thr Pro Val Asn Tyr Thr Asn Trp
1               5                   10                  15

Tyr Arg

<210> SEQ ID NO 139
<211> LENGTH: 18
<212> TYPE: PRT
<213> ORGANISM: homo sapiens

<400> SEQUENCE: 139

Asp Phe Arg Tyr Ser Asp Gly Thr Pro Val Asn Tyr Thr Asn Trp Tyr
1               5                   10                  15

Arg Gly

<210> SEQ ID NO 140
<211> LENGTH: 18
<212> TYPE: PRT
<213> ORGANISM: homo sapiens

<400> SEQUENCE: 140

```
Phe Arg Tyr Ser Asp Gly Thr Pro Val Asn Tyr Thr Asn Trp Tyr Arg
1               5                   10                  15

Gly Glu

<210> SEQ ID NO 141
<211> LENGTH: 19
<212> TYPE: PRT
<213> ORGANISM: homo sapiens

<400> SEQUENCE: 141

Gly Asp Phe Arg Tyr Ser Asp Gly Thr Pro Val Asn Tyr Thr Asn Trp
1               5                   10                  15

Tyr Arg Gly

<210> SEQ ID NO 142
<211> LENGTH: 19
<212> TYPE: PRT
<213> ORGANISM: homo sapiens

<400> SEQUENCE: 142

Asp Phe Arg Tyr Ser Asp Gly Thr Pro Val Asn Tyr Thr Asn Trp Tyr
1               5                   10                  15

Arg Gly Glu

<210> SEQ ID NO 143
<211> LENGTH: 5
<212> TYPE: PRT
<213> ORGANISM: homo sapiens

<400> SEQUENCE: 143

Tyr Val Gly Leu Thr
1               5

<210> SEQ ID NO 144
<211> LENGTH: 5
<212> TYPE: PRT
<213> ORGANISM: homo sapiens

<400> SEQUENCE: 144

Val Gly Leu Thr Glu
1               5

<210> SEQ ID NO 145
<211> LENGTH: 5
<212> TYPE: PRT
<213> ORGANISM: homo sapiens

<400> SEQUENCE: 145

Gly Leu Thr Glu Gly
1               5

<210> SEQ ID NO 146
<211> LENGTH: 5
<212> TYPE: PRT
<213> ORGANISM: homo sapiens

<400> SEQUENCE: 146

Leu Thr Glu Gly Pro
1               5

<210> SEQ ID NO 147
<211> LENGTH: 5
<212> TYPE: PRT
<213> ORGANISM: homo sapiens
```

<400> SEQUENCE: 147

Thr Glu Gly Pro Ser
1               5

<210> SEQ ID NO 148
<211> LENGTH: 5
<212> TYPE: PRT
<213> ORGANISM: homo sapiens

<400> SEQUENCE: 148

Glu Gly Pro Ser Pro
1               5

<210> SEQ ID NO 149
<211> LENGTH: 5
<212> TYPE: PRT
<213> ORGANISM: homo sapiens

<400> SEQUENCE: 149

Gly Pro Ser Pro Gly
1               5

<210> SEQ ID NO 150
<211> LENGTH: 5
<212> TYPE: PRT
<213> ORGANISM: homo sapiens

<400> SEQUENCE: 150

Pro Ser Pro Gly Asp
1               5

<210> SEQ ID NO 151
<211> LENGTH: 5
<212> TYPE: PRT
<213> ORGANISM: homo sapiens

<400> SEQUENCE: 151

Ser Pro Gly Asp Phe
1               5

<210> SEQ ID NO 152
<211> LENGTH: 5
<212> TYPE: PRT
<213> ORGANISM: homo sapiens

<400> SEQUENCE: 152

Pro Gly Asp Phe Arg
1               5

<210> SEQ ID NO 153
<211> LENGTH: 6
<212> TYPE: PRT
<213> ORGANISM: homo sapiens

<400> SEQUENCE: 153

Tyr Val Gly Leu Thr Glu
1               5

<210> SEQ ID NO 154
<211> LENGTH: 6
<212> TYPE: PRT
<213> ORGANISM: homo sapiens

<400> SEQUENCE: 154

Val Gly Leu Thr Glu Gly
1               5

<210> SEQ ID NO 155
<211> LENGTH: 6
<212> TYPE: PRT
<213> ORGANISM: homo sapiens

<400> SEQUENCE: 155

Gly Leu Thr Glu Gly Pro
1               5

<210> SEQ ID NO 156
<211> LENGTH: 6
<212> TYPE: PRT
<213> ORGANISM: homo sapiens

<400> SEQUENCE: 156

Leu Thr Glu Gly Pro Ser
1               5

<210> SEQ ID NO 157
<211> LENGTH: 6
<212> TYPE: PRT
<213> ORGANISM: homo sapiens

<400> SEQUENCE: 157

Thr Glu Gly Pro Ser Pro
1               5

<210> SEQ ID NO 158
<211> LENGTH: 6
<212> TYPE: PRT
<213> ORGANISM: homo sapiens

<400> SEQUENCE: 158

Glu Gly Pro Ser Pro Gly
1               5

<210> SEQ ID NO 159
<211> LENGTH: 6
<212> TYPE: PRT
<213> ORGANISM: homo sapiens

<400> SEQUENCE: 159

Gly Pro Ser Pro Gly Asp
1               5

<210> SEQ ID NO 160
<211> LENGTH: 6
<212> TYPE: PRT
<213> ORGANISM: homo sapiens

<400> SEQUENCE: 160

Pro Ser Pro Gly Asp Phe
1               5

<210> SEQ ID NO 161
<211> LENGTH: 6
<212> TYPE: PRT
<213> ORGANISM: homo sapiens

<400> SEQUENCE: 161

Ser Pro Gly Asp Phe Arg
1               5

```
<210> SEQ ID NO 162
<211> LENGTH: 6
<212> TYPE: PRT
<213> ORGANISM: homo sapiens

<400> SEQUENCE: 162

Pro Gly Asp Phe Arg Tyr
1               5

<210> SEQ ID NO 163
<211> LENGTH: 7
<212> TYPE: PRT
<213> ORGANISM: homo sapiens

<400> SEQUENCE: 163

Tyr Val Gly Leu Thr Glu Gly
1               5

<210> SEQ ID NO 164
<211> LENGTH: 7
<212> TYPE: PRT
<213> ORGANISM: homo sapiens

<400> SEQUENCE: 164

Val Gly Leu Thr Glu Gly Pro
1               5

<210> SEQ ID NO 165
<211> LENGTH: 7
<212> TYPE: PRT
<213> ORGANISM: homo sapiens

<400> SEQUENCE: 165

Gly Leu Thr Glu Gly Pro Ser
1               5

<210> SEQ ID NO 166
<211> LENGTH: 7
<212> TYPE: PRT
<213> ORGANISM: homo sapiens

<400> SEQUENCE: 166

Leu Thr Glu Gly Pro Ser Pro
1               5

<210> SEQ ID NO 167
<211> LENGTH: 7
<212> TYPE: PRT
<213> ORGANISM: homo sapiens

<400> SEQUENCE: 167

Thr Glu Gly Pro Ser Pro Gly
1               5

<210> SEQ ID NO 168
<211> LENGTH: 7
<212> TYPE: PRT
<213> ORGANISM: homo sapiens

<400> SEQUENCE: 168

Glu Gly Pro Ser Pro Gly Asp
1               5

<210> SEQ ID NO 169
<211> LENGTH: 7
```

```
<212> TYPE: PRT
<213> ORGANISM: homo sapiens

<400> SEQUENCE: 169

Gly Pro Ser Pro Gly Asp Phe
1               5

<210> SEQ ID NO 170
<211> LENGTH: 7
<212> TYPE: PRT
<213> ORGANISM: homo sapiens

<400> SEQUENCE: 170

Pro Ser Pro Gly Asp Phe Arg
1               5

<210> SEQ ID NO 171
<211> LENGTH: 7
<212> TYPE: PRT
<213> ORGANISM: homo sapiens

<400> SEQUENCE: 171

Ser Pro Gly Asp Phe Arg Tyr
1               5

<210> SEQ ID NO 172
<211> LENGTH: 7
<212> TYPE: PRT
<213> ORGANISM: homo sapiens

<400> SEQUENCE: 172

Pro Gly Asp Phe Arg Tyr Ser
1               5

<210> SEQ ID NO 173
<211> LENGTH: 8
<212> TYPE: PRT
<213> ORGANISM: homo sapiens

<400> SEQUENCE: 173

Tyr Val Gly Leu Thr Glu Gly Pro
1               5

<210> SEQ ID NO 174
<211> LENGTH: 8
<212> TYPE: PRT
<213> ORGANISM: homo sapiens

<400> SEQUENCE: 174

Val Gly Leu Thr Glu Gly Pro Ser
1               5

<210> SEQ ID NO 175
<211> LENGTH: 8
<212> TYPE: PRT
<213> ORGANISM: homo sapiens

<400> SEQUENCE: 175

Gly Leu Thr Glu Gly Pro Ser Pro
1               5

<210> SEQ ID NO 176
<211> LENGTH: 8
<212> TYPE: PRT
<213> ORGANISM: homo sapiens
```

-continued

```
<400> SEQUENCE: 176

Leu Thr Glu Gly Pro Ser Pro Gly
1               5

<210> SEQ ID NO 177
<211> LENGTH: 8
<212> TYPE: PRT
<213> ORGANISM: homo sapiens

<400> SEQUENCE: 177

Thr Glu Gly Pro Ser Pro Gly Asp
1               5

<210> SEQ ID NO 178
<211> LENGTH: 8
<212> TYPE: PRT
<213> ORGANISM: homo sapiens

<400> SEQUENCE: 178

Glu Gly Pro Ser Pro Gly Asp Phe
1               5

<210> SEQ ID NO 179
<211> LENGTH: 8
<212> TYPE: PRT
<213> ORGANISM: homo sapiens

<400> SEQUENCE: 179

Gly Pro Ser Pro Gly Asp Phe Arg
1               5

<210> SEQ ID NO 180
<211> LENGTH: 8
<212> TYPE: PRT
<213> ORGANISM: homo sapiens

<400> SEQUENCE: 180

Pro Ser Pro Gly Asp Phe Arg Tyr
1               5

<210> SEQ ID NO 181
<211> LENGTH: 7
<212> TYPE: PRT
<213> ORGANISM: homo sapiens

<400> SEQUENCE: 181

Ser Pro Gly Asp Phe Arg Tyr
1               5

<210> SEQ ID NO 182
<211> LENGTH: 8
<212> TYPE: PRT
<213> ORGANISM: homo sapiens

<400> SEQUENCE: 182

Pro Gly Asp Phe Arg Tyr Ser Asp
1               5

<210> SEQ ID NO 183
<211> LENGTH: 9
<212> TYPE: PRT
<213> ORGANISM: homo sapiens

<400> SEQUENCE: 183

Tyr Val Gly Leu Thr Glu Gly Pro Ser
```

```
1               5

<210> SEQ ID NO 184
<211> LENGTH: 9
<212> TYPE: PRT
<213> ORGANISM: homo sapiens

<400> SEQUENCE: 184

Val Gly Leu Thr Glu Gly Pro Ser Pro
1               5

<210> SEQ ID NO 185
<211> LENGTH: 9
<212> TYPE: PRT
<213> ORGANISM: homo sapiens

<400> SEQUENCE: 185

Gly Leu Thr Glu Gly Pro Ser Pro Gly
1               5

<210> SEQ ID NO 186
<211> LENGTH: 9
<212> TYPE: PRT
<213> ORGANISM: homo sapiens

<400> SEQUENCE: 186

Leu Thr Glu Gly Pro Ser Pro Gly Asp
1               5

<210> SEQ ID NO 187
<211> LENGTH: 9
<212> TYPE: PRT
<213> ORGANISM: homo sapiens

<400> SEQUENCE: 187

Thr Glu Gly Pro Ser Pro Gly Asp Phe
1               5

<210> SEQ ID NO 188
<211> LENGTH: 9
<212> TYPE: PRT
<213> ORGANISM: homo sapiens

<400> SEQUENCE: 188

Glu Gly Pro Ser Pro Gly Asp Phe Arg
1               5

<210> SEQ ID NO 189
<211> LENGTH: 9
<212> TYPE: PRT
<213> ORGANISM: homo sapiens

<400> SEQUENCE: 189

Gly Pro Ser Pro Gly Asp Phe Arg Tyr
1               5

<210> SEQ ID NO 190
<211> LENGTH: 9
<212> TYPE: PRT
<213> ORGANISM: homo sapiens

<400> SEQUENCE: 190

Pro Ser Pro Gly Asp Phe Arg Tyr Ser
1               5
```

```
<210> SEQ ID NO 191
<211> LENGTH: 9
<212> TYPE: PRT
<213> ORGANISM: homo sapiens

<400> SEQUENCE: 191

Ser Pro Gly Asp Phe Arg Tyr Ser Asp
1               5

<210> SEQ ID NO 192
<211> LENGTH: 9
<212> TYPE: PRT
<213> ORGANISM: homo sapiens

<400> SEQUENCE: 192

Pro Gly Asp Phe Arg Tyr Ser Asp Gly
1               5

<210> SEQ ID NO 193
<211> LENGTH: 11
<212> TYPE: PRT
<213> ORGANISM: homo sapiens

<400> SEQUENCE: 193

Tyr Val Gly Leu Thr Glu Gly Pro Ser Pro Gly
1               5                   10

<210> SEQ ID NO 194
<211> LENGTH: 11
<212> TYPE: PRT
<213> ORGANISM: homo sapiens

<400> SEQUENCE: 194

Val Gly Leu Thr Glu Gly Pro Ser Pro Gly Asp
1               5                   10

<210> SEQ ID NO 195
<211> LENGTH: 11
<212> TYPE: PRT
<213> ORGANISM: homo sapiens

<400> SEQUENCE: 195

Gly Leu Thr Glu Gly Pro Ser Pro Gly Asp Phe
1               5                   10

<210> SEQ ID NO 196
<211> LENGTH: 11
<212> TYPE: PRT
<213> ORGANISM: homo sapiens

<400> SEQUENCE: 196

Leu Thr Glu Gly Pro Ser Pro Gly Asp Phe Arg
1               5                   10

<210> SEQ ID NO 197
<211> LENGTH: 11
<212> TYPE: PRT
<213> ORGANISM: homo sapiens

<400> SEQUENCE: 197

Thr Glu Gly Pro Ser Pro Gly Asp Phe Arg Tyr
1               5                   10

<210> SEQ ID NO 198
<211> LENGTH: 11
<212> TYPE: PRT
```

<213> ORGANISM: homo sapiens

<400> SEQUENCE: 198

Glu Gly Pro Ser Pro Gly Asp Phe Arg Tyr Ser
1               5                   10

<210> SEQ ID NO 199
<211> LENGTH: 11
<212> TYPE: PRT
<213> ORGANISM: homo sapiens

<400> SEQUENCE: 199

Gly Pro Ser Pro Gly Asp Phe Arg Tyr Ser Asp
1               5                   10

<210> SEQ ID NO 200
<211> LENGTH: 11
<212> TYPE: PRT
<213> ORGANISM: homo sapiens

<400> SEQUENCE: 200

Pro Ser Pro Gly Asp Phe Arg Tyr Ser Asp Gly
1               5                   10

<210> SEQ ID NO 201
<211> LENGTH: 11
<212> TYPE: PRT
<213> ORGANISM: homo sapiens

<400> SEQUENCE: 201

Ser Pro Gly Asp Phe Arg Tyr Ser Asp Gly Thr
1               5                   10

<210> SEQ ID NO 202
<211> LENGTH: 11
<212> TYPE: PRT
<213> ORGANISM: homo sapiens

<400> SEQUENCE: 202

Pro Gly Asp Phe Arg Tyr Ser Asp Gly Thr Pro
1               5                   10

<210> SEQ ID NO 203
<211> LENGTH: 12
<212> TYPE: PRT
<213> ORGANISM: homo sapiens

<400> SEQUENCE: 203

Tyr Val Gly Leu Thr Glu Gly Pro Ser Pro Gly Asp
1               5                   10

<210> SEQ ID NO 204
<211> LENGTH: 12
<212> TYPE: PRT
<213> ORGANISM: homo sapiens

<400> SEQUENCE: 204

Val Gly Leu Thr Glu Gly Pro Ser Pro Gly Asp Phe
1               5                   10

<210> SEQ ID NO 205
<211> LENGTH: 12
<212> TYPE: PRT
<213> ORGANISM: homo sapiens

<400> SEQUENCE: 205

Gly Leu Thr Glu Gly Pro Ser Pro Gly Asp Phe Arg
1               5                   10

<210> SEQ ID NO 206
<211> LENGTH: 12
<212> TYPE: PRT
<213> ORGANISM: homo sapiens

<400> SEQUENCE: 206

Leu Thr Glu Gly Pro Ser Pro Gly Asp Phe Arg Tyr
1               5                   10

<210> SEQ ID NO 207
<211> LENGTH: 12
<212> TYPE: PRT
<213> ORGANISM: homo sapiens

<400> SEQUENCE: 207

Thr Glu Gly Pro Ser Pro Gly Asp Phe Arg Tyr Ser
1               5                   10

<210> SEQ ID NO 208
<211> LENGTH: 12
<212> TYPE: PRT
<213> ORGANISM: homo sapiens

<400> SEQUENCE: 208

Glu Gly Pro Ser Pro Gly Asp Phe Arg Tyr Ser Asp
1               5                   10

<210> SEQ ID NO 209
<211> LENGTH: 12
<212> TYPE: PRT
<213> ORGANISM: homo sapiens

<400> SEQUENCE: 209

Gly Pro Ser Pro Gly Asp Phe Arg Tyr Ser Asp Gly
1               5                   10

<210> SEQ ID NO 210
<211> LENGTH: 12
<212> TYPE: PRT
<213> ORGANISM: homo sapiens

<400> SEQUENCE: 210

Pro Ser Pro Gly Asp Phe Arg Tyr Ser Asp Gly Thr
1               5                   10

<210> SEQ ID NO 211
<211> LENGTH: 12
<212> TYPE: PRT
<213> ORGANISM: homo sapiens

<400> SEQUENCE: 211

Ser Pro Gly Asp Phe Arg Tyr Ser Asp Gly Thr Pro
1               5                   10

<210> SEQ ID NO 212
<211> LENGTH: 13
<212> TYPE: PRT
<213> ORGANISM: homo sapiens

<400> SEQUENCE: 212

Tyr Val Gly Leu Thr Glu Gly Pro Ser Pro Gly Asp Phe
1               5                   10

<210> SEQ ID NO 213
<211> LENGTH: 13
<212> TYPE: PRT
<213> ORGANISM: homo sapiens

<400> SEQUENCE: 213

Val Gly Leu Thr Glu Gly Pro Ser Pro Gly Asp Phe Arg
1               5                   10

<210> SEQ ID NO 214
<211> LENGTH: 13
<212> TYPE: PRT
<213> ORGANISM: homo sapiens

<400> SEQUENCE: 214

Gly Leu Thr Glu Gly Pro Ser Pro Gly Asp Phe Arg Tyr
1               5                   10

<210> SEQ ID NO 215
<211> LENGTH: 13
<212> TYPE: PRT
<213> ORGANISM: homo sapiens

<400> SEQUENCE: 215

Leu Thr Glu Gly Pro Ser Pro Gly Asp Phe Arg Tyr Ser
1               5                   10

<210> SEQ ID NO 216
<211> LENGTH: 13
<212> TYPE: PRT
<213> ORGANISM: homo sapiens

<400> SEQUENCE: 216

Thr Glu Gly Pro Ser Pro Gly Asp Phe Arg Tyr Ser Asp
1               5                   10

<210> SEQ ID NO 217
<211> LENGTH: 13
<212> TYPE: PRT
<213> ORGANISM: homo sapiens

<400> SEQUENCE: 217

Glu Gly Pro Ser Pro Gly Asp Phe Arg Tyr Ser Asp Gly
1               5                   10

<210> SEQ ID NO 218
<211> LENGTH: 13
<212> TYPE: PRT
<213> ORGANISM: homo sapiens

<400> SEQUENCE: 218

Gly Pro Ser Pro Gly Asp Phe Arg Tyr Ser Asp Gly Thr
1               5                   10

<210> SEQ ID NO 219
<211> LENGTH: 13
<212> TYPE: PRT
<213> ORGANISM: homo sapiens

<400> SEQUENCE: 219

Pro Ser Pro Gly Asp Phe Arg Tyr Ser Asp Gly Thr Pro
1               5                   10

<210> SEQ ID NO 220

```
<211> LENGTH: 14
<212> TYPE: PRT
<213> ORGANISM: homo sapiens

<400> SEQUENCE: 220

Tyr Val Gly Leu Thr Glu Gly Pro Ser Pro Gly Asp Phe Arg
1               5                   10

<210> SEQ ID NO 221
<211> LENGTH: 14
<212> TYPE: PRT
<213> ORGANISM: homo sapiens

<400> SEQUENCE: 221

Val Gly Leu Thr Glu Gly Pro Ser Pro Gly Asp Phe Arg Tyr
1               5                   10

<210> SEQ ID NO 222
<211> LENGTH: 14
<212> TYPE: PRT
<213> ORGANISM: homo sapiens

<400> SEQUENCE: 222

Gly Leu Thr Glu Gly Pro Ser Pro Gly Asp Phe Arg Tyr Ser
1               5                   10

<210> SEQ ID NO 223
<211> LENGTH: 14
<212> TYPE: PRT
<213> ORGANISM: homo sapiens

<400> SEQUENCE: 223

Leu Thr Glu Gly Pro Ser Pro Gly Asp Phe Arg Tyr Ser Asp
1               5                   10

<210> SEQ ID NO 224
<211> LENGTH: 14
<212> TYPE: PRT
<213> ORGANISM: homo sapiens

<400> SEQUENCE: 224

Thr Glu Gly Pro Ser Pro Gly Asp Phe Arg Tyr Ser Asp Gly
1               5                   10

<210> SEQ ID NO 225
<211> LENGTH: 14
<212> TYPE: PRT
<213> ORGANISM: homo sapiens

<400> SEQUENCE: 225

Glu Gly Pro Ser Pro Gly Asp Phe Arg Tyr Ser Asp Gly Thr
1               5                   10

<210> SEQ ID NO 226
<211> LENGTH: 14
<212> TYPE: PRT
<213> ORGANISM: homo sapiens

<400> SEQUENCE: 226

Gly Pro Ser Pro Gly Asp Phe Arg Tyr Ser Asp Gly Thr Pro
1               5                   10

<210> SEQ ID NO 227
<211> LENGTH: 15
<212> TYPE: PRT
<213> ORGANISM: homo sapiens
```

<400> SEQUENCE: 227

Tyr Val Gly Leu Thr Glu Gly Pro Ser Pro Gly Asp Phe Arg Tyr
1               5                   10                  15

<210> SEQ ID NO 228
<211> LENGTH: 15
<212> TYPE: PRT
<213> ORGANISM: homo sapiens

<400> SEQUENCE: 228

Val Gly Leu Thr Glu Gly Pro Ser Pro Gly Asp Phe Arg Tyr Ser
1               5                   10                  15

<210> SEQ ID NO 229
<211> LENGTH: 15
<212> TYPE: PRT
<213> ORGANISM: homo sapiens

<400> SEQUENCE: 229

Gly Leu Thr Glu Gly Pro Ser Pro Gly Asp Phe Arg Tyr Ser Asp
1               5                   10                  15

<210> SEQ ID NO 230
<211> LENGTH: 15
<212> TYPE: PRT
<213> ORGANISM: homo sapiens

<400> SEQUENCE: 230

Leu Thr Glu Gly Pro Ser Pro Gly Asp Phe Arg Tyr Ser Asp Gly
1               5                   10                  15

<210> SEQ ID NO 231
<211> LENGTH: 15
<212> TYPE: PRT
<213> ORGANISM: homo sapiens

<400> SEQUENCE: 231

Thr Glu Gly Pro Ser Pro Gly Asp Phe Arg Tyr Ser Asp Gly Thr
1               5                   10                  15

<210> SEQ ID NO 232
<211> LENGTH: 15
<212> TYPE: PRT
<213> ORGANISM: homo sapiens

<400> SEQUENCE: 232

Glu Gly Pro Ser Pro Gly Asp Phe Arg Tyr Ser Asp Gly Thr Pro
1               5                   10                  15

<210> SEQ ID NO 233
<211> LENGTH: 16
<212> TYPE: PRT
<213> ORGANISM: homo sapiens

<400> SEQUENCE: 233

Tyr Val Gly Leu Thr Glu Gly Pro Ser Pro Gly Asp Phe Arg Tyr Ser
1               5                   10                  15

<210> SEQ ID NO 234
<211> LENGTH: 16
<212> TYPE: PRT
<213> ORGANISM: homo sapiens

<400> SEQUENCE: 234

Val Gly Leu Thr Glu Gly Pro Ser Pro Gly Asp Phe Arg Tyr Ser Asp
1               5                   10                  15

<210> SEQ ID NO 235
<211> LENGTH: 16
<212> TYPE: PRT
<213> ORGANISM: homo sapiens

<400> SEQUENCE: 235

Gly Leu Thr Glu Gly Pro Ser Pro Gly Asp Phe Arg Tyr Ser Asp Gly
1               5                   10                  15

<210> SEQ ID NO 236
<211> LENGTH: 16
<212> TYPE: PRT
<213> ORGANISM: homo sapiens

<400> SEQUENCE: 236

Leu Thr Glu Gly Pro Ser Pro Gly Asp Phe Arg Tyr Ser Asp Gly Thr
1               5                   10                  15

<210> SEQ ID NO 237
<211> LENGTH: 16
<212> TYPE: PRT
<213> ORGANISM: homo sapiens

<400> SEQUENCE: 237

Thr Glu Gly Pro Ser Pro Gly Asp Phe Arg Tyr Ser Asp Gly Thr Pro
1               5                   10                  15

<210> SEQ ID NO 238
<211> LENGTH: 17
<212> TYPE: PRT
<213> ORGANISM: homo sapiens

<400> SEQUENCE: 238

Tyr Val Gly Leu Thr Glu Gly Pro Ser Pro Gly Asp Phe Arg Tyr Ser
1               5                   10                  15

Asp

<210> SEQ ID NO 239
<211> LENGTH: 17
<212> TYPE: PRT
<213> ORGANISM: homo sapiens

<400> SEQUENCE: 239

Val Gly Leu Thr Glu Gly Pro Ser Pro Gly Asp Phe Arg Tyr Ser Asp
1               5                   10                  15

Gly

<210> SEQ ID NO 240
<211> LENGTH: 17
<212> TYPE: PRT
<213> ORGANISM: homo sapiens

<400> SEQUENCE: 240

Gly Leu Thr Glu Gly Pro Ser Pro Gly Asp Phe Arg Tyr Ser Asp Gly
1               5                   10                  15

Thr

<210> SEQ ID NO 241
<211> LENGTH: 17
<212> TYPE: PRT

<400> SEQUENCE: 241

Leu Thr Glu Gly Pro Ser Pro Gly Asp Phe Arg Tyr Ser Asp Gly Thr
1               5                   10                  15
Pro

<210> SEQ ID NO 242
<211> LENGTH: 18
<212> TYPE: PRT
<213> ORGANISM: homo sapiens

<400> SEQUENCE: 242

Tyr Val Gly Leu Thr Glu Gly Pro Ser Pro Gly Asp Phe Arg Tyr Ser
1               5                   10                  15
Asp Gly

<210> SEQ ID NO 243
<211> LENGTH: 18
<212> TYPE: PRT
<213> ORGANISM: homo sapiens

<400> SEQUENCE: 243

Val Gly Leu Thr Glu Gly Pro Ser Pro Gly Asp Phe Arg Tyr Ser Asp
1               5                   10                  15
Gly Thr

<210> SEQ ID NO 244
<211> LENGTH: 18
<212> TYPE: PRT
<213> ORGANISM: homo sapiens

<400> SEQUENCE: 244

Gly Leu Thr Glu Gly Pro Ser Pro Gly Asp Phe Arg Tyr Ser Asp Gly
1               5                   10                  15
Thr Pro

<210> SEQ ID NO 245
<211> LENGTH: 19
<212> TYPE: PRT
<213> ORGANISM: homo sapiens

<400> SEQUENCE: 245

Tyr Val Gly Leu Thr Glu Gly Pro Ser Pro Gly Asp Phe Arg Tyr Ser
1               5                   10                  15
Asp Gly Thr

<210> SEQ ID NO 246
<211> LENGTH: 19
<212> TYPE: PRT
<213> ORGANISM: homo sapiens

<400> SEQUENCE: 246

Val Gly Leu Thr Glu Gly Pro Ser Pro Gly Asp Phe Arg Tyr Ser Asp
1               5                   10                  15
Gly Thr Pro

<210> SEQ ID NO 247
<211> LENGTH: 835
<212> TYPE: PRT
<213> ORGANISM: Mus musculus

<400> SEQUENCE: 247

```
Met Met Pro Pro Trp Leu Leu Ala Arg Thr Leu Ile Met Ala Leu Phe
1               5                   10                  15

Phe Ser Cys Leu Thr Pro Gly Ser Leu Asn Pro Cys Ile Glu Val Val
            20                  25                  30

Pro Asn Ile Thr Tyr Gln Cys Met Asp Gln Lys Leu Ser Lys Val Pro
            35                  40                  45

Asp Asp Ile Pro Ser Ser Thr Lys Asn Ile Asp Leu Ser Phe Asn Pro
50                      55                  60

Leu Lys Ile Leu Lys Ser Tyr Ser Phe Ser Asn Phe Ser Glu Leu Gln
65                  70                  75                  80

Trp Leu Asp Leu Ser Arg Cys Glu Ile Glu Thr Ile Glu Asp Lys Ala
                85                  90                  95

Trp His Gly Leu His His Leu Ser Asn Leu Ile Leu Thr Gly Asn Pro
            100                 105                 110

Ile Gln Ser Phe Ser Pro Gly Ser Phe Ser Gly Leu Thr Ser Leu Glu
            115                 120                 125

Asn Leu Val Ala Val Glu Thr Lys Leu Ala Ser Leu Glu Ser Phe Pro
            130                 135                 140

Ile Gly Gln Leu Ile Thr Leu Lys Lys Leu Asn Val Ala His Asn Phe
145                 150                 155                 160

Ile His Ser Cys Lys Leu Pro Ala Tyr Phe Ser Asn Leu Thr Asn Leu
                165                 170                 175

Val His Val Asp Leu Ser Tyr Asn Tyr Ile Gln Thr Ile Thr Val Asn
            180                 185                 190

Asp Leu Gln Phe Leu Arg Glu Asn Pro Gln Val Asn Leu Ser Leu Asp
            195                 200                 205

Met Ser Leu Asn Pro Ile Asp Phe Ile Gln Asp Gln Ala Phe Gln Gly
210                 215                 220

Ile Lys Leu His Glu Leu Thr Leu Arg Gly Asn Phe Asn Ser Ser Asn
225                 230                 235                 240

Ile Met Lys Thr Cys Leu Gln Asn Leu Ala Gly Leu His Val His Arg
            245                 250                 255

Leu Ile Leu Gly Glu Phe Lys Asp Glu Arg Asn Leu Glu Ile Phe Glu
            260                 265                 270

Pro Ser Ile Met Glu Gly Leu Cys Asp Val Thr Ile Asp Glu Phe Arg
            275                 280                 285

Leu Thr Tyr Thr Asn Asp Phe Ser Asp Ile Val Lys Phe His Cys
            290                 295                 300

Leu Ala Asn Val Ser Ala Met Ser Leu Ala Gly Val Ser Ile Lys Tyr
305                 310                 315                 320

Leu Glu Asp Val Pro Lys His Phe Lys Trp Gln Ser Leu Ser Ile Ile
            325                 330                 335

Arg Cys Gln Leu Lys Gln Phe Pro Thr Leu Asp Leu Pro Phe Leu Lys
            340                 345                 350

Ser Leu Thr Leu Thr Met Asn Lys Gly Ser Ile Ser Phe Lys Lys Val
            355                 360                 365

Ala Leu Pro Ser Leu Ser Tyr Leu Asp Leu Ser Arg Asn Ala Leu Ser
            370                 375                 380

Phe Ser Gly Cys Cys Ser Tyr Ser Asp Leu Gly Thr Asn Ser Leu Arg
385                 390                 395                 400

His Leu Asp Leu Ser Phe Asn Gly Ala Ile Ile Met Ser Ala Asn Phe
                405                 410                 415

Met Gly Leu Glu Glu Leu Gln His Leu Asp Phe Gln His Ser Thr Leu
```

-continued

```
                420             425             430
Lys Arg Val Thr Glu Phe Ser Ala Phe Leu Ser Leu Glu Lys Leu Leu
            435                 440                 445
Tyr Leu Asp Ile Ser Tyr Thr Asn Thr Lys Ile Asp Phe Asp Gly Ile
        450                 455                 460
Phe Leu Gly Leu Thr Ser Leu Asn Thr Leu Lys Met Ala Gly Asn Ser
465                 470                 475                 480
Phe Lys Asp Asn Thr Leu Ser Asn Val Phe Ala Asn Thr Thr Asn Leu
                485                 490                 495
Thr Phe Leu Asp Leu Ser Lys Cys Gln Leu Glu Gln Ile Ser Trp Gly
            500                 505                 510
Val Phe Asp Thr Leu His Arg Leu Gln Leu Leu Asn Met Ser His Asn
        515                 520                 525
Asn Leu Leu Phe Leu Asp Ser Ser His Tyr Asn Gln Leu Tyr Ser Leu
    530                 535                 540
Ser Thr Leu Asp Cys Ser Phe Asn Arg Ile Glu Thr Ser Lys Gly Ile
545                 550                 555                 560
Leu Gln His Phe Pro Lys Ser Leu Ala Phe Phe Asn Leu Thr Asn Asn
                565                 570                 575
Ser Val Ala Cys Ile Cys Glu His Gln Lys Phe Leu Gln Trp Val Lys
            580                 585                 590
Glu Gln Lys Gln Phe Leu Val Asn Val Glu Gln Met Thr Cys Ala Thr
        595                 600                 605
Pro Val Glu Met Asn Thr Ser Leu Val Leu Asp Phe Asn Asn Ser Thr
    610                 615                 620
Cys Tyr Met Tyr Lys Thr Ile Ile Ser Val Ser Val Ser Val Ile
625                 630                 635                 640
Val Val Ser Thr Val Ala Phe Leu Ile Tyr His Phe Tyr Phe His Leu
                645                 650                 655
Ile Leu Ile Ala Gly Cys Lys Lys Tyr Ser Arg Gly Glu Ser Ile Tyr
            660                 665                 670
Asp Ala Phe Val Ile Tyr Ser Ser Gln Asn Glu Asp Trp Val Arg Asn
        675                 680                 685
Glu Leu Val Lys Asn Leu Glu Glu Gly Val Pro Arg Phe His Leu Cys
    690                 695                 700
Leu His Tyr Arg Asp Phe Ile Pro Gly Val Ala Ile Ala Ala Asn Ile
705                 710                 715                 720
Ile Gln Glu Gly Phe His Lys Ser Arg Lys Val Ile Val Val Val Ser
                725                 730                 735
Arg His Phe Ile Gln Ser Arg Trp Cys Ile Phe Glu Tyr Glu Ile Ala
            740                 745                 750
Gln Thr Trp Gln Phe Leu Ser Ser Arg Ser Gly Ile Ile Phe Ile Val
        755                 760                 765
Leu Glu Lys Val Glu Lys Ser Leu Leu Arg Gln Val Glu Leu Tyr
    770                 775                 780
Arg Leu Leu Ser Arg Asn Thr Tyr Leu Glu Trp Glu Asp Asn Pro Leu
785                 790                 795                 800
Gly Arg His Ile Phe Trp Arg Arg Leu Lys Asn Ala Leu Leu Asp Gly
                805                 810                 815
Lys Ala Ser Asn Pro Glu Gln Thr Ala Glu Glu Glu Glu Thr Ala
            820                 825                 830
Thr Trp Thr
        835
```

<210> SEQ ID NO 248
<211> LENGTH: 835
<212> TYPE: PRT
<213> ORGANISM: Rattus norvegicus

<400> SEQUENCE: 248

```
Met Met Pro Leu Leu His Leu Ala Gly Thr Leu Ile Met Ala Leu Phe
 1               5                  10                  15

Leu Ser Cys Leu Arg Pro Gly Ser Leu Asn Pro Cys Ile Glu Val Leu
            20                  25                  30

Pro Asn Ile Thr Tyr Gln Cys Met Asp Gln Asn Leu Ser Lys Ile Pro
        35                  40                  45

His Asp Ile Pro Tyr Ser Thr Lys Asn Leu Asp Leu Ser Phe Asn Pro
    50                  55                  60

Leu Lys Ile Leu Arg Arg Tyr Ser Phe Ser Asn Phe Ser Gln Leu Gln
65                  70                  75                  80

Trp Leu Asp Leu Ser Arg Cys Glu Ile Glu Thr Ile Glu Asp Lys Ala
                85                  90                  95

Trp His Gly Leu Asn Gln Leu Ser Thr Leu Val Leu Thr Gly Asn Pro
            100                 105                 110

Ile Lys Ser Phe Ser Pro Gly Ser Phe Ser Gly Leu Thr Asn Leu Glu
        115                 120                 125

Asn Leu Val Ala Val Glu Thr Lys Met Thr Ser Leu Glu Gly Phe His
    130                 135                 140

Ile Gly Gln Leu Ile Ser Leu Lys Lys Leu Asn Val Ala His Asn Leu
145                 150                 155                 160

Ile His Ser Phe Lys Leu Pro Glu Tyr Phe Ser Asn Leu Thr Asn Leu
                165                 170                 175

Glu His Val Asp Leu Ser Tyr Asn Tyr Ile Gln Thr Ile Ser Val Lys
            180                 185                 190

Asp Leu Gln Phe Leu Arg Glu Asn Pro Gln Val Asn Leu Ser Leu Asp
        195                 200                 205

Leu Ser Leu Asn Pro Ile Asp Ser Ile Gln Ala Gln Ala Phe Gln Gly
    210                 215                 220

Ile Arg Leu His Glu Leu Thr Leu Arg Ser Asn Phe Asn Ser Ser Asn
225                 230                 235                 240

Val Leu Lys Met Cys Leu Gln Asn Met Thr Gly Leu His Val His Arg
                245                 250                 255

Leu Ile Leu Gly Glu Phe Lys Asn Glu Arg Asn Leu Gly Ser Phe Asp
            260                 265                 270

Arg Ser Val Met Glu Gly Leu Cys Asn Val Ser Ile Asp Glu Phe Arg
        275                 280                 285

Leu Thr Tyr Ile Asn His Phe Ser Asp Asp Ile Tyr Asn Leu Asn Cys
    290                 295                 300

Leu Ala Asn Ile Ser Ala Met Ser Phe Thr Gly Val His Ile Lys His
305                 310                 315                 320

Ile Ala Asp Val Pro Arg His Phe Lys Trp Gln Ser Leu Ser Ile Ile
                325                 330                 335

Arg Cys His Leu Lys Pro Phe Pro Lys Leu Ser Leu Pro Phe Leu Lys
            340                 345                 350

Ser Trp Thr Leu Thr Thr Asn Arg Glu Asp Ile Ser Phe Gly Gln Leu
        355                 360                 365

Ala Leu Pro Ser Leu Arg Tyr Leu Asp Leu Ser Arg Asn Ala Met Ser
    370                 375                 380
```

```
Phe Arg Gly Cys Cys Ser Tyr Ser Asp Phe Gly Thr Asn Asn Leu Lys
385                 390                 395                 400

Tyr Leu Asp Leu Ser Phe Asn Gly Val Ile Leu Met Ser Ala Asn Phe
            405                 410                 415

Met Gly Leu Glu Glu Leu Glu Tyr Leu Asp Phe Gln His Ser Thr Leu
        420                 425                 430

Lys Lys Val Thr Glu Phe Ser Val Phe Leu Ser Leu Glu Lys Leu Leu
            435                 440                 445

Tyr Leu Asp Ile Ser Tyr Thr Asn Thr Lys Ile Asp Phe Asp Gly Ile
        450                 455                 460

Phe Leu Gly Leu Ile Ser Leu Asn Thr Leu Lys Met Ala Gly Asn Ser
465                 470                 475                 480

Phe Lys Asp Asn Thr Leu Ser Asn Val Phe Thr Asn Thr Thr Asn Leu
                485                 490                 495

Thr Phe Leu Asp Leu Ser Lys Cys Gln Leu Glu Gln Ile Ser Arg Gly
            500                 505                 510

Val Phe Asp Thr Leu Tyr Arg Leu Gln Leu Leu Asn Met Ser His Asn
        515                 520                 525

Asn Leu Leu Phe Leu Asp Pro Ser His Tyr Lys Gln Leu Tyr Ser Leu
530                 535                 540

Arg Thr Leu Asp Cys Ser Phe Asn Arg Ile Glu Thr Ser Lys Gly Ile
545                 550                 555                 560

Leu Gln His Phe Pro Lys Ser Leu Ala Val Phe Asn Leu Thr Asn Asn
                565                 570                 575

Ser Val Ala Cys Ile Cys Glu Tyr Gln Asn Phe Leu Gln Trp Val Lys
            580                 585                 590

Asp Gln Lys Met Phe Leu Val Asn Val Glu Gln Met Lys Cys Ala Ser
        595                 600                 605

Pro Ile Asp Met Lys Ala Ser Leu Val Leu Asp Phe Thr Asn Ser Thr
        610                 615                 620

Cys Tyr Ile Tyr Lys Thr Ile Ile Ser Val Ser Val Val Ser Val Leu
625                 630                 635                 640

Val Val Ala Thr Val Ala Phe Leu Ile Tyr His Phe Tyr Phe His Leu
            645                 650                 655

Ile Leu Ile Ala Gly Cys Lys Lys Tyr Ser Arg Gly Glu Ser Ile Tyr
            660                 665                 670

Asp Ala Phe Val Ile Tyr Ser Ser Gln Asn Glu Asp Trp Val Arg Asn
        675                 680                 685

Glu Leu Val Lys Asn Leu Glu Glu Gly Val Pro Arg Phe Gln Leu Cys
        690                 695                 700

Leu His Tyr Arg Asp Phe Ile Pro Gly Val Ala Ile Ala Ala Asn Ile
705                 710                 715                 720

Ile Gln Glu Gly Phe His Lys Ser Arg Lys Val Ile Val Val Val Ser
                725                 730                 735

Arg His Phe Ile Gln Ser Arg Trp Cys Ile Phe Glu Tyr Glu Ile Ala
            740                 745                 750

Gln Thr Trp Gln Phe Leu Ser Ser Arg Ser Gly Ile Ile Phe Ile Val
        755                 760                 765

Leu Glu Lys Val Glu Lys Ser Leu Leu Arg Gln Gln Val Glu Leu Tyr
        770                 775                 780

Arg Leu Leu Ser Arg Asn Thr Tyr Leu Glu Trp Glu Asp Asn Ala Leu
785                 790                 795                 800

Gly Arg His Ile Phe Trp Arg Leu Lys Lys Ala Leu Leu Asp Gly
                805                 810                 815
```

```
Lys Ala Leu Asn Pro Asp Glu Thr Ser Glu Glu Glu Gln Glu Ala Thr
                820                 825                 830
Thr Leu Thr
        835

<210> SEQ ID NO 249
<211> LENGTH: 210
<212> TYPE: PRT
<213> ORGANISM: Papio hamadryas

<400> SEQUENCE: 249

Asp Leu Ser Ser Asn Lys Ile Gln Asn Ile Tyr Cys Lys Asp Leu Gln
1               5                   10                  15

Val Leu His Gln Met Pro Leu Pro Asn Leu Ser Leu Asp Leu Ser Leu
            20                  25                  30

Asn Pro Ile Asn Phe Ile Gln Pro Gly Ala Phe Lys Glu Ile Arg Leu
        35                  40                  45

His Lys Leu Thr Leu Arg Ser Asn Phe Asp Asp Leu Asn Val Met Lys
    50                  55                  60

Thr Cys Ile Gln Gly Leu Ala Gly Leu Glu Val His Arg Leu Val Leu
65                  70                  75                  80

Gly Glu Phe Arg Asn Glu Arg Asn Leu Glu Glu Phe Asp Lys Ser Ala
                85                  90                  95

Leu Glu Gly Leu Cys Asn Leu Thr Ile Glu Glu Phe Arg Leu Thr Tyr
            100                 105                 110

Leu Asp Tyr Tyr Leu Asp Asn Ile Ile Asp Leu Phe Asn Cys Leu Ala
        115                 120                 125

Asn Ala Ser Ser Phe Ser Leu Val Ser Val Asn Ile Lys Arg Val Glu
    130                 135                 140

Asp Phe Ser Tyr Asn Phe Arg Trp Gln His Leu Glu Leu Val Asn Cys
145                 150                 155                 160

Lys Phe Glu Gln Phe Pro Thr Leu Glu Leu Glu Ser Leu Lys Arg Leu
                165                 170                 175

Thr Phe Thr Ala Asn Lys Gly Gly Asn Ala Phe Ser Glu Val Asp Leu
            180                 185                 190

Pro Ser Leu Glu Phe Leu Asp Leu Ser Arg Asn Gly Leu Ser Phe Lys
        195                 200                 205

Gly Cys
    210

<210> SEQ ID NO 250
<211> LENGTH: 839
<212> TYPE: PRT
<213> ORGANISM: Homo sapiens

<400> SEQUENCE: 250

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
            20                  25                  30

Val Pro Asn Ile Thr Tyr Gln Cys Met Glu Leu Asn Phe Tyr Lys Ile
        35                  40                  45

Pro Asp Asn Leu Pro Phe Ser Thr Lys Asn Leu Asp Leu Ser Phe Asn
    50                  55                  60

Pro Leu Arg His Leu Gly Ser Tyr Ser Phe Phe Ser Phe Pro Glu Leu
65                  70                  75                  80
```

-continued

```
Gln Val Leu Asp Leu Ser Arg Cys Glu Ile Gln Thr Ile Glu Asp Gly
                 85                  90                  95
Ala Tyr Gln Ser Leu Ser His Leu Ser Thr Leu Ile Leu Thr Gly Asn
            100                 105                 110
Pro Ile Gln Ser Leu Ala Leu Gly Ala Phe Ser Gly Leu Ser Ser Leu
        115                 120                 125
Gln Lys Leu Val Ala Val Glu Thr Asn Leu Ala Ser Leu Glu Asn Phe
    130                 135                 140
Pro Ile Gly His Leu Lys Thr Leu Lys Glu Leu Asn Val Ala His Asn
145                 150                 155                 160
Leu Ile Gln Ser Phe Lys Leu Pro Glu Tyr Phe Ser Asn Leu Thr Asn
                165                 170                 175
Leu Glu His Leu Asp Leu Ser Ser Asn Lys Ile Gln Ser Ile Tyr Cys
            180                 185                 190
Thr Asp Leu Arg Val Leu His Gln Met Pro Leu Leu Asn Leu Ser Leu
        195                 200                 205
Asp Leu Ser Leu Asn Pro Met Asn Phe Ile Gln Pro Gly Ala Phe Lys
    210                 215                 220
Glu Ile Arg Leu His Lys Leu Thr Leu Arg Asn Asn Phe Asp Ser Leu
225                 230                 235                 240
Asn Val Met Lys Thr Cys Ile Gln Gly Leu Ala Gly Leu Glu Val His
                245                 250                 255
Arg Leu Val Leu Gly Glu Phe Arg Asn Glu Gly Asn Leu Glu Lys Phe
            260                 265                 270
Asp Lys Ser Ala Leu Glu Gly Leu Cys Asn Leu Thr Ile Glu Glu Phe
        275                 280                 285
Arg Leu Ala Tyr Leu Asp Tyr Tyr Leu Asp Asp Ile Ile Asp Leu Phe
    290                 295                 300
Asn Cys Leu Thr Asn Val Ser Ser Phe Ser Leu Val Ser Val Thr Ile
305                 310                 315                 320
Glu Arg Val Lys Asp Phe Ser Tyr Asn Phe Gly Trp Gln His Leu Glu
                325                 330                 335
Leu Val Asn Cys Lys Phe Gly Gln Phe Pro Thr Leu Lys Leu Lys Ser
            340                 345                 350
Leu Lys Arg Leu Thr Phe Thr Ser Asn Lys Gly Gly Asn Ala Phe Ser
        355                 360                 365
Glu Val Asp Leu Pro Ser Leu Glu Phe Leu Asp Leu Ser Arg Asn Gly
    370                 375                 380
Leu Ser Phe Lys Gly Cys Cys Ser Gln Ser Asp Phe Gly Thr Thr Ser
385                 390                 395                 400
Leu Lys Tyr Leu Asp Leu Ser Phe Asn Gly Val Ile Thr Met Ser Ser
                405                 410                 415
Asn Phe Leu Gly Leu Glu Gln Leu Glu His Leu Asp Phe Gln His Ser
            420                 425                 430
Asn Leu Lys Gln Met Ser Glu Phe Ser Val Phe Leu Ser Leu Arg Asn
        435                 440                 445
Leu Ile Tyr Leu Asp Ile Ser His Thr His Thr Arg Val Ala Phe Asn
    450                 455                 460
Gly Ile Phe Asn Gly Leu Ser Ser Leu Glu Val Leu Lys Met Ala Gly
465                 470                 475                 480
Asn Ser Phe Gln Glu Asn Phe Leu Pro Asp Ile Phe Thr Glu Leu Arg
                485                 490                 495
Asn Leu Thr Phe Leu Asp Leu Ser Gln Cys Gln Leu Glu Gln Leu Ser
            500                 505                 510
```

```
Pro Thr Ala Phe Asn Ser Leu Ser Leu Gln Val Leu Asn Met Ser
        515                 520                 525

His Asn Asn Phe Phe Ser Leu Asp Thr Phe Pro Tyr Lys Cys Leu Asn
    530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
    610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
    690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
    770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835

<210> SEQ ID NO 251
<211> LENGTH: 160
<212> TYPE: PRT
<213> ORGANISM: Macaca fascicularis

<400> SEQUENCE: 251

Met Leu Pro Phe Leu Phe Phe Ser Thr Leu Phe Ser Phe Ile Phe Thr
1               5                   10                  15

Glu Ala Gln Lys His Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45
```

Asn Pro Cys Ile Lys Leu Lys Gly Ser Arg Gly Leu Leu His Ile Phe
        50                  55                  60

Tyr Ile Pro Arg Arg Asp Val Lys Gln Leu Tyr Phe Asn Leu Tyr Ile
65                      70                  75                  80

Thr Val Asn Ser Met Thr Leu Pro Lys Arg Lys Glu Val Ile Cys Arg
                    85                  90                  95

Gly Ser Asp Asp Tyr Ser Phe Cys Arg Ala Leu Lys Gly Glu Thr
                100                 105                 110

Val Asn Thr Thr Val Ser Phe Ser Phe Lys Gly Ile Lys Phe Ser Lys
                115                 120                 125

Gly Lys Tyr Lys Cys Val Val Glu Ala Ile Ser Gly Ser Pro Glu Glu
        130                 135                 140

Met Leu Phe Cys Leu Glu Phe Asp Ile Ile His Gln Pro Asn Ser Asn
145                 150                 155                 160

<210> SEQ ID NO 252
<211> LENGTH: 160
<212> TYPE: PRT
<213> ORGANISM: Homo sapiens

<400> SEQUENCE: 252

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
                20                  25                  30

Ser Tyr Thr Tyr Cys Asp Lys Met Gln Tyr Pro Ile Ser Ile Asn Val
            35                  40                  45

Asn Pro Cys Ile Glu Leu Lys Gly Ser Lys Gly Leu Leu His Ile Phe
        50                  55                  60

Tyr Ile Pro Arg Arg Asp Leu Lys Gln Leu Tyr Phe Asn Leu Tyr Ile
65                      70                  75                  80

Thr Val Asn Thr Met Asn Leu Pro Lys Arg Lys Glu Val Ile Cys Arg
                    85                  90                  95

Gly Ser Asp Asp Tyr Ser Phe Cys Arg Ala Leu Lys Gly Glu Thr
                100                 105                 110

Val Asn Thr Thr Ile Ser Phe Ser Phe Lys Gly Ile Lys Phe Ser Lys
                115                 120                 125

Gly Lys Tyr Lys Cys Val Val Glu Ala Ile Ser Gly Ser Pro Glu Glu
        130                 135                 140

Met Leu Phe Cys Leu Glu Phe Val Ile Leu His Gln Pro Asn Ser Asn
145                 150                 155                 160

<210> SEQ ID NO 253
<211> LENGTH: 160
<212> TYPE: PRT
<213> ORGANISM: Mus msculus

<400> SEQUENCE: 253

Met Leu Pro Phe Ile Leu Phe Ser Thr Leu Leu Ser Pro Ile Leu Thr
1               5                   10                  15

Glu Ser Glu Lys Gln Gln Trp Phe Cys Asn Ser Ser Asp Ala Ile Ile
                20                  25                  30

Ser Tyr Ser Tyr Cys Asp His Leu Lys Phe Pro Ile Ser Ile Ser Ser
            35                  40                  45

Glu Pro Cys Ile Arg Leu Arg Gly Thr Asn Gly Phe Val His Val Glu
        50                  55                  60

```
Phe Ile Pro Arg Gly Asn Leu Lys Tyr Leu Tyr Phe Asn Leu Phe Ile
 65                  70                  75                  80

Ser Val Asn Ser Ile Glu Leu Pro Lys Arg Lys Glu Val Leu Cys His
                 85                  90                  95

Gly His Asp Asp Tyr Ser Phe Cys Arg Ala Leu Lys Gly Glu Thr
            100                 105                 110

Val Asn Thr Ser Ile Pro Phe Ser Phe Glu Gly Ile Leu Phe Pro Lys
            115                 120                 125

Gly His Tyr Arg Cys Val Ala Glu Ala Ile Ala Gly Asp Thr Glu Glu
            130                 135                 140

Lys Leu Phe Cys Leu Asn Phe Thr Ile Ile His Arg Arg Asp Val Asn
145                 150                 155                 160

<210> SEQ ID NO 254
<211> LENGTH: 160
<212> TYPE: PRT
<213> ORGANISM: Rattus norvegicus

<400> SEQUENCE: 254

Met Leu Pro Phe Phe Leu Phe Ser Thr Leu Leu Ser Pro Ile Phe Thr
  1               5                  10                  15

Glu Ser Glu Arg Gln Gln Trp Ile Cys Asn Ser Ser Asp Ala Ile Ile
                 20                  25                  30

Ser Tyr Ser Tyr Cys Asp His Met Lys Ile Pro Ile Ser Ile Ser Ser
             35                  40                  45

Glu Pro Cys Ile Arg Leu Lys Gly Thr Asn Gly Phe Val His Val Glu
 50                  55                  60

Phe Ile Pro Arg Gly Asn Leu Lys Asn Leu Tyr Phe Asn Leu Phe Ile
 65                  70                  75                  80

Asn Ile Asn Ser Ile Glu Leu Pro Lys Arg Lys Glu Ile Val Cys His
                 85                  90                  95

Gly Tyr Asp Asp Tyr Ser Phe Cys Arg Ala Leu Lys Gly Glu Ala
            100                 105                 110

Val Asn Thr Ala Ile Pro Phe Ser Phe Asp Gly Ile Leu Phe Pro Lys
            115                 120                 125

Gly His His Arg Cys Val Ala Glu Ala Ile Ala Gly Asp Thr Glu Glu
            130                 135                 140

Lys Leu Phe Cys Leu Asn Phe Thr Ile Ile His His Asn Val Asn
145                 150                 155                 160

<210> SEQ ID NO 255
<211> LENGTH: 248
<212> TYPE: PRT
<213> ORGANISM: Rattus norvegicus

<400> SEQUENCE: 255

Met Ser Leu Cys Ser Leu Ala Phe Thr Leu Phe Leu Thr Val Val Ala
  1               5                  10                  15

Gly Ile Lys Cys Asn Val Thr Asp Val Cys Ala Gly Ser Pro Gly Ile
                 20                  25                  30

Pro Gly Ala Pro Gly Asn His Gly Leu Pro Gly Arg Asp Gly Arg Asp
             35                  40                  45

Gly Val Lys Gly Asp Pro Gly Pro Gly Pro Met Gly Pro Pro Gly
 50                  55                  60

Gly Met Pro Gly Leu Pro Gly Arg Asp Gly Leu Pro Gly Ala Pro Gly
 65                  70                  75                  80

Ala Pro Gly Glu Arg Gly Asp Lys Gly Glu Pro Gly Glu Arg Gly Leu
```

-continued

```
                    85                  90                  95
Pro Gly Phe Pro Ala Tyr Leu Asp Glu Glu Leu Gln Thr Glu Leu Tyr
                100                 105                 110

Glu Ile Lys His Gln Ile Leu Gln Thr Met Gly Val Leu Ser Leu Gln
                115                 120                 125

Gly Ser Met Leu Ser Val Gly Asp Lys Val Phe Ser Thr Asn Gly Gln
            130                 135                 140

Ser Val Asn Phe Asp Thr Ile Lys Glu Met Cys Thr Arg Ala Gly Gly
145                 150                 155                 160

Asn Ile Ala Val Pro Arg Thr Pro Glu Glu Asn Glu Ala Ile Ala Ser
                165                 170                 175

Ile Ala Lys Lys Tyr Asn Asn Tyr Val Tyr Leu Gly Met Ile Glu Asp
                180                 185                 190

Gln Thr Pro Gly Asp Phe His Tyr Leu Asp Gly Ala Ser Val Asn Tyr
                195                 200                 205

Thr Asn Trp Tyr Pro Gly Glu Pro Arg Gly Gln Gly Lys Glu Lys Cys
                210                 215                 220

Val Glu Met Tyr Thr Asp Gly Thr Trp Asn Asp Arg Gly Cys Leu Gln
225                 230                 235                 240

Tyr Arg Leu Ala Val Cys Glu Phe
                245

<210> SEQ ID NO 256
<211> LENGTH: 248
<212> TYPE: PRT
<213> ORGANISM: Mus musculus

<400> SEQUENCE: 256

Met Ser Leu Gly Ser Leu Ala Phe Thr Leu Phe Leu Thr Val Val Ala
1               5                   10                  15

Gly Ile Lys Cys Asn Gly Thr Glu Val Cys Ala Gly Ser Pro Gly Ile
                20                  25                  30

Pro Gly Thr Pro Gly Asn His Gly Pro Pro Gly Arg Asp Gly Arg Asp
            35                  40                  45

Gly Ile Lys Gly Asp Pro Gly Pro Pro Gly Pro Met Gly Pro Pro Gly
50                  55                  60

Gly Met Pro Gly Leu Pro Gly Arg Asp Gly Leu Pro Gly Ala Pro Gly
65                  70                  75                  80

Ala Pro Gly Glu His Gly Asp Lys Gly Glu Pro Gly Glu Arg Gly Leu
                85                  90                  95

Pro Gly Phe Pro Ala Tyr Leu Asp Glu Glu Leu Gln Thr Ala Ser Tyr
                100                 105                 110

Glu Ile Lys His Gln Ile Leu Gln Thr Met Gly Val Leu Ser Leu Gln
                115                 120                 125

Gly Ser Met Leu Ser Val Gly Asp Lys Val Phe Ser Thr Asn Gly Gln
            130                 135                 140

Ser Val Asn Phe Asp Thr Ile Arg Glu Met Cys Thr Arg Ala Gly Gly
145                 150                 155                 160

His Ile Ala Ala Pro Arg Asn Pro Glu Glu Asn Glu Ala Ile Ala Ser
                165                 170                 175

Ile Thr Lys Lys Tyr Asn Thr Tyr Pro Tyr Leu Gly Val Ile Glu Gly
                180                 185                 190

Gln Thr Pro Gly Asp Phe His Tyr Leu Asp Gly Ala Ser Val Asn Tyr
                195                 200                 205

Thr Asn Trp Tyr Pro Gly Glu Pro Arg Gly Arg Gly Lys Glu Lys Cys
```

```
                210                 215                 220
Val Glu Met Tyr Thr Asp Gly Lys Trp Asn Asp Lys Gly Cys Leu Gln
225                 230                 235                 240

Tyr Arg Leu Ala Ile Cys Glu Phe
                245
```

<210> SEQ ID NO 257
<211> LENGTH: 57
<212> TYPE: PRT
<213> ORGANISM: Papio cynocephalus

<400> SEQUENCE: 257

```
Met Trp Leu Cys Pro Leu Ala Leu Thr Leu Thr Leu Met Ala Ala Ser
1               5                   10                  15

Gly Ala Ala Cys Glu Val Lys Asp Val Cys Val Gly Ser Pro Gly Ile
            20                  25                  30

Pro Gly Thr Pro Gly Ser His Gly Leu Pro Gly Arg Asp Gly Arg Asp
        35                  40                  45

Gly Val Lys Gly Asp Pro Gly Pro Pro
    50                  55
```

<210> SEQ ID NO 258
<211> LENGTH: 20
<212> TYPE: PRT
<213> ORGANISM: Homo sapiens

<400> SEQUENCE: 258

```
Glu Met Tyr Thr Asp Gly Gln Trp Asn Asp Arg Asn Cys Leu Tyr Ser
1               5                   10                  15

Arg Leu Thr Ile
            20
```

<210> SEQ ID NO 259
<211> LENGTH: 20
<212> TYPE: PRT
<213> ORGANISM: Homo sapiens

<400> SEQUENCE: 259

```
Pro Ala Gly Arg Gly Lys Glu Gln Cys Val Glu Met Tyr Thr Asp Gly
1               5                   10                  15

Gln Trp Asn Asp
            20
```

<210> SEQ ID NO 260
<211> LENGTH: 20
<212> TYPE: PRT
<213> ORGANISM: Homo sapiens

<400> SEQUENCE: 260

```
Ser Phe Val Lys Lys Tyr Asn Thr Tyr Ala Tyr Val Gly Leu Thr Glu
1               5                   10                  15

Gly Pro Ser Pro
            20
```

<210> SEQ ID NO 261
<211> LENGTH: 20
<212> TYPE: PRT
<213> ORGANISM: Homo sapiens

```
<400> SEQUENCE: 261

Ser Leu Gln Gly Ser Ile Met Thr Val Gly Glu Lys Val Phe Ser Ser
1               5                   10                  15

Asn Gly Gln Ser
            20
```